US009796780B2

(12) United States Patent
Mi et al.

(10) Patent No.: US 9,796,780 B2
(45) Date of Patent: Oct. 24, 2017

(54) LINGO-2 ANTAGONISTS FOR TREATMENT OF CONDITIONS INVOLVING MOTOR NEURONS

(71) Applicant: Biogen MA Inc., Cambridge, MA (US)

(72) Inventors: Sha Mi, Belmont, MA (US); R. Blake Pepinsky, Arlington, MA (US)

(73) Assignee: Biogen MA Inc., Cambridge, MA (US)

( * ) Notice: Subject to any disclaimer, the term of this patent is extended or adjusted under 35 U.S.C. 154(b) by 0 days.

(21) Appl. No.: 14/401,002

(22) PCT Filed: May 14, 2013

(86) PCT No.: PCT/US2013/040988
§ 371 (c)(1),
(2) Date: Nov. 13, 2014

(87) PCT Pub. No.: WO2013/173364
PCT Pub. Date: Nov. 21, 2013

(65) Prior Publication Data
US 2015/0118241 A1  Apr. 30, 2015

Related U.S. Application Data

(60) Provisional application No. 61/798,398, filed on Mar. 15, 2013, provisional application No. 61/646,611, filed on May 14, 2012.

(51) Int. Cl.
| A61K 38/00 | (2006.01) |
| A61K 38/40 | (2006.01) |
| C07K 16/28 | (2006.01) |
| C07K 14/47 | (2006.01) |
| C07K 14/705 | (2006.01) |

(52) U.S. Cl.
CPC ...... *C07K 16/2803* (2013.01); *C07K 14/4705* (2013.01); *C07K 14/70503* (2013.01); *C07K 2317/76* (2013.01); *C07K 2319/30* (2013.01)

(58) Field of Classification Search
None
See application file for complete search history.

(56) References Cited

U.S. PATENT DOCUMENTS

| 4,399,216 A | 8/1983 | Axel et al. |
| 4,444,887 A | 4/1984 | Hoffmann |
| 4,510,245 A | 4/1985 | Cousens et al. |
| 4,634,665 A | 1/1987 | Axel et al. |
| 4,694,778 A | 9/1987 | Learn et al. |
| 4,716,111 A | 12/1987 | Osband et al. |
| 4,816,397 A | 3/1989 | Boss et al. |
| 4,816,567 A | 3/1989 | Cabilly et al. |
| 4,946,778 A | 8/1990 | Ladner et al. |
| 4,968,615 A | 11/1990 | Koszinowski et al. |
| 4,987,071 A | 1/1991 | Cech et al. |
| 5,093,246 A | 3/1992 | Cech et al. |
| 5,116,742 A | 5/1992 | Cech et al. |
| 5,122,464 A | 6/1992 | Wilson et al. |
| 5,168,062 A | 12/1992 | Stinski |
| 5,179,017 A | 1/1993 | Axel et al. |
| 5,180,820 A | 1/1993 | Barde et al. |
| 5,223,409 A | 6/1993 | Ladner et al. |
| 5,225,539 A | 7/1993 | Winter |
| 5,252,714 A | 10/1993 | Harris et al. |
| 5,258,498 A | 11/1993 | Huston et al. |
| 5,314,995 A | 5/1994 | Fell, Jr. et al. |
| 5,403,484 A | 4/1995 | Ladner et al. |
| 5,413,923 A | 5/1995 | Kucherlapati et al. |
| 5,427,908 A | 6/1995 | Dower et al. |
| 5,428,130 A | 6/1995 | Capon et al. |
| 5,468,872 A | 11/1995 | Glicksman et al. |
| 5,516,637 A | 5/1996 | Huang et al. |
| 5,530,101 A | 6/1996 | Queen et al. |
| 5,532,351 A | 7/1996 | Stefansson |
| 5,545,806 A | 8/1996 | Lonberg et al. |
| 5,565,332 A | 10/1996 | Hoogenboom et al. |
| 5,565,335 A | 10/1996 | Capon et al. |
| 5,569,825 A | 10/1996 | Lonberg et al. |
| 5,571,698 A | 11/1996 | Ladner et al. |

(Continued)

FOREIGN PATENT DOCUMENTS

| EP | 0 125 023 | 11/1984 |
| EP | 0 171 496 | 2/1986 |

(Continued)

OTHER PUBLICATIONS

Extended European Search Report for EP App. Ser. No. 15160028.5, dated Apr. 24, 2015, 6 pages.
Tanpakushitu Kakusan Kouso (Protein, Nucleic Acid, Enzyme), 1998, 43(2):159-167 (with English abstract).
Adams and Weiner, "Monoclonal antibody therapy of cancer," Nat. Biotechol. 23:1147-1157 (Sep. 2005).
Almagro and Frans Son, "Humanization of antibodies," Frontiers in Bioscience, 13:1619-1633 (2008).
Archer et al., "The natural history of acute painful neuropathy in diabetes mellitus," J Neurol., 46:491-499 (1983).
Barbacid, "The Trk Family of Neurotrophin Receptors," J Neurobiol., 25(11):1386-1403 (1994).
Basso et al., "Basso Mouse Scale for Locomotion Detects Differences in Recovery after Spinal Cord Injury in Five Common Mouse Strains," J Neurotrauma, 23:635-659 (2006).
Basso and Fisher, "The Basso Mouse Scale for Locomotion (BMS) is a more Sensitive Indication of Recovery than the BBB Scale in Mice with Spinal Cord Injury", J Rehab Res Develop., 40(6):26, Supplement 3, abstract P21 (2003).

(Continued)

Primary Examiner — Olga N Chernyshev
(74) Attorney, Agent, or Firm — Fish & Richardson P.C.

(57) ABSTRACT

The invention provides methods of treating diseases, disorders or injuries involving motor neuron survival and axonal growth, including amylotrophic lateral sclerosis, by the administration of a LINGO-2 antagonist. An exemplary method for promoting survival of a motor neuron, comprising contacting said motor neuron with an effective amount of a composition comprising a LINGO-2 antagonist selected from the group consisting of: (i) a soluble LINGO-2 polypeptide; (ii) a LINGO-2 antibody or antigen-binding fragment thereof; (iii) a LINGO-2 antagonist polynucleotide; (iv) a LINGO-2 aptamer; and (v) a combination of two or more of said LINGO-2 antagonists.

9 Claims, 8 Drawing Sheets

(56) References Cited

U.S. PATENT DOCUMENTS

| | | |
|---|---|---|
| 5,574,009 A | 11/1996 | Cohen et al. |
| 5,580,717 A | 12/1996 | Dower et al. |
| 5,585,089 A | 12/1996 | Queen et al. |
| 5,589,369 A | 12/1996 | Seidman et al. |
| 5,605,690 A | 2/1997 | Jacobs et al. |
| 5,625,126 A | 4/1997 | Lonberg et al. |
| 5,633,425 A | 5/1997 | Lonberg et al. |
| 5,658,570 A | 8/1997 | Newman et al. |
| 5,658,727 A | 8/1997 | Barbas et al. |
| 5,661,016 A | 8/1997 | Lonberg et al. |
| 5,693,761 A | 12/1997 | Queen et al. |
| 5,693,762 A | 12/1997 | Queen et al. |
| 5,693,780 A | 12/1997 | Newman et al. |
| 5,698,426 A | 12/1997 | Huse |
| 5,707,829 A | 1/1998 | Jacobs et al. |
| 5,725,859 A | 3/1998 | Orner |
| 5,733,743 A | 3/1998 | Johnson et al. |
| 5,736,137 A | 4/1998 | Anderson et al. |
| 5,750,753 A | 5/1998 | Kimae et al. |
| 5,756,096 A | 5/1998 | Newman et al. |
| 5,770,577 A | 6/1998 | Kinstler et al. |
| 5,772,997 A | 6/1998 | Hudziak et al. |
| 5,780,225 A | 7/1998 | Wigler et al. |
| 5,807,715 A | 9/1998 | Morrison et al. |
| 5,811,524 A | 9/1998 | Brarns et al. |
| 5,814,318 A | 9/1998 | Lonberg et al. |
| 5,821,047 A | 10/1998 | Garrard et al. |
| 5,837,821 A | 11/1998 | Wu |
| 5,840,299 A | 11/1998 | Bendig et al. |
| 5,888,507 A | 3/1999 | Burkly |
| 5,892,019 A | 4/1999 | Schlom et al. |
| 5,910,574 A | 6/1999 | Presta et al. |
| 5,914,237 A | 6/1999 | Godowski et al. |
| 5,939,598 A | 8/1999 | Kucherlapati et al. |
| 5,969,108 A | 10/1999 | McCafferty et al. |
| 6,025,145 A | 2/2000 | Godowski et al. |
| 6,034,119 A | 3/2000 | Ono et al. |
| 6,054,561 A | 4/2000 | Ring |
| 6,075,181 A | 6/2000 | Kucherlapati et al. |
| 6,150,584 A | 11/2000 | Kucherlapati et al. |
| 6,159,730 A | 12/2000 | Reff |
| 6,180,370 B1 | 1/2001 | Queen et al. |
| 6,190,887 B1 | 2/2001 | Boyce et al. |
| 6,193,980 B1 | 2/2001 | Efstathious et al. |
| 6,280,964 B1 | 8/2001 | Kavanaugh et al. |
| 6,333,169 B1 | 12/2001 | Hudziak et al. |
| 6,338,953 B1 | 1/2002 | Boyce et al. |
| 6,387,371 B1 | 5/2002 | Hudziak et al. |
| 6,399,063 B1 | 6/2002 | Hudziak et al. |
| 6,413,777 B1 | 7/2002 | Reff et al. |
| 6,420,140 B1 | 7/2002 | Hori et al. |
| 6,455,277 B1 | 9/2002 | Fox et al. |
| 6,458,592 B1 | 10/2002 | Iakobovits et al. |
| 6,593,290 B1 | 7/2003 | Gao |
| 6,602,503 B1 | 8/2003 | Lobb et al. |
| 6,610,500 B1 | 8/2003 | Saragovi et al. |
| 6,656,465 B2 | 12/2003 | Clary et al. |
| 6,680,209 B1 | 1/2004 | Buechler et al. |
| 6,686,451 B1 | 2/2004 | Desnoyers et al. |
| 6,696,290 B2 | 2/2004 | Fitzpatrick et al. |
| 6,723,701 B2 | 4/2004 | Boone et al. |
| 6,800,607 B2 | 10/2004 | Igarashi et al. |
| 6,881,719 B2 | 4/2005 | Saragovi et al. |
| 6,919,426 B2 | 7/2005 | Boone et al. |
| 6,927,204 B2 | 8/2005 | Gao |
| 6,949,245 B1 | 9/2005 | Sliwkowski |
| 6,974,689 B1 | 12/2005 | Ashkenazi et al. |
| 6,987,088 B2 | 1/2006 | Dennis |
| 7,034,132 B2 | 4/2006 | Anderson et al. |
| 7,098,302 B2 | 8/2006 | Krag et al. |
| 7,205,387 B2 | 4/2007 | Wang et al. |
| 7,223,558 B2 | 5/2007 | Wu et al. |
| 7,693,698 B2 | 4/2010 | Mosyak et al. |
| 7,718,776 B2 | 5/2010 | Boyle et al. |
| 7,750,122 B2 | 7/2010 | Cho et al. |
| 7,785,829 B2 | 8/2010 | Mi et al. |
| 7,816,497 B2 | 10/2010 | Ambati |
| 7,846,438 B2 | 12/2010 | Mi et al. |
| 8,058,406 B2 | 11/2011 | Mi et al. |
| 8,128,926 B2 | 3/2012 | Mi et al. |
| 8,153,580 B2 | 4/2012 | Mi et al. |
| 8,299,221 B2 | 10/2012 | Walmsley et al. |
| 8,309,517 B2 * | 11/2012 | Barker .................. A61K 38/17 514/16.5 |
| 8,425,910 B2 | 4/2013 | Mi et al. |
| 8,460,657 B2 | 6/2013 | Nykjaer et al. |
| 8,486,893 B2 | 7/2013 | Mi et al. |
| 8,551,476 B2 | 10/2013 | Mi et al. |
| 8,609,407 B2 | 12/2013 | Mi et al. |
| 8,642,040 B2 | 2/2014 | Mi et al. |
| 8,765,662 B2 | 7/2014 | Mi et al. |
| 8,932,821 B2 | 1/2015 | Mi et al. |
| 2002/0004587 A1 | 1/2002 | Miller et al. |
| 2002/0077295 A1 | 6/2002 | Strittmatter |
| 2002/0123057 A1 | 9/2002 | Zauderer et al. |
| 2002/0182671 A1 | 12/2002 | Lal et al. |
| 2003/0032589 A1 | 2/2003 | Bartke et al. |
| 2003/0113326 A1 | 6/2003 | He et al. |
| 2003/0143204 A1 | 7/2003 | Lewis et al. |
| 2003/0157641 A1 | 8/2003 | Reff et al. |
| 2003/0162734 A1 | 8/2003 | Miller et al. |
| 2003/0166282 A1 | 9/2003 | Brown et al. |
| 2003/0195163 A1 | 10/2003 | Wu et al. |
| 2003/0216558 A1 | 11/2003 | Morris et al. |
| 2003/0224432 A1 | 12/2003 | Myers et al. |
| 2004/0005579 A1 | 1/2004 | Birse et al. |
| 2004/0009480 A1 | 1/2004 | Anderson et al. |
| 2004/0038278 A1 | 2/2004 | Tzertzinis et al. |
| 2004/0067490 A1 | 4/2004 | Zhong et al. |
| 2004/0086884 A1 | 5/2004 | Beach et al. |
| 2004/0186044 A1 | 9/2004 | Cosgaya et al. |
| 2004/0253605 A1 | 12/2004 | McCarthy et al. |
| 2005/0123990 A1 | 6/2005 | Lal et al. |
| 2005/0153396 A1 | 7/2005 | Baker et al. |
| 2005/0214288 A1 | 9/2005 | Bell et al. |
| 2005/0215770 A1 | 9/2005 | Bell et al. |
| 2005/0271655 A1 | 12/2005 | Lee et al. |
| 2006/0009288 A1 | 1/2006 | deVos et al. |
| 2006/0009388 A1 | 1/2006 | Mi et al. |
| 2006/0034840 A1 | 2/2006 | Agus et al. |
| 2006/0058223 A1 | 3/2006 | Mi et al. |
| 2006/0063200 A1 | 3/2006 | Anderson et al. |
| 2006/0067935 A1 | 3/2006 | Ambati |
| 2006/0088523 A1 | 4/2006 | Andya et al. |
| 2007/0031418 A1 | 2/2007 | Tabares et al. |
| 2007/0059304 A1 | 3/2007 | Cho et al. |
| 2007/0059793 A1 | 3/2007 | Mi et al. |
| 2007/0060526 A1 | 3/2007 | Longo et al. |
| 2007/0071675 A1 | 3/2007 | Wu et al. |
| 2007/0083334 A1 | 4/2007 | Mintz et al. |
| 2007/0105122 A1 | 5/2007 | Ota et al. |
| 2007/0178088 A1 | 8/2007 | Wu et al. |
| 2007/0186296 A1 | 8/2007 | Gao et al. |
| 2007/0213290 A1 | 9/2007 | Kingsman et al. |
| 2007/0274918 A1 | 11/2007 | Mosyak et al. |
| 2009/0017039 A1 | 1/2009 | Mi et al. |
| 2009/0175846 A1 | 7/2009 | Mi et al. |
| 2009/0175872 A1 | 7/2009 | Mi et al. |
| 2009/0246189 A1 | 10/2009 | Mi et al. |
| 2009/0252748 A1 | 10/2009 | Mi et al. |
| 2010/0015131 A1 | 1/2010 | Mi et al. |
| 2010/0074907 A1 | 3/2010 | Mi et al. |
| 2010/0086997 A1 | 4/2010 | Lin et al. |
| 2010/0131432 A1 | 5/2010 | Kennedy et al. |
| 2010/0143362 A1 | 6/2010 | Walmsley et al. |
| 2010/0183317 A1 | 7/2010 | Harima |
| 2010/0204304 A1 | 8/2010 | Mi et al. |
| 2010/0297121 A1 | 11/2010 | Mi et al. |
| 2011/0123553 A1 | 5/2011 | Mi et al. |
| 2011/0311542 A1 | 12/2011 | Mi et al. |
| 2012/0014960 A1 | 1/2012 | Mi et al. |
| 2012/0190070 A1 | 7/2012 | Mi et al. |
| 2012/0230979 A1 | 9/2012 | Mi et al. |
| 2013/0071400 A1 | 3/2013 | Walmsley et al. |

(56) References Cited

U.S. PATENT DOCUMENTS

| | | |
|---|---|---|
| 2013/0273558 A1 | 10/2013 | Mi et al. |
| 2013/0287693 A1 | 10/2013 | Mi et al. |
| 2013/0287796 A1 | 10/2013 | Mi et al. |
| 2013/0323786 A1 | 12/2013 | Mi et al. |
| 2013/0336991 A1 | 12/2013 | Mi et al. |
| 2014/0037639 A1 | 2/2014 | Cortes-Cros et al. |
| 2014/0199315 A1 | 7/2014 | Mi et al. |
| 2015/0238602 A1 | 8/2015 | Cadavid et al. |

FOREIGN PATENT DOCUMENTS

| | | |
|---|---|---|
| EP | 0 173 494 | 3/1986 |
| EP | 0 184 187 | 6/1986 |
| EP | 0 154 316 | 9/1989 |
| EP | 0 401 384 | 12/1990 |
| EP | 0 256 055 | 8/1991 |
| EP | 0 323 997 | 4/1993 |
| EP | 0 396 387 | 12/1993 |
| EP | 0 368 684 | 3/1994 |
| EP | 0 239 400 | 8/1994 |
| EP | 0 338 841 | 3/1995 |
| EP | 0 958 831 | 11/1999 |
| EP | 1 074 617 | 2/2001 |
| EP | 0 058 481 | 5/2003 |
| EP | 0 592 106 | 11/2004 |
| EP | 0 519 596 | 2/2005 |
| EP | 1 574 520 | 9/2005 |
| GB | 2188638 | 10/1987 |
| JP | 9-502730 | 3/1997 |
| JP | 2000-501416 | 2/2000 |
| JP | 2000-514420 | 10/2000 |
| KR | 2013 0007974 | 1/2013 |
| WO | WO 1986/001533 | 3/1986 |
| WO | WO 1986/005807 | 10/1986 |
| WO | WO 1987/002671 | 5/1987 |
| WO | WO 1988/009810 | 12/1988 |
| WO | WO 1989/001036 | 2/1989 |
| WO | WO 1989/010134 | 11/1989 |
| WO | WO 1989/012624 | 12/1989 |
| WO | WO 1990/002809 | 3/1990 |
| WO | WO 1990/011364 | 10/1990 |
| WO | WO 1991/009967 | 7/1991 |
| WO | WO 1991/010737 | 7/1991 |
| WO | WO 1991/010741 | 7/1991 |
| WO | WO 1991/014438 | 10/1991 |
| WO | WO 1991/017271 | 11/1991 |
| WO | WO 1992/001047 | 1/1992 |
| WO | WO 1992/003917 | 3/1992 |
| WO | WO 1992/003918 | 3/1992 |
| WO | WO 1992/008495 | 5/1992 |
| WO | WO 1992/009690 | 6/1992 |
| WO | WO 1992/015679 | 9/1992 |
| WO | WO 1992/018619 | 10/1992 |
| WO | WO 1992/020791 | 11/1992 |
| WO | WO 1992/022324 | 12/1992 |
| WO | WO 1993/001288 | 1/1993 |
| WO | WO 1993/011236 | 6/1993 |
| WO | WO 1994/009817 | 5/1994 |
| WO | WO 1995/007911 | 3/1995 |
| WO | WO 1995/015982 | 6/1995 |
| WO | WO 1995/020401 | 8/1995 |
| WO | WO 1995/021193 | 8/1995 |
| WO | WO 1996/033735 | 10/1996 |
| WO | WO 1996/034096 | 10/1996 |
| WO | WO 1997/000271 | 1/1997 |
| WO | WO 1997/004847 | 11/1997 |
| WO | WO 1997/049406 | 12/1997 |
| WO | WO 1998/016654 | 4/1998 |
| WO | WO 1998/024893 | 6/1998 |
| WO | WO 1998/046645 | 10/1998 |
| WO | WO 1998/050433 | 11/1998 |
| WO | WO 1998/052976 | 11/1998 |
| WO | WO 1999/006427 | 2/1999 |
| WO | WO 1999/014328 | 3/1999 |
| WO | WO 1999/048908 | 9/1999 |
| WO | WO 2000/015796 | 3/2000 |
| WO | WO 2000/031235 | 6/2000 |
| WO | WO 2000/034317 | 6/2000 |
| WO | WO 2000/058473 | 10/2000 |
| WO | WO 2001/004311 | 1/2001 |
| WO | WO 2001/012662 | 2/2001 |
| WO | WO 2001/033042 | 5/2001 |
| WO | WO 2001/040306 | 6/2001 |
| WO | WO 2001/040466 | 6/2001 |
| WO | WO 2001/051520 | 7/2001 |
| WO | WO 2001/055317 | 8/2001 |
| WO | WO 2001/055320 | 8/2001 |
| WO | WO 2001/055333 | 8/2001 |
| WO | WO 2001/057262 | 8/2001 |
| WO | WO 2001/059063 | 8/2001 |
| WO | WO 2002/001047 | 1/2002 |
| WO | WO 2002/014368 | 2/2002 |
| WO | WO 2002/022802 | 3/2002 |
| WO | WO 2002/029058 | 4/2002 |
| WO | WO 2002/029059 | 4/2002 |
| WO | WO 2002/060955 | 8/2002 |
| WO | WO 2002/068579 | 9/2002 |
| WO | WO 2002/096948 | 12/2002 |
| WO | WO 2002/099116 | 12/2002 |
| WO | WO 2003/008583 | 1/2003 |
| WO | WO 2003/014161 | 2/2003 |
| WO | WO 2003/023008 | 3/2003 |
| WO | WO 2003/031462 | 4/2003 |
| WO | WO 2003/035833 | 5/2003 |
| WO | WO 2003/054152 | 7/2003 |
| WO | WO 2003/061559 | 7/2003 |
| WO | WO 2003/083047 | 10/2003 |
| WO | WO 2004/014311 | 2/2004 |
| WO | WO 2004/020404 | 3/2004 |
| WO | WO 2004/022718 | 3/2004 |
| WO | WO 2004/050016 | 6/2004 |
| WO | WO 2004/085648 | 10/2004 |
| WO | WO 2005/016955 | 2/2005 |
| WO | WO 2005/018572 | 3/2005 |
| WO | WO 2005/021579 | 3/2005 |
| WO | WO 2005/035584 | 4/2005 |
| WO | WO 2005/063819 | 7/2005 |
| WO | WO 2005/079566 | 9/2005 |
| WO | WO 2006/002437 | 1/2006 |
| WO | WO 2006/119013 | 11/2006 |
| WO | WO 2006/133533 | 12/2006 |
| WO | WO 2006/136006 | 12/2006 |
| WO | WO 2007/008547 | 1/2007 |
| WO | WO 2007/050866 | 5/2007 |
| WO | WO 2007/056161 | 5/2007 |
| WO | WO 2007/064882 | 6/2007 |
| WO | WO 2007/092370 | 8/2007 |
| WO | WO 2007/098283 | 8/2007 |
| WO | WO 2008/013782 | 1/2008 |
| WO | WO 2008/058736 | 5/2008 |
| WO | WO 2008/086006 | 7/2008 |
| WO | WO 2009/048605 | 4/2009 |
| WO | WO 2009/061500 | 5/2009 |
| WO | 2010/003101 | 1/2010 |
| WO | WO 2010/003108 | 1/2010 |
| WO | WO 2010/005570 | 1/2010 |
| WO | WO 2011/121257 | 10/2011 |
| WO | WO 2014/058875 | 4/2014 |
| WO | WO 2016/112270 | 7/2016 |

OTHER PUBLICATIONS

Battaglia et al., "Protective role of group-II metabotropic glutamate receptors against nigro-striatal degeneration induced by I-methyl-4-phenyl-1,2,3,6-tetrahydropyridine in mice," Neuropharmacol. 45:155-166 (2003).

Baulida and Carpenter, "Heregulin Degradation in the Absence of Rapid Receptor-Mediated Internalization," Exp. Cell Res. 232:167-172 (1997).

Baulida et al., "All ErbB Receptors Other Than the Epidermal Growth Factor Receptor Are Endocytosis Impaired," J. Biol. Chem., 271:5251-5257 (1996).

(56) References Cited

OTHER PUBLICATIONS

Baumann and Pham-Dinh, "Biology of Oligodendrocyte and Myelin in the Mammalian Central Nervous System," J. Physioi. Rev., 81:871-927 (2001).
Binder et al., "Selective Inhibition of Kindling Development by Intraventricular Administration of TrkB Receptor Body," J Neurosci., 19(4):1424-1436 (1999).
Blum, "A null mutation in TGF-a leads to a reduction in midbrain dopaminergic neurons in the substantia nigra," Nat. Neurosci., 1:374-377 (1998).
Boeshore et al., "rtTrkB Isofonns with Distinct Neurotrophin Specificities Are Expressed in Predominantly N onoverlapping Populations of Avian Dorsal Root Ganglion Neurons," II J Neurosci., 19(12):4739-4747 (1999).
Brazil et al., "PKB Binding Proteins: Getting in on the Akt," Cell 111:293-303, (2002).
Brittis and Flanagan, "Nogo Domains and a Nogo Receptor: Implications for Axon Regeneration," Neuron 30:11-14 (2001).
Brummell et al. "Probing the combining site of an anti-carbohydrate antibody by saturation-mutagenesis: role of the heavy-chain CDR3 residues," Biochem., 32:1180-1187 (1993).
Brundin et al., "The rotating 6-hydroxydopamine-lesioned mouse as a model for assessing functional effects of neuronal grafting," Brain Res., 366:346-349 (1986).
Buffo et al., "Application of Neutralizing Antibodies against NI-35/250 Myelin-Associated Neurite Growth Inhibitory Proteins to the Adult Rat Cerebellum Induces Sprouting of Uninjured Purkinje Cell Axons," J Neurosci., 20(6):2275-2286 (2000).
Burks et al., "In vitro scanning saturation mutagenesis of an antibody binding pocket," PNAS 94:412-417 (1997).
Carim-Todd et al., "LRRN6A/LERN1 (leucine-rich repeat neuronal protein 1), a novel gene with enriched expression in limbic system and neocortex," Eur. J. Neurosci., 18:3167-3182 (2003).
Casset et al., "A peptide mimetic of an anti-CD4 monoclonal antibody by rational design," BBRC, 307:198-205 (2003).
Cattaneo et al., "Functional Blockade of Tyrosine Kinase A in a Rat Basal Forebrain by a Novel Antagonistic Anti-Receptor Monoclonal Antibody," J Neuroscience, 19(22):9687-9697 (1999).
Cellerino et al., "Reduced Size of Retinal Ganglion Cell Axons and Hypomyelination in Mice Lacking Brain-Derived Neurotrophic Factor," Mol Cell Neurosci., 9:397-408 (1997).
Ceni and Barker et al., "Getting RIP'd Stunts your Growth," Neuron, 46:839-844 (2005).
Chakrabarti et al., "Critical Role for Kalirin in Nerve Growth Factor Signaling through TrkA," Mol Cell Biol., 25(12):5106-5118 (2005).
Chan et al., "NGF Controls Axonal Receptivity to Myelination by Schwann Cells or Oligodendrocytes," Neuron, 43:183-191 (2004).
Chang et al., "Premyelinating Oligodendrocytes in Chronic Lesions of Multiple Sclerosis," N. Engl. J. Med., 346:165-173 (2002).
Chao et al., "Neurotrophin signaling in health and disease," Clinical Sci., 110:167-173 (2006).
Chard et al., "Progressive grey matter atrophy in clinically early relapsing-remitting multiple sclerosis," Multiple Sclerosis, 10:387-391 (2004).
Chen et al., "A Chemical-Genetic Approach to Studying Neurotrophin Signaling," Neuron, 46:13-21 (2005).
Chen et al., "AMIGO and friends: An emerging family of brain-enriched, neuronal growth modulating, type 1 transmembrane proteins with leucine-rich repeats (LRR) and cell adhesion molecule motifs," Brain Res. Rev., 51:265-74 (Jan. 2006).
Chen et al., "Nogo-A is a Myelin-Associated Neurite Outgrowth Inhibitor and an Antigen for Monoclonal Antibody IN-1," Nature, 403:434-439 (2000).
Chen et al., "Selection and analysis of an optimized anti-VEGF antibody: crystal structure of an affinity-matured Fab in complex with antigen," J. Mol. Biol., 293:865-881 (1999).
Cheng et al., "TrkB Gene Transfer Protects Retinal Ganglion Cells from Axotomy-Induced Death in Vivo," J Neuroscience, 22(10):3977-3986 (2002).
Cheung et al., "Regulation of caspase activation in axotomized retinal ganglion cells," Mol Cell Neurosci., 25:383-393 (2004).
Chiabrando et al., "Low-Density Lipoprotein Receptor-Related Protein Mediates in PC12 Cell Cultures the Inhibition of Nerve Growth Factor-Promoted Neurite Outgrowth by Pregnancy Zone Protein and $\alpha_2$-Macroglobulin," J Neurosci Res., 70:57-64 (2002).
Chinta and Anderson, "Dopaminergic neurons," IJBCB, 37:942-946 (2005).
Citri et al., "The deaf and the dumb: The biology of ErbB-2 and ErbB-3," Exp. Cell Res., 284:54-65 (2003).
Cohen et al., "Nonchromosomal Antibiotic Resistance in Bacteria: Genetic Transformation of *Escherichia coli* by R-Factor DNA," Proc. Natl. Acad. Sci. USA, 69:2110-2114 (1972).
Colello and Pott, "Signals that Initiate Myelination in the Developing Mammalian Nervous System," Mol Neurobiol., 15(1):83-100 (1997).
Coleman and Perry, "Axon pathology in neurological disease: a neglected therapeutic target," Trends in Neurosci., 25:532-537 (2002).
Colman, "Effects of amino acid sequence changes on antibody-antigen interactions," Research in Immunol. 145:33-36 (1994).
Csordas et al,. "Sustained Down-regulation of the Epidermal Growth Factor Receptor by Decorin," J. Biol. Chem., 275:32879-32887 (2000).
Cui et al., "Expression of trkA, trkB, and trkC in Injured and Regenerating Retinal Ganglion Cells of Adult Rats," Investigative Ophthalmology & Visual Science, 43(6):1954-1964 (2002).
Damle and Frost, "Antibody-targeted chemotherapy with immunoconjugates of calicheamicin," Curro Opin. Pharmacal., 3:386-390 (2003).
Daugherty and Mrsny, "Formulation and delivery issues for monoclonal antibody therapeutics," Adv Drug Delivery Rev, 58:686-706 (2006).
De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," J Immunol, 169:3076-3084 (2002).
Dey et al., "CSK negatively regulates nerve growth factor induced neural differentiation and augments AKT kinase activity," Exp. Cell Res., 307(1):1-14 (2005).
Domeniconi et al., "Myelin-Associated Glycoprotein Interacts with the Nog066 Receptor to Inhibit Neurite Outgrowth," Neuron, 35:283-290 (2002).
Domeniconi and Filbin, "Overcoming inhibitors in myelin to promote axonal regeneration," J Neurological Sci., 233:43-47 (Jun. 2005).
Dotti et al., "Human cytotoxic T lymphocytes with reduced sensitivity to Fas-induced apoptosis," Blood, 105:4677-4684 (2005).
Dousset et al. "Lysolecithin-Induced Demyelination in Primates: Preliminary in Vivo Study with MR and Magnetization Transfer," Am J Neuroradiol., 16:225-231 (Feb. 1995).
Dreyfus and Black, "Multiple Approaches to Brain Culture," Cell Culture, 2:3-16 (1990).
Eby et al., "TAJ, a Novel Member of the Tumor Necrosis Factor Receptor Family, Activates the c-Jun N-terminal Kinase Pathway and Mediates Caspaseindependent Cell Death," J. Biol. Chem., 275:15336-15342 (2000).
Eggert et al., "Different Effects of TrkA Expression in Neuroblastoma Cell Lines With or Without MYCN Amplification," Med Pediatr. Oncol., 35(6):623-627 (2000).
Engesser-Cesar et al., "Voluntary Wheel Running Improves Recovery from a Moderate Spinal Cord Injury," J Neurotrauma, 22:157-171 (Jan. 2005).
Esposito et al., "The Cytoplasmic and Transmembrane Domains of the p75 and Trk a Receptors regulate high affinity binding to nerve growth factor," J Biol Chem., 276(35):32687-32695 (2001).
Estaquier et al., "Fas-mediated apoptosis of CD4+ and CD8+ T cells from human immunodeficiency virus-infected persons: differential in vitro preventive effect of cytokines and protease antagonists," Blood, 87:4959-4966 (1996).

(56) References Cited

OTHER PUBLICATIONS

Fendly et al., "The Extracellular Domain of HER2/neu is a Potential Immunogen for Active Specific Immunotherapy of Breast Cancer," J. Biol. Resp. Mod., 9:449-455 (1990).
Ferraro et al., "Molecular Targets to Promote Central Nervous System Regeneration," Current Neurovascular Res., 1:61-75 (2004).
Fisniku et al., "Gray Matter Atrophy Is Related to Long-Term Disability in Multiple Sclerosis," Annals of Neurology, 64(3):247-254 (2008).
Foote and Winter, "Antibody Framework Residues Affecting the Conformation of the Hypervariable Loops," J Mol Bio., 224:487-499 (1992).
Fournier et al., "Identification of a Receptor Mediating Nogo-66 Inhibition of Axonal Regeneration," Nature, 409:341-346 (2001).
Fournier et al., "Truncated soluble Nogo receptor binds Nogo-66 and blocks inhibition of axon growth by myelin," J. Neuroscience, 22(20):8876-8883 (Oct. 15, 2002).
Fu et al., "Blocking LINGO-1 Function Promotes Retinal Ganglion Cell Survival Following Ocular Hypertension and Optic Nerve Transection," Invest. Ophthal. Vis. Sci., 49:975-985 (Mar. 2008).
Fu et al., "Combination Brain-Derived Neurotrophic Factor and LINGO-I Fusion Protein Promote Long-Term Survival to Retinal Ganglion Cells after Ocular Hypertension," Neurosci Res. Abs. 65(1):S171 (2009).
Fu et al., "Combined Effect of Brain-derived Neurotrophic Factor and Lingo-1 Fusion Protein on Long-Term Survival of Retinal Ganglion Cells in Chronic Glaucoma," Neurosci., 162:375-382 (2009).
Fu et al., "LINGO-I Exerts Neuroprotection in a Rat Glaucoma Model," Invest. Ophthalmol. Vis. Sci., 46:157 (2005).
Fu et al., "LINGO-1 negatively regulates TrkB phosphorylation after ocular hypertension," Eur J Neuroscience, 31:1091-1097 (2010).
Fuxe and Ungerstedt, "Antiparkinsonian Drugs and Dopaminergic Neostriatal Mechanisms: Studies in Rats with Unilateral 6-Hydroxydoparnine (=6-OH-DA)- Induced Degeneration of the Nigro-Neostriatal DA Pathway and Quantitative Recording of Rotational Behaviour," Pharmac. Ther., B:41-47 (1976).
Gallo et al., "The trkA Receptor Mediates Growth Cone Turning toward a Localized Source Nerve Growth Factor," J Neurosci., 17(14):5445-5454 (1997).
Galvin et al, "Axon pathology in Parkinson's disease and Lewy body dementia hippocampus contains α-, β-, γ-synuclein," Proc. Natl Acad. Sci. USA, 96:13450-13455 (1999).
Geiger and Peeper, "The Neurotrophic Receptor TrkB in Anoikis Resistance and Metastasis: A Perspective," Cancer Res., 65(16):7033-7036 (2005).
Ghiglione et al., "The Transmembrane Molecule Kekkon 1 Acts in a Feedback Loop to Negatively Regulate the Activity of the *Drosophila* EGF Receptor during Oogenesis," Cell, 96:847-856 (1999).
Gill et al., "Addendum: Direct brain infusion of glial cell line-derived neurotrophic factor in Parkinson disease," Nat. Med., 12:479 (Apr. 2006).
Gill et al., "Direct brain infusion of glial cell line-derived neurotrophic factor in Parkinson disease," Nat. Med., 9:589-595 (2003).
Gille et al., "Oxidative Stress to Dopaminergic Neurons as Models of Parkinson's Disease," Ann. N.y. Acad. Sci., 1018:533-540 (Jun. 2004).
Grandpre et al., "Identification of the Nogo Inhibitor of Axon Regeneration as a Reticulon Protein," Nature, 403:439-444 (2000).
Grandpre et al., "Nogo-66 receptor antagonist peptide promotes axonal regeneration," Nature, 417:547-551 (May 30, 2002).
Grimbergen et al., "Postural instability in Parkinson's disease: the adrenergic hypothesis and the locus coeruleus," Expert Rev. Neurother., 9(2):279-290 (2009).
Grimpe et al., "The Critical Role of Basement Membrane-Independent Laminin γ1 Chain During Axon Regeneration in the CNS," J. Neurosci., 22:3144-3160 (2002).
Gur et al., "LRIG1 restricts growth factor signaling by enhancing receptor ubiquitylation and degradation," EMBO J., 23:3270-3281 (Aug. 2004).
Ha et al., "Membrane Rafts Play a Crucial Role in Receptor Activator of Nuclear Factor KB Signaling and Osteoclast Function," J. Biol. Chem., 278:18573-18580 (2003).
Haines and Rigby, "Expression of Lingo/LERN gene family during mouse embryogenesis," Gene Expression Patterns, 8:79-86 (2008).
Haniu et al., "Interactions between Brain-derived Neurotropic Factor and the TRKB Receptor," J Biol. Chem., 272(40):25296-25303 (1997).
Hartmann et al., "Truncated TrkB receptor-induced outgrowth of dendritic filopodia involves the p75 neurotrophin receptor," J Cell Sci., 117:5803-5814 (2004).
Harwerth et al., "Monoclonal Antibodies against the Extracellular Domain of the erbB-2 Receptor Function as Partial Ligand Agonists," J. Biol. Chem., 267: 15160-15167 (1992).
Hefti et al., "Novel class of pain drugs based on antagonism of NGF," Trends Pharmacol Sci., 27(2):85-91 (2006).
Hoet et al., "Generation of high-affinity human antibodies by combining donor-derived and synthetic complementarity-determining-region diversity," Nat. Biotechnol., 23:344-348 (Mar. 2005).
Hoke et al., "Glial Cell Line-Derived Neurotrophic Factor Alters Axon Schwann Cell Units and Promotes Myelination in Unmyelinated Nerve Fibers," J Neurosci., 23(2):561-567 (2003).
Holm et al., "Functional mapping and single chain construction of the anti-cytokeratin 8 monoclonal antibody TSI," Mol. lmmunol., 44:1075-1084 (2007).
Howland et al., "Focal loss of glutamate transporter EAAT2 in a transgenic rat model of SOD1 mutat-mediated amyotrophic lateral sclerosis (ALS)," Pro Natl Acad Sci USA, 99:1604-1609 (2002).
Huang and Reichardt, "TRK Receptors Roles in Neuronal Signal Transduction," Annu Rev Biochem., 72:609-642 (2003).
Huang and Reichardt, "Neurotrophins: Roles in Neuronal Development and Function," Annu. Rev. Neurosci., 24:677-736 (2001).
Huang et al., "Glial Membranes at the Node of Ranvier Prevent Neurite Outgrowth," Science, 310:1813-7 (Dec. 2005).
Hunt et al., "Nogo receptor mRNA expression in intact and regenerating CNS neurons," Molecular Cellular Neurosci., 20:537-552 (2002).
Ibanez et al., "An extended surface of binding to Trk tyrosine kinase receptors in NGF and BDNF allows the engineering of a multifunctional pan-neurotrophin," EMBO J, 12(6):2281-2293 (1993).
Inoue et al., "Inhibition of the leucine-rich repeat protein LINGO-1 enhances survival, structure, and function of dopaminergic neurons in Parkinson's disease models", Proc Nat Acad Sci, 104(36):14430-14435 (Sep. 4, 2007).
Isacson, "Problems and Solutions for Circuits and Synapses in Parkinson's Disease," Neuron, 43:165-168 (Jul. 2004).
Jellinger et al., "Pathology of Parkinson's Disease, Changes other than the Nigrostriatal Pathway," Molecular Chem Neuropathol., 14:153-197 (1991).
Ji et al., "CNTF promotes survival of retinal ganglion cells after induction of ocular hypertension in rats: the possible involvement of STAT3 pathway," Eur J Neuroscience, 19:265-272 (2004).
Ji et al., "Cyclic AMP controls BDNF-induced TrkB phosphorylation and dendritic pine formation in mature hippocampal neurons," Nature Neuroscience, 8(2):164-172 (2005).
Jones et al., "NG2 Is a Major Chondroitin Sulfate Proteoglycan Produced after Spinal Cord Injury and Is Expressed by Macrophages and Oligodendrocyte Progenitors," J. Neurosci., 22:2792-2803 (2002).
Jonnala and Buccafusco, "Inhibition of nerve growth factor signaling by peroxynitrite," J Neurosci. Res., 63(1):27-34 (2001).
Kaplan and Miller, "Neurotrophin signal transduction in the nervous system," Current Opinion in Neurobiology, 10:381-391, (2000).
Kasper et al, "Structural Basis of Cell-Cell Adhesion by NCAM," Nat. Struct. Biol., 7:389-393 (2000).

(56) References Cited

OTHER PUBLICATIONS

Kernie and Parada, "The Molecular Basis for Understanding Neurotrophins and Their Relevance to Neurologic Disease," Arch Neurol., 57(5):654-657 (2000).
Kim et al., "The Role of ErbB2 Signaling in the Onset of Terminal Differentiation of Oligodendrocytes in Vivo," J. Neurosci., 23:5561-5571 (2003).
Kimpinski, "The Anti-P75 Antibody, MC192, and Brain-Derived Neurotrophic Factor Inhibit Nerve Growth Factor-Dependent Neurite Growth from Adult Sensory Neurons," Neurosci., 93(1):253-263 (1999).
Klapper et al., "A subclass of tumor-inhibitory monoclonal antibodies to ErbB-2/HER2 blocks crosstalk with growth factor receptors," Oncogene, 14:2099-2109 (1997).
Kleitman et al., "Tissue Culture Methods for the Study of Myelination," Culture Nerve Celis, Banker and Goslin, eds., pp. 337-377, MIT Press, Cambridge, Massachusetts, United States (1991).
Knappik et al., "Fully Synthetic Human Combinatorial Antibody Libraries (HuCAL) Based on Modular Consensus Frameworks and CDRs Randomized with Trinucloetides," J. Mol. Biol., 296:57-86 (2000).
Kobayashi et al., "Tryptophan H33 plays an important role in pyrimidine (6-4) pyrimidone photoproduct binding by a high-affinity antibody," Protein Engineering, 12:879-884 (1999).
Kolodny, "Dysmyelinating and demyelinating conditions in infancy," Curro Opin. Neurol. Neurosurg., 6:379-386 (1993).
Kornilova et al., "Lysosomal Targeting of Epidermal Growth Factor Receptors via a Kinase-dependent Pathway Is Mediated by the Receptor Carboxyl-terminal Residues 1022-1123," J. Biol. Chem., 271:30340-30346 (1996).
Kotliarov et al., "Correlation Analysis between Signle-Nucleotide Polymorphism and Expression Arrays in Gliomas Identifies Potentially Relevant Target Genes," Cancer Res., 69:1596-1603 (Feb. 2009).
Kottis et al., "Oligodendrocyte-myelin glycoprotein (OMgp) is an inhibitor of neurite outgrowth," J Neurochem., vol. 82, pp. 1566-1569 (2002).
Laederich et al., "The Leucine-rich Repeat Protein LRIG1 is a Negative Regulator of ErbB Family Receptor Tyrosine Kinases," J. Biol. Chem., 279:47050-47056 (Nov. 2004).
Laederich et al., "The Leucine-rich Repeat Protein LRIG1 is a Negative Regulator of ErbB Family Receptor Tyrosine Kinases," J. Biol. Chem., 279:52806 (Dec. 2004).
Lee and Chao, "Activation ofTrk neurotrophin receptors in the absence of neurotrophins," Proc. Natl. Acad. Sci., 98(6):3555-3560 (2001).
Lee et al., "NGF Regulates the Expression of Axonal LINGO-1 to Inhibit Oligodendrocyte Differentiation and Myelination," J Neurosci., 27(1):220-225 (2007).
Lee et al., "LINGO-1 regulates oligodendrocyte differentiation by inhibiting ErbB2 translocation and activation in lipid rafts," Mol Cellular Neurosci., 60:36-42 (2014).
Lehmann et al., "Inactivation of Rho Signaling Pathway Promotes CNS Axon Regeneration," J Neurosci., 19(17):7537-7547 (1999).
Lehner et al., "How to use RNA interference," Briefings in Functional Genomics 1 and Proteomics, 3(1):68-83 (Apr. 2004).
Lemke, "Myelin and Myelination," in an Introduction to Molecular Neurobiol, Z. Hall, ed., pp. 281-309 (1992).
Li et al., "Blockade of Nogo-66, Myelin-Associated Glycoprotein, and Oligodendrocyte Myelin Glycoprotein by Soluble Nogo-66 Receptor Promotes Axonal Sprouting and Recovery after Spinal Injury," J. Neurosci., 24:10511-10520 (Nov. 2004).
Li et al., "Huntingtin Aggregate-Associated Axonal Degeneration is an Early Pathological Even in Huntington's Disease Mice," J Neurosci., 21:8473-8481 (2001).
Li et al., "Melanopsin-Expressing Retinal Ganglion Cells Are More Injury-Resistant in a Chronic Ocular Hypertension Model," Investigative Ophthalmology & Visual Science 47(7):2951-2958 (2006).
Li et al., "Neutralization of Myelin-Associated NOGO-A by a NOGO Receptor-FC Fusion Protein," Society for Neuroscience Abstracts 333.2 (2002).
Li et al., "Nogo-66 receptor antagonist peptide promotes axonal regeneration and functional recovery after spinal cord injury," Society for Neuroscience Abstract Viewer and Itinerary Planner, Abstract No. 203.4 (2002).
Li et al., "Neutralization of NGR1 may be Sufficient to Promote Rat DRG Neurite Outgrowth in the Presence of CNS Myeline," Society for Neuroscience Meeting Abstracts, Program 678.3, 1 page (Oct. 2003).
Liang et al., "Signaling from Integrins to Fyn to Rho Family GTPases Regulates Morphologic Differentiation of Oligodendrocytes," J. Neurosci., 24:7140-7149 (Aug. 2004).
Lin et al., "Netrin-1 and slit-2 regulate and direct neurite growth of ventral midbrain dopaminergic neurons," Molec. Cell. Neurosci., 28:547-555 (Mar. 2005).
Liu et al., "Enhancement of Schwann cell myelin formation by K252a in the trembler-J mouse dorsal root ganglion explant culture" J Neurosci. Res., 79(3):310-317 (2005).
Liu et al., "Extracellular regulators of axonal growth in the adult central nervous system," Phil. Trans. R. Soc. B, 361:1593-1610 (Sep. 2006).
Llovera et al., "Trk is a calmodulin-binding protein: implications for receptor processing," J Neurochem., 88:422-433 (2004).
Ma et al., "Ligand-Dependent Recruitment of the ErbB4 Signaling Complex into Neuronal Lipid Rafts," J. Neurosci., 23:3164-3175 (2003).
MacCallum et al., "Antibody-antigen interactions: contact analysis and binding sit topography," J. Mol. Biol., 262:732-745 (1996).
Magy et al, "Transient exposure to FGF2 enhances myelination in embryonic brain cell cocultures," Exp. Neurol., 181:17-24 (2003).
Markus et al., "Raf and Akt Mediate Distinct Aspects of Sensory Axon Growth," Neuron, 35:65-76 (2002).
Marmigere et al., "The Runx1/AML1 transcription factor selectively regulates development and survival of TrkA nociceptive sensory neurons," Nat. Neurosci., 9(2):180-187 (2006).
Marsh et al., "SHP-1 negatively regulates neuronal survival by functioning as a TrkA phosphatase," J Cell Biol., 163(5):999-1010 (2003).
Martin et al., "Gene Therapy with Brain-Derived Neurotrophic Factor As a Protection: Retinal Ganglion Cells in a Rat Glaucoma Model," Investigative Ophthalmology & Visual Science, 44(10):4357-4365 (2003).
McDonald and Chao, "Structural Determinants of Neurotrophin Action," J Biol. Chem., 270(34):19669-19672 (1995).
McKerracher et al., "Identification of Myelin-Associated Glycoprotein as a Major Myelin-Derived Inhibitor of Neurite Growth," Neuron, 13:805-811 (1994).
Merrick et al., "Selective Destruction of Stable Microtubules and Axons by Inhibitors of Protein Serine/Threonine Phosphatases in Cultured Human Neurons (NT2N Cells)," J Neurosci., 17:5726-5737 (1997).
Messier et al., "New Techniques in Stereotaxic Surgery and Anesthesia in the Mouse," Pharmacol. Biochem. Behav., 63:313-318 (1999).
Meyer-Franke et al., "Characterization of the Signaling Interactions That Promote the Survival and Growth of Developing Retinal Ganglion Cells in Culture," Neuron, 15(4):805-819 (1995).
Mi et al., "A Novel CNS-Specific Protein Promotes Axonal Elongation by Modulating RHOA Signaling," Society for Neuroscience Abstracts, Abstract No. 891.5, Soc Neurosci., (2003).
Mi et al., "LINGO-1 and its role in CNS repair," Int'l J Biochem Cell Biol., 40:1971-1978 (2008).
Mi et al., "LINGO-1 antagonist promotes spinal cord remyelination and axonal integrity in MOG-induced experimental autoimmune encephalomyelitis," Nat. Med., 13:1228-1233 (Oct. 2007).
Mi et al., "LINGO-1 is a component of the Nogo-66 receptor/p75 signaling complex," Nat. Neurosci., 7:221-8 (Mar. 2004).
Mi et al., "Synctin is a captive retroviral envelope protein involved in human placental morphogenesis," Nature, 403:785-789 (2000).

(56) References Cited

OTHER PUBLICATIONS

Mi et al., "Promotion of Central Nervous System Remyelination by Induced Differentiation of Oligodendrocyte Precursor Cells," Ann Neurol., 65:304-315 (2009).
Mi, et al., "LINGO-1 negatively regulates myelination by oligodendrocytes," Nat. Neurosci., 8:745-51 (May 2005).
Michailov et al., "Axonal Neuregulin-1 Regulates Myelin Sheath Thickness," Sci., 304:700-703 (2004).
Mikol and Stefansson, "A Phosphatidylinositol-Linked Peanut Agglutinin-Binding Glycoprotein in Central Nervous System Myelin and on Oligodendrocytes," J. Cell. Biol., 106:1273-1279 (1988).
Mikol et al., "The oligodendrocyte-myelin glycoprotein belongs to a distinct family of proteins and contains the HNK-1 carbohydrate," J Cell Biol., 110:471-479 (1990).
Miller et al., "Increased Neurite Outgrowth Induced by Inhibition of Protein Tyrosine Kinase Activity in PC12 Pheochromocytoma Cells," J Neurochem., 60(6):2134-2144 (1993).
Morell et al., "Gene Expression in Brain during Cuprizone-Induced Demyelination and Remyelination," Molec. Cell. Neurosci., 12:220-227 (1998).
Mukhopadhyay et al., "A Novel Role for Myelin-Associated Glycoprotein as an Inhibitor of Axonal Regeneration," Neuron, 13:757-767 (1994).
Nagy et al., "Fully human, HLA-DR-specific monoclonal antibodies efficiently induce programmed death of malignant lymphoid cells," Nat. Med., 8:801-807 (2002).
Nagy et al., "Lipid rafts and the local density of ErbB proteins influence the biological role of homo- and heteroassociations of ErbB2," J. Cell Sci., 115:4251-4262 (2002).
NCBI Entrez, Accession No. AY324322, (first available May 4, 2004; last updated May 4, 2004).
NCBI Entrez, Accession No. AY324320, (first available May 4, 2004; last updated May 4, 2004).
NCBI Entrez, Accession No. AY324323, (first available May 4, 2004; last updated May 4, 2004).
NCBI Entrez, Accession No. BC068558, (first available Apr. 6, 2004; last updated Feb. 8, 2007).
NCBI Entrez, Accession No. BC011057, (first available Jul. 30, 2001; last updated Feb. 8, 2007).
NCBI Entrez, Accession No. DR000281, (first available May 17, 2005; last updated May 17, 2005).
NCBI Entrez, Accession No. NM_032808, (first available May 31, 2001; last updated Feb. 11, 2008).
NCBI Entrez, Accession No. NM_152570, (first available Sep. 6, 2002; last updated Feb. 11, 2008).
Nilsson et al., "Neurotrophin-7: a novel member of the neurotrophin family from the zebrafish," FEES Letters, 424:285-2901 (1998).
Nusser et al., "Nerve Growth Factor Signals through TrkA, Phosphatidylinositol 3-Kinase, and Rac1 to Inactivate RhoA during the Initiation of Neuronal Differentiation ofPC12 Cells," J. Biol Chem., 277(39):35840-35846 (2002).
Okafuji et al., "Expression pattern of LINGO-1 in the developing nervous system of the chick embryo," Gene Expr. Patterns, 6:57-62 (Jul. 2005).
O'Leary and Hughes, "Design of Potent Peptide Mimetics of Brain-derived Neurotrophic Factor," J Biol. Chem., 278(28):25738-25744 (2003).
Orlandi et al., "Cloning immunoglobulin variable domains for expression by the polymerase chain reaction," Proc. Natl. Acad. Sci. USA, 86:3833-3837 (1989).
Osada et al., "Assignment of 118 novel cDNAs of cynomolgus monkey brain to human chromosomes," Gene, 275:31-37 (2001).
Padlan et al., "Structure of an antibody-antigen complex: crystal structure of the HyHEL-10 Fab-Iysozyme complex," PNAS, 86:5938-5942 (1989).
Park et al., "A TNF Receptor Family Member, TROY, is a Coreceptor with Nogo Receptor in Mediating the Inhibitory Activity of Myelin Inhibitors," Erratum in Neuron, 3:815 (Mar. 2005).
Park et al., "A TNF Receptor Family Member, TROY, is a Coreceptor with Nogo Receptor in Mediating the Inhibitory Activity of Myelin Inhibitors," Neuron, 3:345- 351 (Feb. 2005).
Park et al., "The erbB2 gene is required for the development of terminally differentiated spinal cord oligodendrocytes," J. Cell Biol., 154:1245-1258 (2001).
Parran et al., "Methylmercury decreases NGF-induced TrkA autophosphorylation and neurite outgrowth in PC12 cells," Developmental Brain Res., 141:71-81 (2003).
Paul ed. Fundamental Immunology, Third Edition. Raven Press, New York, pp. 292-295, under the heading "Fv Structure and Diversity in Three Dimensions," (1993).
Pease et al., "Obstructed Axonal Transport ofBDNF and Its Receptor TrkB in Experimental Glaucoma," Invest Ophthalmol Vis Sci., 41(3):764-74 (2000).
Pepinsky et al., "Exposure Levels of Anti-LINGO-1 Li81 Antibody in the Central Nervous System and Dose-Efficacy Relationships in Rat Spinal Cord Remyelination Models after Systemic Administration," J. Pharmacal. Exp. Ther., 339(2):519-529 (2011).
Persengiev and Kilpatrick, "Nerve growth factor induced differentiation of neuronal cells requires gene methylation," NeuroReport, 8:227-231 (1996).
Pesavento, "Blocking the NGF-TrkA Interaction Rescues the Developmental Loss of LTP in the Rat Visual Cortex: Role of the Cholinergic System," Neuron, 25:165-75 (2000).
Philo et al., "Interactions ofNeurotrophin-3 (NT-3), Brian-derived Neurotrophic Factor (BDNF), and the NT-3•BDNF Heterodimer with the Extracellular Domains of the TrkB and TrkC Receptors," J Biol. Chem., 269(45):27840-27846 (1994).
Pinkas-Kramarski et al., "Neu Differentiation Factor/Neuregulin Isoforrns Activate Distinct Receptor Combinations," J Biol. Chem., 271:19029-19032 (1996).
Plant et al., "Purified Adult Ensheathing Glia Fail to Myelinate Axons under Culture Conditions that Enable Schwann Cells to Form Myelin," J Neurosci., 22:6083-6091 (2002).
Pollack and Harper, "Small Molecule Trk Receptor Agonists and Other Neurotrophic Factor Mimetics," Current Drug Targets—CNS & Neurological Disorders, 1:59-80 (2002).
Qian et al., "Novel Agonist Monoclonal Antibodies Activate TrkB Receptors and Demonstrate Potent Neurotrophic Activities," J Neurosci., 26(37):9394-403 (2006).
Qiu and Goldberg, "Nrdp1/FLRF is a ubiquitin ligase promoting ubiquitination and degradation of the epidermal growth factor receptor family member, ErbB3," Proc. Natl. Acad. Sci. USA, 99:14843-14848 (2002).
Rader, "TNF Receptor-IgG Fc, rDNA," in Biopharmaceutical Products in the US. and European Markets, 5th ed., pp. 610-619 (Jul. 2006).
Rakhit et al., "Nerve Growth Factor Stimulation of p42/p44 Mitogen-Activated Proteu: Kinase in PC12 Cells: Role of $G_{i/o}$, G Protein-Coupled Receptor Kinase 2, β-Arrestin I, and Endocytic Processing," Mol. Pharmacol., 60(1):63-70 (2001).
Rauchenberger et al., "Human Combinatorial Fab Library Yielding Specific and Functional Antibodies against the Human Fibroblast Growth Factor Receptor 3," J. Biol. Chem., 278:38194-38205 (2003).
Reichert et al., "Monoclonal antibody successes in the clinic," Nat. Biotech., 23:1073-1078 (Sep. 2005).
Rosado et al., "Transforming growth factor-/31 regulation of growth zone chondrocytes is mediated by multiple interacting pathways," Biochim. Biophys Acta., 1590:1-15 (2002).
Roux et al., "K252a and CEP1347 are Neuroprotective Compounds that inhibit mixed-linage Kinase-3 and Induce Activation of Akt and ERK," J Biol. Chem., 277(51):49473-49480 (2002).
Rubinson et al., "A lentivirus-based system to functionally silence genes in primary mammalian cells, stem cells and transgenic mice by RNA interference," Nat. Genet., 33:401-406 (2003).
Rudikoff et al., "Single amino acid substitution altering antigen-hinding specificity," PNAS, 79:1979-1983 (1982).
Rudinger, "Characteristics of the amino acids as components of a peptide hormone sequence," in Peptide Hormones, (ed. J.A. Parsons) University Park Press, Baltimore, pp. 1-7 (1976).

(56) References Cited

OTHER PUBLICATIONS

Rudzinski et al., "Changes in Retinal Expression of Neurotrophins and Neurotrophin Receptors Induced by Ocular Hypertension," J Neurobiol., 58(3):341-354 (2004).
Rueda et al. "The Endocannabinoid Anandamide Inhibits Neuronal Progenitor Cell Differentiation through Attenuation of the Rap1/B-Raf/ERK Pathway," J. Biol Chem., 277(48):46645-46650 (2002).
Ruiz et al., "Treatment with trkC agonist antibodies delays disease progression in neuromuscular degeneration (nmd) mice," Hum. Mol. Genet., 14(13):1825-1837 (2005).
Rutishauser and Jessell, "Cell Adhesion Molecules in Vertebrate Neural Development," Physiol. Rev., 68:819-857 (1988).
Saha et al., "Ganglioside mediate the interaction between Nogo receptor 1 and LINGO-1," Biochem Biophysical Res Comm., 413:92-97 (2011).
Saragovi and Burgess, "Small Molecule and protein-based neurotrophic ligands: agonsits and antagonists as therapeutic agents," Exp. Opin. Ther. Patents, 9(6):737-751 (1999).
Schiemann et al., "An Essential Role for BAFF in the Normal Development of B Cells Through a BCMA-Independent Pathway", Science, 293:2111-2114 (2001).
Schmucker et al., "erbB3 is Dispensable for Oligodendrocyte Development in Vitro and in Vivo," Glia, 44:67-75 (2003).
Schori et al., "Vaccination for protection of retinal ganglion cells against death from glutamate cytotoxicity and ocular hypertension: Implications for glaucoma," Proc. Natl. Acad. Sci., 98(6):3398-403 (2001).
Schwab et al., "Inhibitors of Neurite Growth", Annual Review of Neuroscience, 16:565-595 (1993).
Shah et al., "Role of EGF Receptor Transactivation in Phosphoinositide 3-Kinase-Dependent Activation of MAP Kinase by GPCRs," J. Cell. Physiol., 206:47-57 (Jan. 2006).
Shao et al., "TAJ/TROY, an Orphan TNF Receptor Family Member, Binds Nogo-66 Receptor 1 and Regulates Axonal Regeneration," Neuron, 45:353-9 (Feb. 2005).
Shelton et al., "Human trks: Molecular Cloning, Tissue Distribution, and Expression of Extracellular Domain Immunoadhesins," J Neurosci., 15(1-2):477-491 (1995).
Stankoff et al., "Ciliary Neurotrophic Factor (CNTF) Enhances Myelin Formation: A Novel Role for CNTF and CNTF-Related Molecules," J Neurosci., 22(21):9221-9227 (2002).
Stolt et al., "Terminal differentiation of myelin-forming oligodendrocytesdepends on the transcription factor Sox 10," Genes & Dev., 16: 165-170 (2002).
Strohmaier et al., "A splice variant of the neurotrophin receptor trkB with increased specificity for brain-derived neurotrophic factor," EMBO J., 15(13):3332-7 (1996).
Sussman et al., "The ErbB4 Neurogulin Receptor Mediates Suppression of Oligodendrocyte Maturation," J. Neurosci., 25:5757-5762 (Jun. 2005).
Takatori et al., "Local Anesthetics Suppress Nerve Growth Factor-Mediated Neurite Outgrowth by Inhibition of Tyrosine Kinase Activity of TrkA," Anesth. Analg., 102:462-467 (2006).
Taupin et al., "Identification of agonistic and antagonistic antibodies against gp 190, the Leukemia Inhibitory Factor Receptor, reveals distinct roles for its cytokine-binding domains," J Biol. Chem., 376(51):47975-47981 (Dec. 21, 2001).
Taveggia et al. "Neuregulin-1 Type III Determines the Ensheathment Fate of Axons," Neuron, 47:681-694 (2005).
Tezel et al "Immunohistochemical Assessment of the Glial Mitogen-Activated Protein Kinase Activation in Glaucoma," investigative Ophthalmology & Visual Science, 44(7):3025-3033 (2003).
Tong et al., "Intracellular Calcium Levels Influence Apoptosis in Mature Sensory Neurons after Trophic Factor Deprivation," Exp. Neurol., 138:45-52 (1996).
Torkildsen et al., "The cuprizone model for demyelination," Acta Neurol Scand Suppl., 188:72-76 (2008).
Trapp et al., "Axonal pathology in multiple sclerosis: relationship to neurologic disability," Curr Opin. Neurol., 12:295-302 (1999).
Trapp et al., "Pathogenesis of tissue injury in MS lesions," J. Neuroimmunol., 98:49-56 (1999).
Trifunovski et al. "Neuronal activity-induced regulation of LINGO-1," Neuroreport, 15:2397-2400 (Oct. 2004).
Tzahar et al., "Bivalence of EGF-like ligands drives the ErbB signaling network," EMBO J., 16:4938-4950 (1997).
Urfer et al., "High Resolution Mapping of the Binding Site of TrkA for Nerve Growth Factor and TrkC for Neurotrophin-3 on the Second Immunoglobulin-like Domain of the Trk Receptors," J. Biol. Chem., 273(10):5829-5840 (1998).
Vajdos et al., "Comprehensive functional maps of the antigen-binding site of an anti-ErbB2 antibody obtained with shotgun scanning mutagenesis," J. Mol. Biol., 320: 415-428 (2002).
Vartanian et al., "Failure of spinal cord oligodendrocyte development in mice lacking neuregulin," Proc. Natl. Acad. Sci. USA, 96:731-735 (1999).
Viskochil et al., "The Gene Encoding the Oligodendrocyte-Myelin Glycoprotein is Embedded within the Neurofibromatosis Type 1 Gene", Molecular and Cellular Biology, 11:906-912 (1991).
Vourc'h et al., The Oligodendrocyte-Myelin Glycoprotein Gene in Highly Expressed During the Late Stages of Myelination in the Rat Central Nervous System, Developmental Brain Research, 144:159-168 (2003).
Vourc'h et al., "Oligodendrocyte myelin glycoprotein (OMgp) evolution, structure and function," Br Res Rev., 45:115-124 (2004).
Vourc'h et al., "Oligodendrocyte myelin glycoprotein growth inhibition function requires its conserved leucine-rich repeat domain, not its glycosylphosphatidyl-inositol anchor," J Neurochem., 85:889-897 (2003).
Wang et al., "Oligodendrocyte-Myelin Glycoprotein is a Nogo Receptor Ligand That Inhibits Neurite Outgrowth," Nature, 417:941-944 (2002).
West et al., "Parkinson's disease-associated mutations in leucine-rich repeat kinase 2 augment kinase activity," PNAS, 102:16842-16847 (2005).
Wikipedia 2013; File: Spinal cord tracts. At Wikipedia.org/wiki/File:Spinal_cord_tracts_-_English.svg, 4 pages.
Williams and Doherty, "Evidence for and against a Pivotal Role of PI 3-Kinase in a Neuronal Cell Survival Pathway," Molec. Cell. Neurosci., 13:272-280 (1999).
Williams et al., "Overcoming the Inhibitors of Myelin with a Novel Neurotrophin Strategy," J Biol Chem., 280(7):5862-5869 (2006).
Woldemussie et al., "Neuroprotection of Retinal Ganglion Cells by Brimonidine in Rats with Laser-Induced Chronic Ocular Hypertension," Investigative Ophthalmology & Visual Sci., 42(12):2849-2855 (2001).
Woronowicz et al., "Trypanosome trans-sialidase targets TrkA tyrosine kinase receptor and induces receptor internalization and activation," Glycobiology, 14(11):987-998 (2004).
Wu et al., "Humanization of a murine monoclonal antibody by simultaneous optimization of framework and CDR residues," J. Mol. Biol., 294: 151-162 (1999).
Xu et al., "Chaperone-dependent E3 ubiquitin ligase CHIP mediates a degradative pathway for c-ErbB2/Neu," Proc. Natl. Acad. Sci. USA, 99:12847-12852 (2002).
Yamada and Nabeshima, "Brain-Derived Neurotrophic Factor/TrkB Signaling in Memory Processes," J Pharmacal. Sci., 91:267-270 (2003).
Yang et al., "A novel azulenyl nitrone antioxidant protects against MPTP and 3-nitropropionic acid neurotoxicities," Exp. Neural., 191 :86-93 (Jan. 2005).
Yu et al., "Segregation of Nogo66 receptors into lipid rafts in rat brain and inhibition of Nogo66 signaling by cholesterol depletion," FEBS Lett., 577:87-92 (Nov. 2004).
Zaccaro et al., "Selective Small Molecule Peptidomimetic Ligands of TrkC and TrkA Receptors Afford Discrete or Complete Neurotropic Activities," Chem. & Biol., 12:1015-1028 (2005).
Zhou et al., "ErbB2 Degradation Mediated by the Co-chaperone Protein CHIP," J. Biol. Chem., 278:13829-13837 (2003).
Declaration of Robert B. Pepinsky filed in copending U.S. Appl. No. 11/165,576 on Feb. 5, 2009.
Declaration of Robert H. Miller filed in copending U.S. Appl. No. 11/165,576 on May 8, 2008.

(56) References Cited

OTHER PUBLICATIONS

Declaration of Sha Mi filed in copending U.S. Appl. No. 11/165,576 on May 8, 2008.
International Preliminary Report on Patentability dated Jan. 27, 2009, in International Application No. PCT/US2007/016589, 6 pages.
International Preliminary Report on Patentability dated Dec. 28, 2006, in International Application No. PCT/US2005/22881, 5 pages.
International Preliminary Report on Patentability dated Jan. 11, 2011, in International Application No. PCT/US2009/003999, 11 pages.
International Preliminary Report on Patentability dated Jul. 14, 2009, in International Application No. PCT/US2008/000316, 6 pages.
International Preliminary Report on Patentability dated Feb. 24, 2009 in International Application No. PCT/US2006/026271, 8 pages.
International Preliminary Report on Patentability dated Apr. 29, 2008, in International Application No. PCT/US2006/041966, 7 pages.
International Preliminary Report on Patentability dated Sep. 23, 2005, in International Application No. PCT/US2004/008323, 8 pages.
International Preliminary Report on Patentability dated May 6, 2008, in International Application No. PCT/US2006/042990, 5 pages.
International Preliminary Report on Patentability dated Apr. 13, 2010, in International Application No. PCT/US2008/011633, 7 pages.
International Preliminary Report on Patentability dated May 11, 2010, in International Application No. PCT/US2008/012620, 8 pages.
International Preliminary Report on Patentability dated Jun. 4, 2008, in International Application No. PCT/US2006/045993, 8 pages.
International Preliminary Report on Patentability dated Nov. 27, 2014, in International Application No. PCT/US2013/040988, 9 pages.
International Search Report and Written Opinion for International Application No. PCT/US2008/11633, dated Feb. 18, 2009, 8 pages.
International Search Report and Written Opinion for International Application No. PCT/US2008/12620, dated Feb. 26, 2009, 10 pages.
International Search Report and Written Opinion in International Application No. PCT/US2007/016589, dated Oct. 2, 2008, 8 pages.
International Search Report and Written Opinion in International Application No. PCT/US2006/26271, dated Jan. 27, 2009, 21 pages.
International Search Report for International Application No. PCT/US2004/008323, dated Oct. 15, 2004, 5 pages.
International Search Report for International Application No. PCT/US2006/42990, dated Apr. 18, 2007, 3 pages.
International Search Report and Written Opinion in International Application No. PCT/US2005/022881, dated Oct. 31, 2006, 7 pages.
International Search Report for International Patent Application No. PCT/US2006/45993 dated Sep. 28, 2007, 7 pages.
International Search Report for International Application No. PCT/US2009/003999, dated Mar. 8, 2010, 9 pages.
International Search Report dated Sep. 16, 2008, in International Application No. PCT/US2008/00316, 4 pages.
International Search Report and Written Opinion in International Application No. PCT/US2006/041966, dated Jul. 9, 2007, 9 pages.
International Search Report in International Application No. PCT/US2013/040988, dated Nov. 1, 2013, 5 pages.
Supplementary European Search Report for EP Application No. 06 83 6888, search completed on Dec. 11, 2009, 8 pages.
Supplementary European Search Report for European Application No. 06 83 8776, dated Nov. 10, 2009, 4 pages.
Supplementary European Search Report for European Application No. 08 84 8257, dated Jan. 18, 2013, 4 pages.
Supplementary European Search Report for European Application No. EP 05 76 4255, The Hauge, Netherlands, dated Nov. 5, 2009, 3 pages.
Supplementary European Search Report for European Application No. EP 08 83 7617, European Patent Office, Germany, dated Apr. 19, 2012, 4 pages.
Supplementary Partial European Search Report for European Application No. EP 06836566, completed on Jun. 26, 2009, Munich, Germany, 7 pages.
Altschul et al., "Basic local alignment search tool" J. Mol. Biol. 215:403-10 (1990), 8 pages.
Altschul et al., "Gapped BLAST and PSI-BLAST: a new generation of protein database search programs" Nucleic Acids Res. 25:3389-3402 (1997), 14 pages.
Balcer et al., "Evaluating loss of visual function in multiple sclerosis as measured by low-contrast letter acutiy," Neurogology 74(13):816-23 (2010), 8 pages.
Barbas, et al., "Assembly of combinatorial antibody libraries on phage surfaces: the gene III site" PNAS 88:7978-7982 (1991), 5 pages.
Barrette et al., "Expression profile of receptors for myelin-associated inhibitors of axonal regeneration in the intact and injured mouse central nervous system" Mol Cell neurosci 34:519-38 (2007), 20 pages.
Bitsch et al., "Acute axonal injury in multiple sclerosis. Correlation with demyelination and inflammation" Brain 123:1174-1183 (2000), 10 pages.
Chothia, C., et al., "Canonical structures for the hypervariable regions of immunoglobulins" J. Mol. Biol. 196:901-917 (1987), 18 pages.
E. Meyers; W. Miller, "Optimal alignments in linear space," Computer applications in the Biosciences: CABIOS 4:11-17 (1989), 13 pages.
Ferguson et al., "Axonal damage in acute multiple sclerosis lesions" Brain 120:393-399 (1997), 7 pages.
Gram, et al., "In vitro selection and affinity maturation of antibodies from a naive combinatorial immunoglobulin library" PNAS 89:3576-3580 (1992), 5 pages.
Griffths et al., "Human anti-self antibodies with high specificity from phage display libraries" Embo Biol 12:725-734 (1993), 10 pages.
Hauser et al., "The Neurobiology of Multiple Sclerosis: Genes, Inflammation and Neurodegeneration" Neuron, 52(1):61-76 (2006), 16 pages.
Hoogenboom et al., "Multi-subunit proteins on the surface of filamentous phage: methodologies for displaying antibody (Fab) heavy and light chains" Nuc Acid Res 19:4133-4137 (1991), 5 pages.
Huston et al., "Protein engineering of antibody binding sites: recovery of specific activity in an anti-digoxin single-chain Fv analogue produced in *Escherichia coli*" Proc. Natl. Acad. Sci. USA 85:5879-5883 (1988), 5 pages.
International Preliminary Report on Patentability dated Apr. 14, 2015, in International Application No. PCT/US2013/06387, 13 pages.
International Search Report and Written Opinion in International Application No. PCT/US2013/063873, dated Jul. 4, 2014, 20 pages.
Ji et al., "Assessment of functional recovery and axonal sprouting in oligodendrocyte-myelin glycoprotein (OMgp) null mice after spinal cord injury" Mol Cell Neurosci. 39:258-67 (2008), 22 pages.
Kohler, "Immunoglobulin chain loss in hybridoma lines" Proc. Natl. Acad. Sci. USA 77:2197 (1980), 3 pages.
Liu et al., "Chimeric mouse-human IgG1 antibody that can mediate lysis of cancer cells" PNAS 84:3439-3443 (1987), 5 pages.
Llorens et al., "Developmental analysis of Lingo-1/Lern1 protein expression in the mouse brain: interaction of its intracellular domain with Myt1l" Dev Neurobiol 68:521-41 (2008), 21 pages.
Lowy et al., "Isolation of transforming DNA: cloning the hamster aprt gene" Cell 22:817 (1980), 7 pages.

(56) References Cited

OTHER PUBLICATIONS

Macay, "Real-Time Rapid Acuity Assessment Using VEPs: Development and Validation of the Step VEP Technique," Am Invest Ophthalmol Vis Sci. 49(1): 438-41 (2008), 4 pages.
Mi et al., "Blocking LINGO-1 as a therapy to promote CNS repair: From concept to the clinic," CNS Drugs, 27(7):493-503, Jul. 2013, 11 pages.
Mulligan, "The basic science of gene therapy" Science 260:926-932 (1993), 8 pages.
Nishimura et al., "Recombinant human-mouse chimeric monoclonal antibody specific for common acute lymphocytic leukemia antigen" Canc. Res. 47:999-1005 (1987), 8 pages.
O'Hare et al., "Transformation of mouse fibroblasts to methotrexate resistance by a recombinant plasmid expressing a prokaryotic dihydrofolate reductase" Proc. Natl. Acad. Aci. USA 78:1527 (1981), 5 pages.
Peterson et al., "VCAM-1-positive microglia target oligodendrocytes at the border of multiple sclerosis lesions" J Neuropathol Exp Neurol 61:539-546 (2002), 8 pages.
Presta et al., "Engineering of therapeutic antibodies to minimize immunogenicity and optimize function," Advanced Drug Delivery Reviews, Elsevier, Aug. 2006, 58(5-6):640-656, 17 pages.
Proudfoot, "Transcriptional interference and termination between duplicated alpha-globin gene constructs suggests a novel mechanism for gene regulation" Nature 322:562-565 (1986), 4 pages.
Ransohoff, R.M., "Animal models of multiple sclerosis: the good, the bad and the bottom line," Nature Neuroscience 15(8):1074-1077 (2012), 4 pages.
Reiter, Y., "Antibody engineering of recombinant Fv immunotoxins for improved targeting of cancer: disulfide-stabilized Fv immunotoxins" Clin Cancer Res 2:245-52 (1996), 9 pages.
Robinson "Gene therapy—proceeding from laboratory to clinic," TIB TECH 11(5):155 (1993), 1 page, 1 page.
Streltsov, "Structure of a shark IgNAR antibody variable domain and modeling of an early-developmental isotype" Protein Sci. 14:2901-2909 (2005), 9 pages.
Sun et al., "Chimeric antibody with human constant regions and mouse variable regions directed against carcinoma-associated antigen 17-1A" PNAS 84:214-218 (1987), 5 pages.
Supplementary European Search Report for European Application No. EP 13 79 0850, dated Jan. 13, 2016, 14 pages.
T Hart et al., "Modelling of multiple sclerosis: lessons learned in a non-human primate," The Lancet Neurology 3(10):588-597 (2004), 10 pages.
Trapp et al., "Axonal transection in the lesions of multiple sclerosis" N Engl J Med 338:278-285 (1998), 8 pages.
Tuaillon et al., "Human immunoglobulin heavy-chain minilocus recombination in transgenic mice: gene-segment use in mu and gamma transcripts" PNAS 90:3720-3724 (1993), 5 pages.
Wigler et al., "Transfer of purified herpes virus thymidine kinase gene to cultured mouse cells" Cell 11:223 (1977), 10 pages.
Wigler et al., "Transformation of mammalian cells with an amplifiable dominant-acting gene" Natl. Acad. Sci. USA 77:3567 (1980), 4 pages.
Zhao et al., "Inactivation of Glycogen Synthase Kinase-3β and Up-regulation of LINGO-1 are Involved in LINGO-1 Antagonist Regulated Survival of Cerebellar Granular Neurons," Cell Mol Neurobiol. 28:737-35 (2008), 9 pages.
Behan, et al., "The sad plight of multiple sclerosis research (low on fact, high on fiction): critical data to support it being a neurocristopathy," Inflammopharmacology 18:265-290 (2010), 26 pages.
Beidler et al., "Cloning and high level expression of a chimeric antibody with specificity for human carcinoembryonic antigen" J. Immunol. 141:4053-4060 (1988), 8 pages.
Better et al., *Escherichia coli* secretion of an active chimeric antibody fragment" Science 240:1041-1043 (1988), 3 pages.
Bird et al., "Single-chain antigen-binding proteins" Science 242:423-426 (1988), 4 pages.

Bjartmar et al., "Axonal and neuronal degeneration in multiple sclerosis: mechanisms and functional consequences" Curr Opin Neurol 14:271-278 (2001), 8 pages.
Bjartmar et al., "Axonal pathology in myelin disorders" J Neurocytol 28:383-395 (1999), 13 pages.
Bock, M., et al., "Impairment of contrast visual acuity as a functional correlate of retinal nerve fibre layer thinning and total macular volume reduction in multiple sclerosis" Br J Ophthalmol. 96(1):62-7 (2012), 6 pages.
Bruggeman et al., "Human antibody production in transgenic mice: expression from 100 kb of the human IgH locus" Eur J Immunol 21:1323-1326 (1991), 4 pages.
Bruggeman et al., "Desinger Mice: The Production of Human Antibody Repertoires in Transgenic Animals," Year Immunol 7:33-40 (1993), 8 pages.
Clackson et al., "Making antibody fragments using phage display libraries" Nature 352:624-628 (1991), 5 pages.
Cockett et al., "High level expression of tissue inhibitor of metalloproteinases in Chinese hamster ovary cells using glutamine synthetase gene amplification" Biotechnology 8: 662-667 (1990), 6 pages.
Colcher, D., et a., "Single-chain antibodies in pancreatic cancer" Ann NY Acad Sci 880:263-80 (1999), 18 pages.
Extended European Search Report in European Application No. 15183027.0, dated Nov. 19, 2015, 10 pages.
Foecking et al., "Powerful and versatile enhancer-promoter unit for mammalian expression vectors" Gene 45:101 (1986), 5 pages.
Fuchs et al., "Targeting Recombinant Antibodies to the Surface of *Escherichia coli*: Fusion to a Peptidoglycan Associated Lipoprotein" Biotechnology 9:1370-1372 (1991), 4 pages.
Garrard et al., "Fab assembly and enrichment in a monovalent phage display system" Biotechnology 9:1373-1377 (1991), 5 pages.
Green, L.L. et al., "Antigen-specific human monoclonal antibodies from mice engineered with human Ig heavy and light chain YACs" Al. Nature Genet. 7:13-21 (1994), 9 pages.
Hawkins et al., "Selection of phage antibodies by binding affinity. Mimicking affinity maturation" J Mol Biol 226:889-896 (1992), 8 pages.
Hay et al., "Bacteriophage cloning and *Escherichia coli* expression of a human IgM Fab" Hum Antibod Hybridomas 3:81-85 (1992), 5 pages.
Huse et al., "Generation of a large combinatorial library of the immunoglobulin repertoire in phage lambda" Science 246:1275-1281 (1989), 7 pages.
Jasmin; Ohara, "Remyelination within the CNS: do schwann cells pave the way for oligodendrocytes?" Neuroscientists 8(3):198-203 (2003), 6 pages.
Ji et al., "LINGO-1 antagonist promotes functional recovery and axonal sprouting after spinal cord injury" Mol Cell Neurosci. 33(3):11-20 (2006), 10 pages.
Kurtze, "Clinical Definition for Multiple Sclerosis Treatment Trials," Ann. Neurol. 36:573-79 (1994), 7 pages.
Liu et al., "Production of a mouse-human chimeric monoclonal antibody to CD20 with potent Fc-dependent biologic activity" J. Immunol. 139:3521-3526 (1987), 6 pages.
Lobuglio et al., "Phase I clinical trial of CO17-1A monoclonal antibody" Hybridoma 5:S117-123 (1986), 7 pages.
Longberg, N., et al. "Antigen-specific human antibodies from mice comprising four distinct genetic modifications" Nature 368:856-859 (1994), 4 pages.
Lv et al., "Passive immunization with LINGO-1 polyclonal antiserum afforded neuroprotection and promoted functional recovery in a rat model of spinal cord injury" Neuroimmonomodulation 17: 270-8 (2010), 9 pages.
Morgan; Anderson, "Human gene therapy" Ann. Rev. Biochem. 62:191-217 (1993), 27 pages.
Morrison, S. L., Transfectomas provide novel chimeric antibodies Science 229:1202-1207 (1985), 6 pages.
Mulligan; Berg, "Selection for animal cells that express the *Escherichia coli* gene coding for xanthine-guanine phosphoribosyltransferase," Proc. Natl. Sci. USA 78:2072 (1981), 5 pages.

(56) References Cited

OTHER PUBLICATIONS

Murdoch, et al., "Spotlight on Subcutaneous Recombinant Interferon-beta-1a (Rebif) in Relapsing-Remitting Multiple Sclerosis" Biodrugs 19(5)323-325 (2005), 3 pages.
Needleman; Wunsch, "A general method applicable to the search for similarities in the amino acid sequence of two proteins" J. Mol. Biol. 48:444-453 (1970), 11 pages.
Oi et al., "Chimeric antibodies" Biotechniques 4:214 (1986), 9 pages.
Park et al., "Transcriptional regulation of artemin is related to neurite outgrowth and actin polymerization in mature DRG neurons," Neurosci Letter 404:61-6 (2006).
Ridgway, A.A.G., "Mammalian Expression Vector" Butterworths 470-472 (1988), 26 pages.
Saleh et al., "A phase II trial of murine monoclonal antibody 17-1A and interferon-gamma: clinical and immunological data" Cancer Immunol. Immunother. 32:185-190 (1990), 6 pages.
Santerre et al., "Expression of prokaryotic genes for hygromycin B and G418 resistance as dominant-selection markers in mouse L cells" Gene 30:147 (1984), 10 pages.
Sha Mi et al., "Promotion of central nervous systems remyelination by induced differentiation of oligodendrocyte precursor cells", Annals of Neurology 65(3):304-315 (2009), 12 pages. XP055098017, ISSN: 0364-5134, DOI: 10.1002/ana.21581.
Shaw et al., "Mouse/human chimeric antibodies to a tumor-associated antigen: biologic activity of the four human IgG subclasses" J. Natl Cancer Inst. 80:1553-1559 (1988), 7 pages.
Tolstoshev, "Gene therapy, concepts, current trials and future directions" Ann. Rev. Pharmacol. Toxicol. 32:573-596 (1993), 24 pages.
Verhoeyan et al., "Reshaping human antibodies: grafting an antilysozyme activity" Science 239:1534 (1988), 3 pages.
Vick et al., "Role of adult oligodendrocytes in remyelination after neural injury" J. Neurotrauma 9(1):593-103 (1992), 11 pages.
Werkerle et al., "Animal models of multiple sclerosis" Drug Discovery Today: Disease Models 3(4):359-367 (2006), 9 pages.
Wood et al., "The synthesis and in vivo assembly of functional antibodies in yeast" Nature 314:446-449 (1985), 4 pages.
Wu et al., "MR diffusion changes correlate with ultra-structurally defined azonal degeneration in murine optic nerve" NeuroImage 37:1138-1147 (2007), 10 pages.
Wu; Wu, "Delivery systems for gene therapy" Biotherapy 3:87-95 (1991), 9 pages.
Yamashita et al., "Multiple signals regulate axon regeneration through the Nogo receptor complex" Mol Neurobiol 32:105-11 (2005), 7 pages.
Biogen Report Top-Line Results from Phase 2 Study of Opicinumab (Anti-LINGO-1) in Multiple Sclerosis, Jun. 7, 2016, Business Wire, A Berkshire Hathaway Company, [retrieved Apr. 18, 2017], Retrieved from the Internet: http://www.businesswire.com/news/home/20160607005718/en, 3 pages.
Cadavid et al., "Efficacy Analysis of the Anti-LINGO-1 Monoclonal Antibody BIIB033 in acute Optic Neuritis: the RENEW Trial (P7.202)," Neurology, 84(14):Suppl. P7.202 (Apr. 2015).
Dubessy et al., "Biotherapies in multiple sclerosis: a step toward remyelination and neuroprotection?," Revue Neurologique Dec., 170(12):770-778 (Dec. 2014).
International Search Report and Written Opinion in International Application No. PCT/US2016/012609, dated Jun. 22, 2016, 23 pages.
Irvine et al., "Remyelination protects axons from demyelination-associated axon degeneration," Brain, 131(6):1464-1477 (Jan. 2008).
Ledford, "Drug that boosts nerve signals offers hope for multiple sclerosis," Nature, 520:417 (Apr. 2015).
Mullard, "An audience with Doug Williams," Nature Reviews Drug Discovery, 13(1):880-881 (Dec. 2014).
Oh et al., "Emerging injectable therapies for multiple sclerosis," Lancet Neurol., 12:1115-1126 (Oct. 2013).
Pepinsky et al., "Structure of the LINGO-1 Anti-LINGO-1 Li81 Antibody Complex Provides Insights into the Biology of LINGO-1 and the Mechanism of Action of the Antibody Therapy," Journal of Pharmacology and Experimental Therapeutics, 350(1):110-123 (Apr. 2014).
Sha Mi et al., "Blocking LINGO-1 as a therapy to promote CNS repair: from concept to the clinic,"CNS Drugs, 27(7):493-503 (Jul. 2013).
Sha Mi et al., "LINGO-1 antagonist promotes spinal cord remyelination and axonal integrity in MOG-induced experimental autoimmune encephalomyelitis," Nature Medicine, 13(10):1228-1233 (Sep. 2007).

\* cited by examiner

Blocking LINGO-2 by Soluble LINGO-2 Promotes Motor Neurons Axon Growth

LINGO-2 ANTAGONISTS FOR TREATMENT OF CONDITIONS INVOLVING MOTOR NEURONS

BACKGROUND OF THE INVENTION

Motor neurons are neurons that control muscle function. They are located in the central nervous system and have axons that extend outside of the central nervous system in order to control muscles. Normally, upper motor neurons, which are located in the brain, transmit signals to lower motor neurons, which are located in the spinal cord, and the lower motor neurons direct muscle activity. Muscles are of course important for many activities including breathing, swallowing, talking, and walking. Therefore, damage to motor neurons or decreased motor neuron function can have devastating clinical effects, and a number of conditions associated with motor neurons have been indentified.

Such conditions include, but are not limited to, the following diseases, disorders, and injuries: amyotrophic lateral sclerosis (ALS), primary lateral sclerosis (PLS), progressive muscular atrophy (PMA), hereditary spastic paraparesis (HSP), X-linked spinobulbar muscular atrophy (SBMA; Kenney disease), progressive bulbar palsy, pseudo-bulbar palsy, spinal muscular atrophy (SMA), post-polio syndrome (PPS), Huntington's disease, Essential tremor (ET), motor neuron disease, paralysis, and Parkinson's disease. ALS is one of the prominent of these diseases, with 1 to 2 out of 100,000 people developing ALS each year ALS is a rapidly progressive disease that is associated with the destruction of both upper and, lower motor neurons and results in the loss of voluntary muscle movement.

Some disease-modifying treatments are available for ALS and, other motor-neuron related diseases, including the use of Riluzole, which blocks certain sodium, channels that are associated with damaged neurons. While such treatments may slow disease course, there are currently no cures for motor neuron disease. Therefore, therapies that promote regeneration of the axons of motor neurons and/or promote the survival of motor neurons are of great need for patients with diseases associated with insufficient motor neuron function.

BRIEF SUMMARY OF THE INVENTION

LINGO-2 (FLJ31810, Leucine -rich repeat and immuno-globulin-like domain-containing nogo receptor-interacting protein 2, LERN3, Leucine-rich repeat neuronal protein 3, Leucine-rich repeat neuronal protein 6C, LERN6C, PRO31993, or UNQ9234) is expressed in cortical neurons and dorsal root ganglion (DRG) neurons and negatively regulates motor neuron survival and motor neuron axonal length. Antagonists of LINGO-2 can be used to promote survival and growth of motor neurons both in vivo and in vitro. For example, antibodies, antigen-binding fragments thereof, and derivatives thereof can be used as antagonists of LINGO-2. Soluble LINGO-2 polypeptides and nucleic acids containing a nucleotide sequence encoding a polypeptide that corresponds to a region of LINGO-2 can also be used as antagonists of LINGO-2. Accordingly, methods for promoting survival of motor neurons and axonal growth of motor neurons by contacting a motor neuron with a LINGO-2 antagonist are provided herein.

Certain embodiments of the invention encompass the following (wherein each embodiment is indicated by a capital letter "E" followed by an number):

E1) An isolated binding molecule that can specifically bind to the same LINGO-2 epitope as the C09 antibody.

E2) The isolated binding molecule of E1, wherein said binding molecule competitively inhibits the C09 antibody from binding to LINGO-2.

E3) An isolated binding molecules comprising at least one complementarity determining region (CDR) of the C09 antibody.

E4) The binding, molecule according to any one of E1-E3, which comprises an antibody or antigen-binding fragment thereof.

E5) The binding molecule of any one of E1-E4, comprising variable heavy domain (VH) CDRs 1-3 of C09 wherein one or more VH CDRs have 3 or fewer single amino acid substitutions.

E6) The binding molecule of E5, comprising VH CDRs 1-3 of C09.

E7) The binding molecule of any one of E1-E6, comprising variable light domain (VL) CDRs 1-3 of C09, wherein one or more VL CDRs have 3 or fewer single, amino acid substitutions.

E8) The binding molecule of E7, comprising VL CDRs 1-3 of C09.

E9) The binding molecule of any one of E1-E4, comprising VH CDRs 1-3 and VL CDRs 1-3 of C09.

E10) The binding molecule of any one of E1-E9, comprising a VH, wherein the VH comprises an amino acid sequence at least 85%, 90%, or 95% identical to the VH of C09.

E11) The binding molecule of E10, wherein the VH comprises an amino acid sequence identical to the VH of C09.

E12) The binding molecule of any one of E1-E11, comprising a VL, wherein the VL comprises an amino acid sequence at least 85%, 90%, or 95% identical to the VL of C09.

E13) The binding molecule of E12, wherein the VL comprises an amino acid sequence identical to the VL of C09.

E14) The binding molecule of any one of E1-E13, comprising a VH and a VL, wherein the VH and the VL comprise amino acid sequences at least 85%, 90%, or 95% identical to the VH and VL of C09.

E15) The binding molecule of E14, wherein the VH and VL comprise amino acid sequences identical to the VH and VL of C09.

E16) The binding molecule of any one of E1-E15, wherein the binding molecule binds to the LINGO-2 LRR domain.

E17) The binding molecule of E16, wherein the binding molecule binds to an epitope in LRR7-LRR12 of LINGO-2.

E18) The binding molecule of E16, wherein the binding molecule binds to an epitope in amino acids 202-343 of SEQ ID NO:2.

E19) The binding molecule of any one of E1-E18, wherein the binding molecule binds to the region of LINGO-2 from amino acids 28-408 of SEQ ID NO:2 or amino acids 410-500 of SEQ ID NO:2.

E20) The binding molecule of any one of E1-E19, wherein the binding molecule binds to human, rat, and mouse LINGO-2.

E21) The binding molecule of any one of E1-E19, wherein the binding molecule binds to human and rat LINGO-2.

E22) The binding molecule of any one of E1-E19, wherein the binding molecule binds to human and mouse LINGO-2.

E23) The binding molecule of any one of E1-E19, wherein the binding molecule binds to human LINGO-2.

E24) The binding molecule of any one of E1-E23, wherein the binding molecule promotes motor neuron survival.

E25) The binding molecule of any one of E1-E24, wherein the binding molecule promotes motor neuron axon growth.

E26) The binding molecule of any one of E1-E25, wherein the binding molecule promotes oligodendrocyte differentiation.

E27) The binding molecule of any one of E1-E26, wherein the binding molecule promotes myelination.

E28) The binding molecule of any one of E1-E27, wherein the binding molecule promotes AKT phosphorylation.

E29) The binding molecule of any one of E1-E28, which comprises a human antibody, a chimeric antibody, or a humanized antibody.

E30) The binding molecule of any one of E1-E28, which comprises a naturally-occurring antibody, an scFv fragment, an Fab fragment, an F(ab')2 fragment, a minibody, a diabody, a triabody, a tetrabody, or a single chain antibody.

E31) The binding molecule of any one of E1-E28, which comprises a monoclonal antibody.

E32) An isolated polynucleotide comprising a nucleic acid encoding a VH, wherein the VH comprises the VH CDRs 1-3 of C09.

E33) An isolated polynucleotide comprising a nucleic acid encoding a VH, wherein the VH comprises an amino acid sequence at least 85%, 90%, 95% identical, or identical to the VH of C09.

E34) An isolated polynucleotide comprising a nucleic acid encoding a VL, wherein the VL comprises the VL CDRs 1-3 of C09.

E35) An isolated polynucleotide comprising a nucleic acid encoding a VL, wherein the VL comprises an amino acid sequence at least 85%, 90%, 95% identical, or identical to the VL of C09.

E36) The polynucleotide of any one of E32-E35, wherein an antibody or antigen-binding fragment thereof comprising said VH, said VL, or said VH and said VL can specifically bind to LINGO-2.

E37) The polynucleotide of E36, wherein the antibody or antigen-binding fragment thereof specifically binds to the same epitope as the C09 antibody.

E38) The polynucleotide of, any one of E32-E37, wherein an antibody or antigen-binding fragment thereof comprising said VH, said VL, or said VH and said VL can bind to the LINGO-2 LRR domain.

E39) The polynucleotide of any one of E32-E37, wherein an antibody or antigen-binding fragment thereof comprising said VH, said VL, or said VH and said VL can bind an epitope in LRR7-LRR12 in LINGO-2.

E40) The polynucleotide of any one of E32-E37, wherein an antibody or antigen-binding fragment thereof comprising said VH, said VL, or said VH and said VL can bind to the region of LINGO-2 from amino acids 28-408 of SEQ ID NO:2 or amino acids 410-500 of SEQ ID NO:2.

E41) The polynucleotide of any one of E32-E37, wherein an antibody or antigen-binding fragment thereof comprising said VH, said VL, or said VH and said VL can bind an epitope in amino acids 202-343 of LINGO-2.

E42) The polynucleotide of any one of E32-E41, wherein an antibody or antigen-binding fragment thereof comprising said VH, said VL, or said VH and said VL can bind to human, rat, and mouse LINGO-2.

E43) The polynucleotide of any one of E32-E41, wherein an antibody or antigen-binding fragment thereof comprising said VH, said VL, or said VH and said VL can bind to human and rat LINGO-2.

E44) The polynucleotide of any one of E32-E41, wherein an antibody or antigen-binding fragment thereof comprising said VH, said VL, or said VH and said VL can bind to human and mouse LINGO-2.

E45) The polynucleotide of any one of E32-E41, wherein an antibody or antigen-binding fragment thereof comprising said VH, said VL, or said VH and said VL can bind to human LINGO-2.

E46) The polynucleotide of any one of E32-E45, wherein an antibody or antigen-binding fragment thereof comprising said VH, said VL, or said VH and said VL can promote motor neuron survival.

E47) The polynucleotide of any one of E32-E45, wherein an antibody or antigen-binding fragment thereof comprising said VH, said VL, or said VH and said VL can promotes motor neuron axon growth.

E48) A polynucleotide encoding the binding molecule of any one of E1-E31.

E49) A vector comprising the polynucleotide of any one of E32-E48.

E50) A composition comprising a polynucleotide comprising a nucleic acid encoding a VH and polynucleotide comprising a nucleic acid encoding a VL, wherein the VH and the VL comprise amino acid sequences at least 85%, 90%, 95% identical, or identical to the VH and VL of C09.

E51) A composition comprising a polynucleotide comprising a nucleic acid encoding a VH and polynucleotide comprising a nucleic acid encoding a VL, wherein the VH CDRs 1-3 and the VL CDRs 1-3 are the VH CDRs 1-3 and the VL CDRs 1-3 of C09.

E52) The composition of E50 or E51, wherein the polynucleotide comprising a nucleic acid encoding a VH and the polynucleotide comprising a nucleic acid encoding a VL are in the same vector.

E53) The composition of E50 or E51, wherein the polynucleotide comprising a nucleic acid encoding a VH and the polynucleotide comprising a nucleic acid encoding a VL are in different vectors.

L54) The composition of any one of E50 E53, wherein an antibody or antigen-binding fragment thereof comprising said VH and said VL can specifically bind to LINGO-2.

E55) The composition of E54, wherein the antibody or antigen-binding fragment thereof can specifically bind to the same epitope as the C09 antibody.

E56) The composition of any one of E50-E55, wherein an antibody or antigen-binding fragment thereof comprising said VH and said VL can bind to the LINGO-2 LRR domain.

E57) The composition of any one of E50-E55 wherein an antibody or antigen-binding fragment thereof comprising said VH and said VL can bind to an epitope in LRR2-LRR7 of LINGO-2.

E58) The composition of any one of E50-E55, wherein an antibody or antigen-binding fragment thereof comprising said VH and said VL can bind to the region of LINGO-2 from amino acids 28-403 of SEQ ID NO:2 or amino acids 410-500 of SEQ ID NO:2.

E59) The composition of any one of E50-E55, wherein an antibody or antigen-binding fragment thereof comprising said VH and said VL can bind to an epitope in amino acids 202-343 of LINGO-2.

E60) The composition of any one of E50-E59, wherein an antibody or antigen-binding fragment thereof comprising said VH and said VL can bind to human, rat, and mouse LINGO-2.

E61) The composition of any one of E50-E59, wherein an antibody or antigen-binding fragment thereof comprising said VH and said VL can bind to human and rat LINGO-2.

E62) The composition of any one of E50-E59, wherein an antibody or antigen-binding fragment thereof comprising said VH and said VL can bind to human and mouse LINGO-2.

E63) The composition of any one of E50-E59, wherein an antibody or antigen-binding fragment thereof comprising said VH and said VL can bind to human LINGO-2.

E64) The composition of any one of E50-E63, wherein an antibody or antigen-binding fragment thereof comprising said VH and said VL can promote motor neuron survival.

E65) The composition of any one of E50-E63, wherein an antibody or antigen-binding fragment thereof comprising said VH and said VL can promote motor neuron axon growth.

E66) The polypeptide encoded by the polynucleotide of any one of E32-E47.

E67) A composition comprising a VH, polypeptide and a VL polypeptide, wherein the VH and the VL comprise amino acid sequences at least 85%, 90%, 95% identical, or identical to the VH and VL of C09.

E68) A composition comprising a VH polypeptide and a VL polypeptide, wherein the VH CDRs 1-3 and the VL CDRs 1-3 are the VH CDRs 1-3 and the VL CDRs 1-3 of C09.

E69) The composition of E67 or E68, wherein an antibody or antigen-binding fragment thereof comprising said VH and said VL can specifically bind to LINGO-2.

E70) The composition of E69, wherein the antibody or antigen-binding fragment thereof can specifically bind to the same epitope as the C09 antibody.

E71) The composition of any one of E67-E70, wherein an antibody or antigen-binding fragment thereof comprising said VH and said VL can bind to the LINGO-2 LRR domain.

E72) The composition of any one of E67-E70, wherein an antibody or antigen-binding fragment thereof comprising said VH or said VL can bind to an epitope in LRR7-LRR12 of LINGO-2.

E73) The composition of any one of E67-E70, wherein an antibody or antigen-binding fragment thereof comprising said VH or said VL can bind to the region of LINGO-2 from amino acids 28-408 of SEQ ID NO:2 or amino acids 410-500 of SEQ ID NO:2.

E74) The composition of any one of E67-E70, wherein an antibody or antigen-binding fragment thereof comprising said VH or said VL can bind to an epitope in amino acids 202-343 of LINGO-2.

E75) The composition of any one of E67-E74, wherein an antibody or antigen-binding fragment thereof comprising said VH or said VL can bind to human, rat, and mouse LINGO-2.

E76) The composition of any one of E67-E74, wherein an antibody or antigen-binding fragment thereof comprising said VH or said VL can bind to human and rat LINGO-2.

E77) The composition of any one of E67-E74, wherein an antibody or antigen-binding fragment thereof comprising said VH or said VL can bind to human and mouse LINGO-2.

E78) The composition of any one of E67-E74, wherein an antibody or antigen-binding fragment thereof comprising said VH or said VL can bind to human LINGO-2.

E79) The composition of any one of E67-E78, wherein an antibody or antigen-binding fragment thereof comprising said VH and said VL can promote motor neuron survival.

E80) The composition of any one of E67-E78, wherein an antibody or antigen-binding fragment thereof comprising said VH and said VL can promote motor neuron axon growth.

E81) A host cell comprising the polynucleotide of any one of E32-E48, the vector of E49, the composition of any one of E50-E65 or E67-E80, or the polypeptide of E66.

E82) A method of producing an anti-LINGO-2 binding molecule, comprising culturing the host cell of E81, and recovering said binding molecule.

E83) An anti-LINGO-2 binding molecule, produced by the method of E82.

E84) A method for detecting LINGO-2 expression in a sample comprising (a) contacting said sample with the binding molecule of any one of E1-E31 of E83 and (b) detecting binding of said binding molecule in said sample.

E85) A pharmaceutical composition comprising (a) the binding molecule of any one of E1-E31 or E83, the polynucleotide of any one of E32-E48, the vector of E49, the composition of any one of E50-E65 or E67-E80, the polypeptide of E66, or the host cell of E81 and (b) a carrier.

E86) An isolated nucleic acid comprising a polynucleotide encoding a soluble fragment of the polypeptide of SEQ ID NO:2, or a variant thereof, wherein said polypeptide is capable of promoting survival of a motor neuron.

E87) An isolated nucleic acid comprising a polynucleotide encoding a soluble fragment of the polypeptide of SEQ ID NO:2, or a variant thereof, wherein said polypeptide is capable of promoting survival of decreasing inhibition of axonal growth of a motor neuron.

E88) The nucleic acid of E86 or E87, comprising a polynucleotide encoding a polypeptide comprising an amino acid sequence at least 90% identical to a reference amino acid sequence selected from the group, consisting of amino acids 1 to 500 of SEQ ID NO:2.

E89) The nucleic acid of E88, wherein the polypeptide comprises an amino acid sequence at least 95% identical to said reference amino acid sequence.

E90) The nucleic acid of E88, wherein the polypeptide comprises an amino acid sequence identical to said reference amino acid sequence.

E91) The nucleic acid of any one of E86-E90, further comprising a polynucleotide encoding a heterologous polypeptide fused to said polypeptide.

E92) The nucleic acid of E91, wherein said heterologous polypeptide is selected from the group consisting of an immunoglobulin, serum albumin, a targeting polypeptide, a reporter polypeptide, a purification-facilitating polypeptide, a fragment of any of said polypeptides, and a combination of two or more of said polypeptides or fragments.

E93) The nucleic acid of E92, wherein said heterologous polypeptide is selected from the group consisting of immunoglobulin Fc, human serum albumin or fragment thereof, a histidine tag, and a motor neuron glycoprotein or fragment thereof.

E94) A composition comprising a pharmaceutically acceptable carrier and the nucleic acid of any one of E86-E93.

E95) A vector comprising the nucleic acid of any one of E86-E93.

E96) The vector of E95, wherein said nucleic acid is operatively linked to an expression control sequence.

E97) The vector of E96, wherein said vector is a viral vector.

E98) The vector of E97, wherein said viral vector is selected from the group consisting, of an adenoviral vector, a lentiviral vector, a baculoviral vector, an Epstein Barr viral vector, a papovaviral vector, a vaccinia viral vector, and a herpes simplex viral vector.

E99) A host cell comprising the nucleic acid of any one of E86-E93 or the vector of any one of E95-E98.

E100) The host cell of E99, which expresses said polypeptide.

E101) An isolated polypeptide encoded by the nucleic acid of any one of E86-E93.

E102) The polypeptide of E101, wherein said polypeptide is produced synthetically.

E103) The polypeptide of E101 or E102, wherein said polypeptide is conjugated to a polymer.

E104) The polypeptide of E103, wherein said polymer is selected from the group consisting of a polyalkylene glycol, a sugar polymer, and a polypeptide.

E105) The polypeptide of E104, wherein said polyalkylene glycol is polyethylene glycol (PEG).

E106) The polypeptide of any one of E103-E105, wherein said polypeptide is conjugated to 1, 2, 3 or 4 polymers.

E107) The polypeptide of E106, wherein the total molecular weight of the polymers is from 20,000 Da to 40,000 Da.

E108) An antibody or antigen-binding fragment thereof, which can specifically bind to the polypeptide of E101 or E102, wherein said antibody or antigen-binding fragment is capable of promoting survival of a motor neuron.

E109) An antibody or antigen-binding fragment thereof, which can specifically bind to the polypeptide of E101 or E102, wherein said antibody or antigen-binding fragment is capable of decreasing inhibition of axonal growth of a motor neuron.

E110) An antibody or antigen-binding fragment thereof, which can specifically bind to the polypeptide of E101 or E102, wherein said antibody or antigen-binding fragment is capable of promoting oligodendrocyte differentiation.

E111) An antibody or antigen-binding fragment thereof, which can specifically bind to the polypeptide of E101 or E102, wherein said antibody or antigen-binding fragment is capable of promoting myelination.

E112) An antibody or antigen-binding fragment thereof, which can specifically bind to the polypeptide of E101 or E102, wherein said antibody or antigen-binding fragment is capable of promoting AKT phosphorylation.

E113) An antibody or antigen-binding fragment thereof, which can specifically bind to the polypeptide of E101 or E102, wherein said antibody or antigen-binding fragment to the LINGO-2 LRR domain.

E114) An antibody or antigen-binding fragment thereof, which can specifically bind to the polypeptide of E101 or E102, wherein said antibody or antigen-binding fragment an epitope in amino acids 202-343 of SEQ ID NO:2.

E115) An antibody or antigen-binding fragment thereof, which can specifically bind to to the polypeptide of E101 or E102, wherein said antibody or antigen-binding fragment binds to the region of LINGO-2 from amino acids 28-408 of SEQ ID NO:2 or amino acids 410-500 of SEQ ID NO:2.

E116) An antibody or antigen-binding fragment thereof, which can specifically bind to to the polypeptide of E101 or E102, wherein said antibody or antigen-binding fragment binds to the LINGO-2 LRRNT or LRRCT domain.

E117) An antibody or antigen-binding fragment thereof, which can specifically bind to to the polypeptide of E101 or E102, wherein said antibody or antigen-binding fragment binds to the LINGO-2 immunoglobulin domain.

E118) A composition comprising a pharmaceutically acceptable carrier the polypeptide of any one of E102-E107.

E 119) A composition comprising a pharmaceutically acceptable carrier the host cell of E99 or E100.

E120) A method for promoting survival of a motor neuron, comprising contacting said motor neuron with an effective amount of a composition comprising a LINGO-2 antagonist selected from the group consisting of (i) a soluble LINGO-2 polypeptide; (ii) a LINGO-2 antibody or antigen-binding fragment thereof; (iii) a LINGO-2 antagonist polynucleotide; (iv) a LINGO-2 aptamer; and (v) a combination of two or more of said LINGO-2 antagonists.

E121) A method for promoting axonal growth of a motor neuron, comprising contacting said motor neuron with a composition comprising a LINGO-2 antagonist selected from the group consisting of: (i) a soluble LINGO-2 polypeptide; (ii) a LINGO-2 antibody or antigen-binding fragment thereof; (iii) a LINGO-2 antagonist polynucleotide; (iv) a LINGO-2 aptamer; and (v) a combination of two or more of said LINGO-2 antagonists.

E122) A method for promoting survival of a motor neuron in a mammal, comprising administering to a mammal in need thereof an effective amount of a composition comprising a LINGO-2 antagonist selected from the group consisting of: (i) a soluble LINGO-2 polypeptide; (ii) a LINGO-2 antibody or antigen-binding fragment thereof; (iii) a LINGO-2 antagonist polynucleotide; (iv) a LINGO-2 aptamer; and (v) a combination of two or more of said LINGO-2 antagonists.

E123) A method for promoting axonal growth of a motor neuron in a mammal, comprising administering to a mammal in need thereof an effective amount of a composition comprising a LINGO-2 antagonist selected from the group consisting of: (i) a soluble LINGO-2 polypeptide; (ii) a LINGO-2 antibody or antigen-binding fragment thereof; (iii) a LINGO-2 antagonist polynucleotide; (iv) a LINGO-2 aptamer; and (v) a combination of two or more of said LINGO-2 antagonists.

E124) A method for treating a disease, disorder, or injury associated with survival of a motor neuron in a mammal comprising administering to a mammal in need thereof a therapeutically effective amount of a composition comprising a LINGO-2 antagonist selected from the group consisting of (i) a soluble LINGO-2 polypeptide; (ii) a LINGO-2 antibody or antigen-binding fragment thereof; (iii) a LINGO-2 antagonist polynucleotide; (iv) a LINGO-2 aptamer; and (v) a combination of two or more of said LINGO-2 antagonists.

E125) A method for treating a disease, disorder, or injury associated with axonal growth of motor neurons in a mammal comprising administering to a mammal in need thereof a therapeutically effective amount of a composition comprising a LINGO-2 antagonist selected from the group consisting of (i) a soluble LINGO-2 polypeptide; (ii) a LINGO-2 antibody or antigen-binding fragment thereof; (iii) a LINGO-2 antagonist polynucleotide; (iv) a LINGO-2 aptamer; and (v) a combination of two or more of said LINGO-2 antagonists.

E126) A method for treating, a disease, disorder, or injury associated with oligodendrocyte death or lack of differentiation in a mammal comprising administering to a mammal in need thereof a therapeutically effective amount of a composition comprising a LINGO-2 antagonist selected from the group consisting of (i) a soluble LINGO-2 polypeptide; (ii) a LINGO-2 antibody or antigen-binding fragment thereof; (iii) a LINGO-2 antagonist polynucleotide;

(iv) a LINGO-2 aptamer; and (v) a combination of two or more of said LINGO-2 antagonists.

E127) A method for treating a disease, disorder, or injury associated with demylination in a mammal comprising administering to a mammal in need thereof a therapeutically effective amount of a composition comprising a LINGO-2 antagonist selected from the group consisting of (i) a soluble LINGO-2 polypeptide; (ii) a LINGO-2 antibody or antigen-binding fragment thereof; (iii) a LINGO-2 antagonist polynucleotide; (iv) a LINGO-2 aptamer; and (v) a combination of two or more of said LINGO-2 antagonists.

E128) A method for treating a disease, disorder, or injury associated with dysmyelination in a mammal comprising administering to a mammal in need thereof a therapeutically effective amount of a composition comprising a LINGO-2 antagonist selected from the group consisting of: (i) a soluble LINGO-2 polypeptide; (ii) a LINGO-2 antibody or antigen-binding fragment thereof; (iii) a LINGO-2 antagonist polynucleotide; (iv) a LINGO-2 aptamer; and (v) a combination of two or more of said LINGO-2 antagonists.

E129) The method of any one of E120-E128, wherein said LINGO-2 antagonist is a soluble LINGO-2 polypeptide.

E130) The method of E129, wherein said LINGO-2 antagonist comprises the polypeptide of any one of E102-E107.

E131) The method of E129, wherein said soluble LINGO-2 polypeptide comprises a LINGO-2 region selected from the group consisting of: (i) a LINGO-2 Ig domain or a fragment, variant, or derivative thereof, (ii) a LINGO-2 LRR domain or a fragment, variant, or derivative thereof, and (iii) a combination of said LINGO-2 domains or fragments, variants, or derivatives thereof.

E132) The method of E130 or E131, wherein said soluble LINGO-2 polypeptide lacks a LINGO-2 region selected from the group consisting of (i) a LINGO-2 transmembrane domain or a fragment, variant, or derivative thereof, (ii) a LINGO-2 intracellular domain or a fragment, variant, or derivative thereof, and (iii) a combination of said LINGO-2 domains or fragments, variants, or derivatives thereof.

E133) The method of any one of E120-E128, wherein said LINGO-2 antagonist is a LINGO-2 antibody or antigen-binding fragment thereof.

E134) The method of E133, wherein said LINGO-2 antibody or antigen-binding fragment thereof is the binding molecule of any one of E1-E28 and E80.

E135) The method of any one of E120-E128, wherein said LINGO-2 antagonist comprises a LINGO-2 antagonist polynucleotide.

E136) The method of E135, wherein said LINGO-2 antagonist polynucleotide is selected from the group consisting of (i) an antisense polynucleotide; (ii) a ribozyme; (iii) a small interfering RNA (siRNA); and (iv) a small-hairpin RNA (shRNA).

E137) The method of any one of E120-E128, wherein said LINGO-2 antagonist comprises an LINGO-2 aptamer.

E138) The method of any one of E122-E127, wherein said mammal has been diagnosed with a disease, disorder, or injury involving motor neurons.

E139) The method of any one of E124, E125, or E138, wherein said disease, disorder, or injury is selected from the group consisting of amyotrophic lateral sclerosis (ALS), primary lateral sclerosis (PLS), progressive muscular atrophy (PMA), hereditary spastic paraparesis (HSP), X-linked spinobulbar muscular atrophy (SBMA; Kenney disease), progressive bulbar palsy, pseudo-bulbar palsy, spinal muscular atrophy (SMA), post-polio syndrome (PPS), Hunting-ton's disease, Essential tremor (ET), motor neuron disease, paralysis, and Parkinson's disease.

E140) The method of E139, wherein said disease, disorder, or injury is amylotrophic lateral sclerosis (ALS).

E141) The method of any one of E120-E140, wherein said LINGO-2 antagonist is administered by bolus injection or chronic infusion.

E142) The method of any one of E120-E140, wherein said LINGO-2 antagonist is administered directly into the central nervous system.

E143) The method of any one of E120-E140, wherein said LINGO-2 antagonist is administered systemically.

E144) The method of E120 or E121, comprising (a) transfecting said motor neuron with a polynucleotide which encodes said LINGO-2 antagonist through operable linkage to an expression control sequence, and (b) allowing expression of said LINGO-2 antagonist.

E145) The method of any one of E122-E143, comprising (a) administering, to said mammal a polynucleotide which encodes said LINGO-2 antagonist through operable linkage to an expression control sequence, and (b) allowing expression of said LINGO-2 antagonist.

E146) The method of E145, wherein said polynucleotide is administered as an expression vector.

E146) The method of E145, wherein said expression vector is a viral vector.

E147) The method of E146, wherein the viral vector is selected from the group consisting of an adenoviral vector, an alphavirus vector, an enterovirus vector, a pestivirus vector, a lentivirus vector, a baculovirus vector, a herpesvirus vector, a papovavirus vector, and a poxvirus vector.

E148) The method of any one of E145-E147, wherein said administering comprises (a) providing a cultured host cell comprising said polynucleotide, wherein said cultured host cell expresses said LINGO-2 antagonist; and (b) introducing said cultured host cell into said mammal such that said LINGO-2 antagonist is expressed in said mammal.

E149) The method E148, wherein said cultured host cell is derived from the mammal to be treated.

E150) The method of any one of E146 -E149, wherein said vector is administered by a route selected from the group consisting of topical administration, intraocular administration, parenteral administration, intrathecal administration, subdural administration and subcutaneous administration.

DETAILED DESCRIPTION OF THE INVENTION

I. Definitions

Figure 1:
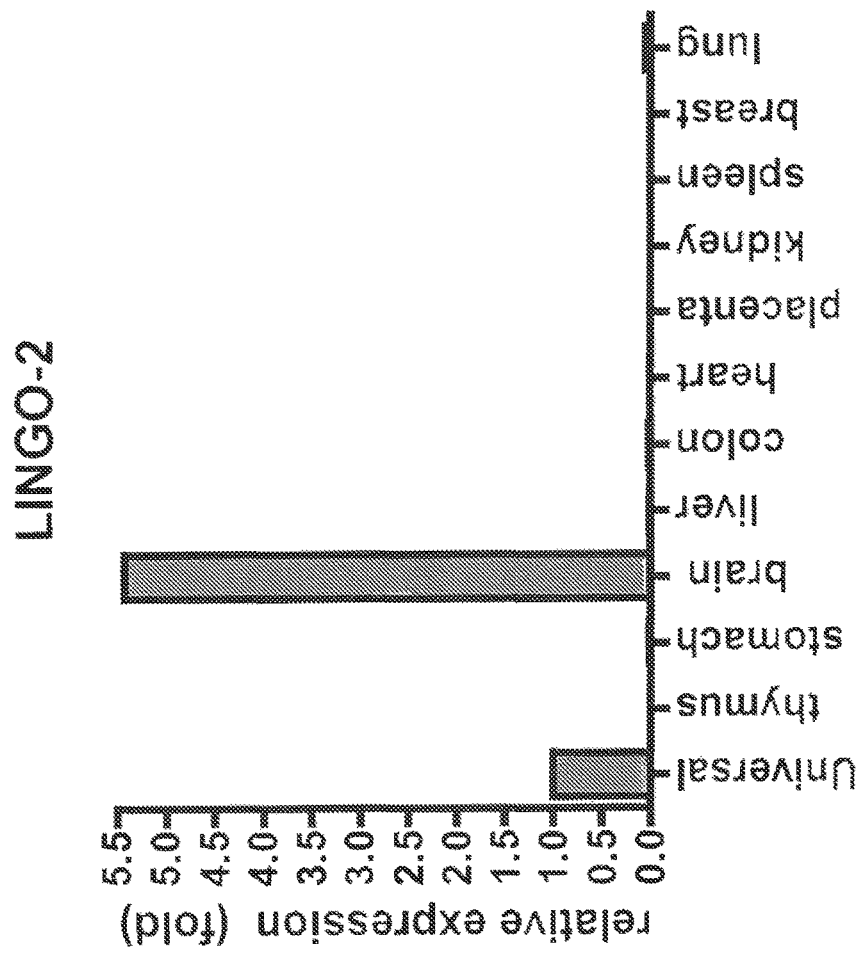
FIG. 1—Q-PCR of rat tissues. LINGO-2 is highly expressed in adult rat brain tissues. Quantitation of mRNA expression of LINGO-2 was carried out by Q-PCR.

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference.

Although methods and materials similar or equivalent to those described herein can be used in practice or testing of the present invention, suitable methods and materials are described below. The materials, methods and examples are illustrative only and are not intended to be limiting. Other features and advantages of the invention will be apparent from the detailed description and from the claims.

In order to further define this invention, the following terms and definitions are provided.

It is to be noted that the term "a" or "an" entity, refers to one or more of that entity. For example, "an immunoglobulin molecule," is understood to represent one or more immunoglobulin molecules. As such, the terms "a" (or "an"), "one or more," and "at least one" can be used interchangeably herein.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide can comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, that has been removed from its native environment. For example, a recombinant polynucleotide encoding an anti-LINGO-2 binding molecule, e.g., an antibody or antigen-binding fragment thereof, contained in a vector is considered isolated. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides. Isolated polynucleotides or nucleic acids further include such molecules produced synthetically. In addition, a polynucleotide or a nucleic acid can be or can include a regulatory element such as a promoter, ribosome binding site, or a transcription terminator. The polynucleotide can be composed of any polyribonucleotide or polydeoxyribonucleotide, which can be unmodified RNA or DNA or modified RNA of DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, the polynucleotides can be composed of triple-stranded regions comprising RNA or DNA or both RNA and DNA. Polynucleotides can also contain one or more modified bases or DNA or RNA backbones modified for stability or for other reasons. "Modified" bases include, for example, tritylated bases and unusual bases such as inosine. A variety of modifications can be made to DNA and RNA. Thus, "polynucleotide" embraces chemically, enzymatically, or metabolically modified forms.

As used herein, a "coding region" is a portion of nucleic acid that consists of codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, introns, and the like, are not part of a coding, region. Two or more coding regions can be present in a single polynucleotide construct, e.g., on a single vector, or in separate polynucleotide constructs, e.g., on separate (different) vectors. Furthermore, any vector can contain a single coding region, or can comprise two or more coding regions, e.g., a single vector can separately encode an immunoglobulin heavy chain variable region and an immunoglobulin light chain variable region. In addition, a vector, polynucleotide, or nucleic acid can encode heterologous coding regions, either fused or unfused to a nucleic acid encoding an anti-LINGO-2 antagonist, e.g., an antibody or fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid that encodes a polypeptide normally can include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region, and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter can be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without, limitation, transcription control regions that function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to, ribosome binding sites, translation initiation and termination codons, and elements derived from picornaviruses (particularly an internal ribosome entry site, or IRES, also referred to as a CITE sequence).

In other embodiments, a polynucleotide is RNA, for example, in the form of messenger RNA (mRNA).

Polynucleotide and nucleic acid coding regions can be associated with additional coding regions that encode secretory or signal peptides, which direct the secretion of a polypeptide encoded by a polynucleotide. According to the signal hypothesis, proteins secreted by mammalian cells have a signal peptide or secretory leader sequence that is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it Alternatively, a heterologous mammalian signal peptide, or a functional derivative thereof, can be used For example, the wild-type leader sequence can be substituted with the leader sequence of human tissue plasminogen activator (TPA) or mouse β-glucuronidase.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide can be derived from a natural biological source or produced by recombinant technology, but is not necessarily translated from a designated nucleic acid sequence. It can be generated in any manner, including by chemical synthesis.

A polypeptide can be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides can have a defined three-dimensional structure, although they do not necessarily have such structure. Polypeptides with a defined three-dimensional structure are referred to as folded, and polypeptides that do not possess a defined three-dimensional structure, but rather can adopt a large number of different conformations, are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated, as are native or recombinant polypeptides that have been separated, fractionated, or partially or substantially purified by any suitable technique.

A polypeptide can be composed of amino acids joined to each other by peptide bonds or modified peptide bonds, i.e., peptide isosteres, and can contain amino acids other than the 20 gene-encoded amino acids (e.g., non-naturally occurring amino acids). Polypeptides can be modified by either natural processes, such as posttranslational processing, or by chemical modification techniques which are well known in the art.

The terms "fragment," "variant," "derivative" and "analog" when referring to a LINGO-2 antagonist include any antagonist molecules that promote survival of motor neurons. These terms also include any antagonist molecules which promote motor neuron axon growth. Soluble LINGO-2 polypeptides can include LINGO-2 proteolytic fragments, deletion fragments and in particular, fragments which more easily reach the site of action when delivered to an animal. Polypeptide fragments further include any portion of the polypeptide which comprises an antigenic or immunogenic epitope of the native polypeptide, including linear as well as three-dimensional epitopes. Soluble LINGO-2 polypeptides can comprise variant LINGO-2 regions, including fragments as described above, and also polypeptides with altered amino acid sequences due to amino acid substitutions, deletions, or insertions. Variants can occur naturally, such as an allelic variant. By an "allelic variant" is intended alternate forms of a gene occupying a given locus on a chromosome of an organism. Genes II, Lewin, B., ed., John Wiley & Sons, New York (1985).

Non-naturally occurring variants can be produced using art-known mutagenesis techniques. Soluble LINGO-2 polypeptides can comprise conservative or non-conservative amino acid substitutions, deletions or additions. LINGO-2 antagonists can also include derivative molecules. For example, soluble LINGO-2 polypeptides can include LINGO-2 regions which have been altered so as to exhibit additional features not found on the native polypeptide. Examples include fusion proteins and protein conjugates.

Conservative substitutions include substitutions within the following groups: valine, alanine and glycine; leucine, valine, and isoleucine; aspartic acid and glutamic acid; asparagine and glutamine; serine, cysteine, and threonine; lysine and arginine; and phenylalanine and tyrosine. The non polar hydrophobic amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Any substitution of one member of the above-mentioned polar, basic or acidic groups by another member of the same group can be deemed a conservative substitution.

Non-conservative substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, Ile, Phe or Trp) is substituted for, or by, one having a smaller side chain (e.g., Ala, Ser) or no side chain (e.g., Gly).

The terms "percent sequence identity" between two polynucleotide or polypeptide sequences refers to the number of identical matched positions shared by the sequences over a comparison window, taking into account additions or deletions (i.e., gaps) that must be introduced for optimal alignment, of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence.

The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences may be accomplished using readily available software both for online use and for download. Suitable software programs are available from various sources, and for alignment of both protein and nucleotide sequences. One suitable program to determine percent sequence identity is b12seq, part of the BLAST suite of program available from the U.S. government's National Center for Biotechnology Information BLAST web site (blast.ncbi.nlm.nih.gov). B12seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, available from www.clustal.org. Another suitable program is MUSCLE, available from www.drive5.com/muscle/. ClustalW2 and MUSCLE are alternatively available, e.g., from the EBI.

It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculated percent sequence identity may be curated either automatically or manually.

The terms "fragment," "variant," "derivative," and "analog" when referring to anti-LINGO-2 antibodies or antibody polypeptides include any polypeptide(s) that retains at least some of the antigen-binding properties of the corresponding antibody or antibody polypeptide. Fragments of polypeptides include proteolytic fragments, as well as deletion fragments, in addition to specific antibody fragments discussed elsewhere herein. Unless it is specifically noted, as used herein a "fragment thereof" in reference to an antibody refers to an immunospecific fragment, i.e., an antigen-specific fragment. Variants of anti-LINGO-2 antibodies and antibody polypeptides include fragments as described above, and also polypeptides with altered amino acid sequences due to amino acid substitutions, deletions, or insertions. Variants can occur naturally or be non-naturally occurring. Variant polypeptides can comprise conservative or non-conservative amino acid substitutions, deletions, or additions. Variant polypeptides can also be referred to herein as "polypeptide analogs." As used herein a "derivative" of an anti-LINGO-2 antibody or antibody polypeptide refers to a subject polypeptide having one or more residues chemically derivatized by reaction of a functional side group. Also included as "derivatives" are those peptides that contain one or more naturally occurring amino acid derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine. Derivatives of anti-LINGO-2 antibodies and antibody polypeptides can include polypeptides that have been altered so as to exhibit additional features not found on the reference antibody or antibody polypeptide.

A "polypeptide fragment" refers to a short amino acid sequence of a polypeptide. Protein fragments can be "free-standing," or comprised within a larger polypeptide of which the fragment forms a part of region. Representative examples of polypeptide fragments include, for example, fragments comprising about 5 amino acids, about 10 amino acids, about 15 amino acids, about 20 amino acids, about 30 amino acids, about 40 amino acids, about 50 amino acids, about 60 amino acids, about 70 amino acids, about 80 amino acids, about 90 amino acids, about 100 amino acids, about 200 amino acids, about 300 amino acids, about 400 amino acids, about 500 amino acids, about 600 amino acids, and about 1,000 amino acids in length.

A "binding molecule" or "antigen-binding molecule" refers in its broadest sense to a molecule that specifically binds an antigenic determinant. In one embodiment, the binding molecule specifically binds to LINGO-2, e.g., fall length LINGO-2 or mature LINGO-2. In another embodiment, a binding molecule is an antibody or an antigen-binding fragment thereof.

Anti-LINGO-2 antibodies, or antigen-binding fragments, variants, and derivatives thereof are described herein. Unless specifically referring to full-sized antibodies such as naturally occurring antibodies, the term "anti-LINGO-2 antibodies" encompasses full-sized antibodies as well as antigen-binding fragments, variants, analogs, or derivatives of such antibodies, e.g., naturally occurring antibody or immunoglobulin molecules or engineered antibody molecules or fragments that bind antigen in a manner similar to antibody molecules.

In certain embodiments, amino acid substitutions are conservative amino acid substitution. Alternatively, mutations can be introduced randomly along all or part of the coding sequence, such as by saturation mutagenesis, and the resultant mutants can be screened for biological activity to identify mutants that retain activity (e.g., the ability to bind a LINGO-2 polypeptide, e.g., human, primate, murine, or any combination of human, primate and murine LINGO-2). Such variants (or derivatives thereof) of "human" or "fully human" antibodies can also be referred to as human or fully human antibodies that are "optimized" or "optimized for antigen-binding" and include antibodies that have improved affinity to antigen.

In one embodiment, the LINGO-2 antagonists are "antibody" or "immunoglobulin" molecules, or antigen-binding fragments thereof, e.g., naturally occurring antibody or immunoglobulin molecules or engineered antibody molecules or fragments that bind antigen in a manner similar to antibody molecules. The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988).

In naturally occurring antibodies, the six "complementarity determining regions" or "CDRs" present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see, "Sequences of Proteins of Immunological Interest," Kabat, E., et al., U.S. Department of Health and Human Services, (1983); and Chothia and Lesk, J. Mol. Biol., 196:901-917 (1987), which are incorporated herein by reference in their entireties).

In the case where there are two or more definitions of a term that are used and/or accepted within the art, the definition of the term as used herein is intended to, include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al. (1983) U.S. Dept. of Health and Human Services, "Sequences of Proteins of Immunological Interest" and by Chothia and Lesk, *J. Mol. Biol.* 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues that encompass the CDRs as defined by each of the above cited references are set forth below in Table 1 as a comparison. The exact residue numbers that encompass a particular CDR can vary depending on the sequence and size of the CDR. Those skilled in the art can routinely determine which residues comprise a particular CDR given the variable region amino acid sequence of the antibody.

TABLE 1

| CDR Definitions[1] | | |
|---|---|---|
| | Kabat | Chothia |
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on, any experimental data beyond the sequence itself. As, used herein, "Kabat numbering" refers to the numbering system set forth by Kabat et al. U.S. Dept. of Health and Human Services, "Sequence of Proteins of Immunological Interest" (1983). Unless otherwise specified, references to the numbering of specific amino acid residue positions in a LINGO-2 antibody or antigen-binding, fragment, variant, or derivative thereof are according to the Kabat numbering system.

In one embodiment, an antigen-binding molecule comprises at least one heavy or light chain CDR of a reference antibody molecule. In another embodiment, an antigen-binding molecule comprises at least, two CDRs from one or more reference antibody molecules. In another embodiment, an antigen-binding molecule comprises at least three CDRs from one or more reference antibody molecules. In another embodiment, an antigen-binding molecule comprises at least four CDRs from one or more reference antibody molecules. In another embodiment, an antigen-binding molecule comprises at least five CDRs from one or more reference antibody molecules. In another embodiment, an antigen-binding molecule comprises at least six CDRs from one or more reference antibody molecules. In certain embodiments the reference antibody molecule is C09. Exemplary antibody molecules comprising, at least one CDR that can be included in the subject antigen-binding molecules are known in the art and exemplary molecules are described herein.

Unless specifically referring to full-sized antibodies such as naturally occurring antibodies, the term "anti-LINGO-2 antibodies" encompasses full-sized antibodies as well as antigen-binding fragments, variants, analogs, or derivatives of such antibodies, e.g., naturally occurring antibody or immunoglobulin molecules or engineered antibody molecules or fragments that bind antigen in a manner similar to antibody molecules.

Antibodies or antigen-binding fragments thereof include, but are not limited to, polyclonal, monoclonal, multispecific, human, humanized, primatized, or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a $V_L$ or $V_H$ domain, fragments produced by a Fab expression library, and anti-idiotypic (anti-Id) antibodies (including, e.g., anti-Id antibodies to binding molecules disclosed herein). ScFv molecules are known in the art and are described, e.g., in U.S. Pat. No. 5,892,019. Immunoglobulin or antibody molecules can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass of immunoglobulin molecule.

Antibody fragments, including single-chain antibodies, can comprise the variable region(s) alone or in combination with the entirety or a portion of the following: hinge region, $C_H1$, $C_H2$, and $C_H3$ domains. Also provided herein are antigen-binding fragments also comprising any combination of variable region(s) with a hinge region, $C_H1$, $C_H2$, and $C_H3$ domains. Antibodies or antigen-binding fragments thereof can be from any animal origin, including birds and mammals. In certain embodiments, the antibodies are human, murine, donkey, rabbit, goat, guinea pig, camel, llama, horse, or chicken antibodies. In another embodiment, the variable region can be condricthoid in origin (e.g., from sharks).

As used herein, the term "heavy chain portion" includes amino acid sequences derived from an immunoglobulin heavy chain. A polypeptide comprising a heavy chain portion comprises at least one of a $C_H1$ domain, a hinge (e.g., upper, middle, and/or lower hinge region) domain, a $C_H2$ domain, a $C_H3$ domain, or a variant or fragment thereof For example, a binding polypeptide can comprise a polypeptide chain comprising a $C_H1$ domain; a polypeptide chain comprising a $C_H1$ domain, at least a portion of a hinge domain, and a $C_H2$ domain; a polypeptide chain comprising a $C_H1$ domain and a $C_H3$ domain, a polypeptide chain comprising a $C_H1$ domain; at least a portion of a hinge domain, and a $C_H3$ domain, or a polypeptide chain comprising a $C_H1$ domain, at least a portion of a hinge domain, a $C_H2$ domain, and a $C_H3$ domain. In another embodiment, a polypeptide comprises a polypeptide chain comprising a $C_H3$ domain. Further, a binding polypeptide can lack at least a portion of a $C_H2$ domain (e.g., all or part of a $C_H2$ domain). As set forth above, it will be understood by one of ordinary skill in the art that these domains (e.g., the heavy chain portions) can be modified such that they vary in amino acid sequence from the naturally occurring immunoglobulin molecule. The heavy chain portions of a binding polypeptide can be derived from different immunoglobulin molecules. For example, a heavy chain portion of a polypeptide can comprise a $C_H1$ domain derived from an $IgG_1$ molecule and a hinge region derived from an $IgG_3$ molecule. In another example, a heavy chain portion can comprise a hinge region derived, in part, from an $IgG_1$ molecule and, in part, from an $IgG_3$ molecule. In another example, a heavy chain portion can comprise a chimeric hinge derived, in part, from an $IgG_1$ molecule and, in part, from an $IgG_4$ molecule.

As used herein, the term "light chain portion" includes amino acid sequences derived from an immunoglobulin light chain. Typically, the light chain portion comprises at least one of a VL or CL domain.

Anti-LINGO-2 antibodies, or antigen-binding fragments, variants, or derivatives thereof disclosed herein can be described or specified in terms of the epitope(s) or portion(s) of an antigen, e.g., a target polypeptide disclosed herein (e.g., full length or mature LINGO-2) that they recognize or specifically bind. The portion of a target polypeptide that specifically interacts with the antigen-binding domain of an antibody is an "epitope," or an "antigenic determinant." A target polypeptide can comprise a single epitope, but typically comprises at least two epitopes, and can include any number of epitopes, depending on the size, conformation, and type of antigen. Furthermore, it should be noted that an "epitope" on a target polypeptide can be or can include non-polypeptide elements, e.g., an epitope can include a carbohydrate side chain.

The minimum size of a peptide or polypeptide epitope for an antibody is thought to be about four to five amino acids. Peptide or polypeptide epitopes can contain at least seven, at least nine, or at least about 15 to about 30 amino acids. Since a CDR can recognize an antigenic peptide or polypeptide in its tertiary form, the amino acids comprising an epitope need not be contiguous, and in some cases, can not even be on the same peptide chain. A peptide or polypeptide epitope recognized by anti-LINGO-2 antibodies can contain a sequence of at least 4, at least 5, at least 6, at least 7, at least 8, at least 9, at least 10, at least 15, at least 20, at least 25, or between about 15 to about 30 contiguous or non-contiguous amino acids of LINGO-2.

By "specifically binds," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" can be deemed to have a higher specificity for a given epitope than, antibody "B," or antibody "A" can be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody that "preferentially binds" to a given epitope would more likely bind to that epitope than to a related epitope, even though such an antibody can cross-react with the related epitope.

By way of non-limiting example, an antibody can be considered to bind a first epitope preferentially if it binds said first epitope with a dissociation constant ($K_D$) that is less than the antibody's $K_D$ for the second epitope. In another non-limiting example, an antibody can be considered to bind a first antigen preferentially if it binds the first epitope with an affinity that is at least one order of magnitude less than the antibody's $K_D$ for the second epitope. In another non-limiting example, an antibody can be considered to bind a first epitope preferentially if it binds the first epitope with an affinity that is at least two orders of magnitude less than the antibody's $K_D$ for the second epitope.

In another non-limiting example, an antibody can be considered to bind a first epitope preferentially if it binds the first epitope with an off rate (k(off)) that is less than the antibody's k(off) for the second epitope. In another non-limiting example, an antibody can be considered to bind a first epitope preferentially if it binds the first epitope with an affinity that is at least one order of magnitude less than the antibody's k(off) for the second epitope. In another non-limiting example, an antibody can be considered to bind a first epitope preferentially if it binds the first epitope with an affinity that is at least two orders of magnitude less than the antibody's k(off) for the second epitope. An antibody or antigen-binding fragment, variant, or derivative thereof disclosed herein can be said to bind a target polypeptide disclosed herein (e.g., LINGO-2, e.g., human, primate, murine, or any combination of human, primate and murine LINGO-2) or a fragment or variant thereof with an off rate (k(off)) of less than or equal to $5 \times 10^{-2}$ sec$^{-1}$, $10^{-2}$ sec$^{-1}$, $5 \times 10^{-3}$ sec$^{-1}$ or $10^{-3}$ sec$^{-1}$. An antibody can be said to bind a target polypeptide disclosed herein (e.g., LINGO-2, e.g., human, primate, murine, or any combination of human, primate and murine LINGO-2) or a fragment or variant thereof with an off rate (k(off)) less than or equal to $5 \times 10^{-4}$ sec$^{-1}$, $10^{-4}$ sec$^{-1}$, $5 \times 10^{-5}$ sec$^{-1}$, or $10^{-5}$ sec$^{-1}$, $5 \times 10^{-6}$ sec$^{-1}$, $10^{-6}$ sec$^{-1}$, $5 \times 10^{-7}$ sec$^{-1}$ or $10^{-7}$ sec$^{-1}$.

An antibody or antigen-binding fragment, variant, or derivative thereof disclosed herein can be said to bind a target polypeptide disclosed herein (e.g., LINGO-2, e.g., human, primate, murine, or any combination of human, primate and murine LINGO-2) or a fragment or variant thereof with an on rate (k(on)) of greater than or equal to $10^3$ M$^{-1}$ sec$^{-1}$, $5 \times 10^3$ M$^{-1}$ sec$^{-1}$, $10^4$ M$^{-1}$ sec$^{-1}$ or $5 \times 10^4$ M$^{-1}$ sec$^{-1}$. An antibody can bind a target polypeptide disclosed herein (e.g., LINGO-2, e.g., human, primate, murine, or any combination of human, primate and murine LINGO-2) or a fragment or variant thereof with an on rate (k(on)) greater than or equal to $10^5$ M$^{-1}$ sec$^{-1}$, $5 \times 10^5$ M$^{-1}$ sec$^{-1}$, $10^6$ M$^{-1}$ sec$^{-1}$, or $5 \times 10^6$ M$^{-1}$ sec$^{-1}$ or $10^7$ M$^{-1}$ sec$^{-1}$.

An antibody is said to competitively inhibit binding of a reference antibody to a given epitope if it preferentially binds to that epitope to the extent that it blocks, to some degree, binding of the reference antibody to the epitope. Competitive inhibition can be determined by any method known in the art, for example, competition ELISA assays. An antibody can be said to competitively inhibit binding of the reference antibody to a given epitope by at least 90%, at least 80%, at least 70%, at least 60%, or at least 50%.

As used herein, the, term "affinity" refers to a measure of the strength of the binding of an individual epitope with the CDR of an immunoglobulin molecule. See, e.g., Harlow et al. (1988) Antibodies: A Laboratory Manual (Cold Spring Harbor Laboratory Press, 2nd ed.) pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Anti-LINGO-2 antibodies or antigen-binding fragments, variants, or derivatives thereof can also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, can actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody can be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody can be deemed "highly specific" for a certain epitope, if it does not bind any other analog, ortholog, or homolog of that epitope.

As previously indicated, the subunit structures and three dimensional configuration of the constant regions of the various immunoglobulin classes are well known. As used herein, the term "VH domain" includes the amino terminal variable domain of an inimunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al.). The CH2 domain is unique in that it is not closely paired with another domain. Rather. two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., J. Immunol. 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" includes any antibody wherein the immunoreactive region or site is obtained or derived from a first species and the constant region (which can be intact, partial or modified in accordance with the instant invention) is obtained from a second species. In certain embodiments the target binding region or site will be from a non-human source (e.g., mouse or primate) and the constant region is human.

As used herein, "human" or "fully human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example, in U.S. Pat. No 5,939,598 by Kucherlapati et al. "Human" or "fully human" antibodies also include antibodies comprising at least the variable domain of a heavy chain, or at least the variable domains of a heavy chain and a light chain, where the variable domain(s) have the amino acid sequence of human immunoglobulin variable domain(s). "Human" or "fully human" antibodies also include "human" or "fully human" antibodies, as described above, that comprise, consist essentially of, or consist of, variants (including derivatives) of antibody molecules (e.g., the $V_H$ regions and/or $V_L$ regions) described herein, which antibodies or antigen-binding fragments, variants, or derivatives thereof immunospecifically bind to a LINGO-2 polypeptide or fragment or variant thereof.

Standard techniques known to those of skill in the art can be used to introduce mutations in the nucleotide sequence encoding a human anti-LINGO-2 antibody, including, but not limited to, site-directed mutagenesis and PCR-mediated mutagenesis which result in amino acid substitutions. The variants (including derivatives) can encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference $V_H$ region, $V_H$CDR1, $V_H$CDR2, $V_H$CDR3, $V_L$ region, $V_L$CDR1, $V_L$CDR2, or $V_L$CDR3. In one embodiment, one or more cysteine residues present in a CDR of an antibody is changed to a different amino acid residue.

As used herein, the term "engineered antibody" refers to an antibody in which the variable domain in either the heavy and light chain or both is altered by at least partial replacement of one or more CDRs from an antibody of known specificity and, if necessary, by partial framework region replacement and sequence changing. Although the CDRs can be derived from an antibody of the same class or even subclass as the antibody from which the framework regions are derived, it is envisaged that the CDRs will be derived from an antibody of different class and/or an antibody from a different species. An engineered antibody in which one or more "donor" CDRs from a non-human antibody of known specificity is grafted into a human heavy or light chain framework region is referred to herein as a "humanized antibody." In certain embodiments, it is not necessary to replace all of the CDRs with the complete CDRs from the donor variable region to transfer the antigen-binding capacity of one variable domain to another. Rather, it can be sufficient to transfer those residues that are necessary to maintain the activity of the target binding site. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

It is further recognized that the framework regions within the variable domain in a heavy or light chain, or both, of a humanized antibody can comprise solely residues of human origin, in which case these framework regions of the humanized antibody are referred to as "fully human framework regions." Alternatively, one or more residues of the framework region(s) of the donor variable domain can be engineered within the corresponding position of the human framework region(s) of a variable domain in a heavy or light chain, or both, of a humanized antibody if necessary to maintain proper binding or to enhance binding to the LINGO-2 antigen. A human framework region that has been engineered in this manner would thus comprise a mixture of human and donor framework residues, and is referred to herein as a "partially human framework region."

For example, humanization of an anti-LINGO-2 antibody can be essentially performed following, the method of Winter and co-workers (Jones et al., Nature 321:522-525 (1986); Riechmann et al., Nature 332:323-327 (1988); Verhoeyen et al., Science 239:1534-1536 (1988)), by substituting rodent or mutant rodent anti-LINGO-2 CDRs or CDR sequences into the corresponding sequences of a human antibody. See also U.S. Pat. Nos. 5,225,539; 5,585,089; 5,693,761; 5,693,762; 5,859,205; herein incorporated by reference. The resulting humanized anti-LINGO-2 antibody would comprise at least one rodent or mutant rodent CDR within the fully human framework regions of the variable domain of the heavy and/or light chain of the humanized antibody. In some instances, residues within the framework regions of one or more variable domains of the humanized anti-LINGO-2 antibody are replaced by corresponding non-human (for example, rodent) residues (see, for example, U.S. Pat. Nos. 5,585,089; 5,693,761; 5,693,762; and 6,180, 370), in which case the resulting humanized anti-LINGO-2 antibody would comprise partially human framework regions within the variable domain of the heavy and/or light chain.

Furthermore, humanized antibodies can comprise residues that are not found in the recipient antibody or in the donor antibody. These modifications are made to further refine antibody performance (e.g., to obtain desired affinity).

In general, the humanized antibody will comprise substantially all of at least one, and typically two, variable domains, in which all or substantially all of the CDRs correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al., *Nature* 331:522-525 (1986); Riechmann et al., *Nature* 332:323-329 (1988); and Presta, *Curr. Op. Struct. Biol.* 2:593-596 (1992); herein incorporated by reference. Accordingly, such "humanized" antibodies can include antibodies wherein substantially less than an intact human variable, domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225,539; 5,585,089; 5,693,761; 5,693,762; 5,859,205. See also U.S. Pat. No. 6,180,370, and International Publication No. WO 01/27160, where humanized antibodies and techniques for producing humanized antibodies having improved affinity for a predetermined antigen are disclosed.

As used herein, the terms "linked," "fused" or "fusion" are used interchangeably. These terms refer to the joining together of two more elements or components, by whatever means including chemical conjugation or recombinant means. An "in-frame fusion" refers to the joining of two or more open reading frames (ORFs) to form a continuous longer ORF, in a manner that maintains the correct reading frame of the original ORFs. Thus, the resulting recombinant fusion protein is a single protein containing two or more segments that correspond to polypeptides encoded by the original ORFs (which segments are not normally so joined in nature.) Although the reading frame is thus made continuous throughout the fused segments, the segments can be physically or spatially separated by, for example, in-frame linker sequence.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

The term "expression" as used herein refers to a process by which a gene produces a biochemical, for example, an RNA or polypeptide. The process includes any manifestation of the functional presence of the gene within the cell including, without limitation, gene knockdown as well as both transient expression and stable expression. It includes without limitation transcription of the gene into messenger RNA (mRNA), transfer RNA (tRNA), small hairpin RNA (shRNA), small interfering RNA (siRNA) or any other RNA product and the translation of such mRNA into polypeptide(s). If the final desired product is biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, a "therapeutically effective amount" refers to an amount effective, at dosages and for periods of time necessary, to achieve a desired therapeutic result. A therapeutic result can be, e.g., lessening of symptoms, prolonged survival, improved mobility, and the like. A therapeutic result need not be a "cure."

As used herein, a "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

As used herein, the terms "treat" or "treatment" refer to both therapeutic treatment and prophylactic or preventative measures, wherein the object is to prevent or slow down (lessen) an undesired physiological change or disorder, such as the progression of an autoimmune condition. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as guinea pigs, rabbits, rats, and mice, primates such as apes, monkeys, orangutans, and chimpanzees, canids such as dogs and wolves, felids such as cats, lions, and tigers, equids such as horses, donkeys, and zebras, food animals such as cows, pigs, and sheep, ungulates such as deer and giraffes, bears, and so on. In certain embodiments, the mammal is a human subject.

As used herein, phrases such as "a subject that would benefit from administration of a LINGO-2 antagonist" and "an animal in need of treatment" includes subjects, such as mammalian subjects, that would benefit from administration of a LINGO-2 antagonist used, e.g., for detection of an anti-LINGO-2 polypeptide (e.g., for a diagnostic procedure) and/or from treatment, i.e., palliation or prevention of a disease such as ALS, with a LINGO-2 antagonist such as an anti-LINGO-2 antibody.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene can be endogenous or exogenous to the organism, present integrated into a chromosome or present in a transfection vector that is not integrated into the genome. The expression of the gene is either completely or partially inhibited. RNAi can also be considered to inhibit the function of a target RNA; the function of the target RNA can be complete or partial.

II. LINGO-2

LINGO-2 is expressed in cortex neurons and dorsal root ganglion (DRG) and negatively regulates motor neuron survival and motor neuron axon growth.

Naturally occurring human LINGO-2 is a polypeptide of 606 amino acids. The polynucleotide encoding the human LINGO-2 mRNA is reported as accession number NM_152570 in GenBank:

(SEQ ID NO: 1)
```
aatttagaga agatgtaggg agtgttcaac atgttcgttg
tggaagagaa agagctaaga gagaggagct taaagacaca
aacgggtaga atcaaggagt gtgctctcaa atgagaggaa
caggagtgac attaaccttg aaatgctcgg agactctact
ccttcatgac agtaggagga taattaacaa tagatacaaa
tgcaggaatt gatgagtgcc atcagaaagc tgtatcatga
gctgcctgca cttctaaagt gtccagtgga tttttaatca
catgagcctg gaaatagggt tatgaaaaga agctcagagc
agagcaccga aagtggccac taccagcatg aagagcccaa
caattcaaac tggtgaagtg agaaaaacag aatgcagctt
tcaaggttcg tttcaagcag ttggcttgtg ggactctgag
agatgctgct gcccatgaca tgcgggaatt atcatgatca
actacccagc ttggatttca tccagtggcc aagagctttg
tgtgggagac ggcaagggtt ggattttca aaagagtaaa
ccaggataaa tcatgaggaa cctataaccc ttttggccac
atgcaaaaaa gcaagaccg tgaccaaggt gtagactaag
aagtggagtc atgcttcaca cggccatatc atgctggcag
ccattcctgg gtctggctgt ggtgttaatc ttcatgggat
ccaccattgg ctgccccgct cgctgtgagt gctctgccca
gaacaaatct gttagctgtc acagaaggcg attgatcgcc
atcccagagg gcattcccat cgaaaccaaa atcttggacc
tcagtaaaaa caggctaaaa agcgtcaacc ctgaagaatt
catatcatat cctctgctgg aagagataga cttgagtgac
aacatcattg ccaatgtgga accaggagca ttcaacaatc
tctttaacct gcgttccctc cgcctaaaag gcaatcgtct
aaagctggtc cctttgggag tattcacggg gctgtccaat
ctcactaagc ttgacattag tgagaataag attgtcattt
tactagacta catgttccaa gatctacata acctgaagtc
tctagaagtg ggggacaatg atttggttta tatatcacac
agggcattca gtgggcttct tagcttggag cagctcaccc
tggagaaatg caacttaaca gcagtaccaa cagaagccct
ctcccacctc cgcagcctca tcagcctgca tctgaagcat
ctcaatatca acaatatgcc tgtgtatgcc tttaaagat
tgttccacct gaaacaccta gagattgact attggccttt
actggatatg atgcctgcca atagcctcta cggtctcaac
ctcacatccc tttcagtcac caacaccaat ctgtctactg
taccctttcct tgcctttaaa cacctggtat acctgactca
ccttaacctc tcctacaatc ccatcagcac tattgaagca
ggcatgttct ctgacctgat ccgccttcag gagcttcata
tagtgggggc ccagcttcgc accattgagc ctcactcctt
ccaagagctc cgcttcctac gcgtgctcaa tgtgtctcag
aacctgctgg aaactttgga agagaatgtc ttctcctccc
ctagggctct ggaggtcttg agcattaaca caaccctct
ggcctgtgac tgccgccttc tctgaatctt gcagcgacag
cccacccgc agtttggtgg ccagcaacct atgtgtgctg
gcccagacac catccgtgag aggtctttca aggatttcca
tagcactgcc cttcttttt actttacctg caaaaaaccc
aaaatccgtg aaaagaagtt gcagcatctg ctagtagatg
aagggcagac agtccagcta gaatgcagtg cagatggaga
cccgcagcct gtgatttcct gggtgacacc ccgaaggcgt
ttcatcacca ccaagtccaa tggaagagcc accgtgttgg
gtgatggcac cttggaaatc cgctttgccc aggatcaaga
cagcgggatg tatgtttgca tcgctagcaa tgctgctggg
aatgatacct tcacagcctc cttaactgtg aaaggattcg
cttcagatcg ttttctttat gcgaacagga cccctatgta
catgaccgac tccaatgaca ccatttccaa tggcaccaat
gccaatactt tttccctgga ccttaaaaca atactggtgt
ctacagctat gggctgcttc acattcctgg gagtggtttt
attttgtttt cttctccttt ttgtgtggag ccgagggaaa
ggcaagcaca aaaacagcat tgaccttgag tatgtgccca
gaaaaaacaa tggtgctgtt gtggaaggag aggtagctgg
acccaggagg ttcaacatga aaatgatttg aaggcccacc
cctcacatta ctgtctcttt gtcaatgtgg gtaatcagta
agacagtatg gcacagtaaa ttactagatt aagaggcagc
catgtgcagc tgcccctgta tcaaaagcag ggtctatgga
agcaggagga cttccaatgg agactctcca tcgaaaggca
ggcaggcagg catgtgtcag agcccttcac acagtgggat
actaagtgtt tgcgttgcaa atattggcgt tctggggatc
tcagtaatga acctgaatat ttggctcaca ctcacggaca
attattcagc attttctacc actgcaaaaa ac.
```

The polypeptide sequence of human LINGO-2 (encoded by nucleotides 651 to 2471 of SEQ ID NO:1) is reported as accession number NP_689783 in GenBank:

(SEQ ID NO: 2)
MLHTAISCWQPFLGLAVVLIFMGSTIGCPARCECSAQNKSVSCHRRRLI
AIPEGIPIETKILDLSKNRLKSVNPEEFISYPLLEEIDLSDNIIANVEP
GAFNNLFNLRSLRLKGNRLKLVPLGVFTGLSNLTKLDISENKIVILLDY
MFQDLHNLKSLEVGDNDLVYISHRAFSGLLSLEQLTLEKCNLTAVPTEA

LSHLRSLISLHLKHLNINNMPVYAFKRLFHLKHLEIDYWPLLDMMPANS

LYGLNLTSLSVTNTNLSTVPFLAFKHLVYLTHLNLSYNPISTIEAGMFS

DLIRLQELHIVGAQLRTIEPHSFQGLRFLRVLNVSQNLLETLEENVFSS

PRALEVLSINNNPLACDCRLLWILQRQPTLQFGGQQPMCAGPDTIRERS

FKDFHSTALSFYFTCKKPKIREKKLQHLLVDEGQTVQLECSADGDPQPV

ISWVTPRRRFITTKSNGRATVLGDGTLEIRFAQDQDSGMYVCIASNAAG

NDTFTASLTVKGFASDRFLYANRTPMYMTDSNDTISNGTNANTFSLDLK

TILVSTAMGCFTFLGVVLFCFLLLFVWSRGKGKHKNSIDLEYVPRKNNG

AVVEGEVAGPRRFNMKMI.

The polynucleotide encoding the mouse LINGO-2 mRNA is reported as accession number NM_175516.4 in GenBank:

(SEQ ID NO: 3)

```
gccagtgcac tctagaaacc cagcctgcat gtagaaagcc
ctgtctactg cagaagatga ttcctgcccc gggttaaatg
tgcacaactc gcggaaatgc cagtaccttc cacctgaagg
cacttagtgg ctagaaaacc agcaatctac cccgaaacac
actgtactaa acacagcaag agaccacaat gattggacat
atacctatga agatccactt tgagaaagat gccagttgtt
ccacaggatg cactttgaga atgaattcat tctagctggt
acagcaaaag gagtgcatta aggcccgtaa ccaaggtgta
gacaaagaag tggagtcatg cttcacacgg ctataccatg
ctggcagcca ttcctgggtc tggctgtggt gttactctta
atgggatcca ccattggctg tcctgctcgc tgtgagtgct
ccgcccagaa caaatctgtt agctgccaca gaagacgatt
gctcgcgatc ccagaaggca ttcccattga gaccaaaatc
ttggacctga gcaaaaatcg actaaagagc ataaaccctg
aagagttcat ctcatatcct ctgttggagg agatagactt
gagcgacaac attattgcca atgtggagcc tggggcattt
aacaatctct ttaacctgcg ttccctccgc ctaaaaggca
atcgccttaa gttggtccct ttaggagtat tcacaggact
gtccaacctc accaagcttg acattagtga gaataagatt
gtcattttgc tggactacat gttccaggat ctgcataacc
tgaagtctct agaagtgggg gacaatgatt tagtgtatat
ctcacacagg gccttcagcg gactacttag cttggagcag
ctcaccctgg agaagtgcaa cttgacagca gtaccaacag
aagcccttc ccatctccgc agcctcatcg ccctgcatct
gaagcatctc aatatcaaca atatgcctgt gtatgccttt
aaaagattgt tccacctgaa aaacctagag atcgactatt
ggcctttgtt ggatttgatg ccagccaaca gcctctatgg
tctcaacctc acgtcccttt caatcaccaa caccaacctg
```

```
tccactgtcc ccttcctcgc cttaaaacac cttgtatacc
tgacccacct taacctctcc tacaatccca tcagcactat
tgaagctggc atgttctctg acctgatccg cctacaggag
cttcatatag tgggggccca gctccgcact attgagcctc
actccttcca agggctccgc ttcctccgtg tgctcaatgt
atctcagaac ctgctggaaa cattggaaga aacgtcttc
tcctccccta gggctttgga ggtcctgagc attaacaaca
acccactagc ctgtgactgc cgactcctct ggctcctgca
gcgacaaccc aacctgcagt ttgggggcca gcagcccatg
tgtgctgggc cagacaccat ccgtgagaga tcatttaagg
atttccatag cactgctctt tcttttatt ttacctgcaa
aaaacccaaa atccgtgaaa agaagttaca gcatctcctc
gtggatgaag ggcaaacggt ccagctggag tgcaacgctg
atggagaccc gcagcccgtg atttcctggg tgacacctcg
aaggcgtttt atcaccacca agtccaacgg aagggccact
gtgttgggtg atggcacctt ggaaatccgt tttgcccagg
atcaagacag tgggatgtat gtttgcatcg cgagcaacgc
tgctgggaac gataccttca cagcatctct cactgtgaag
ggattcacgt cagaccgctt cctttacgca aacaggaccc
ctatgtacat gactgactcc aacgacaccg tttccaacgg
cactaatgcc aatactttct ccctggacct aaaaacaata
ctggtatcta cagccatggg ctgtttcaca ttcctgggag
tggttttatt ttgttttctc cttcttttg tgtggagccg
agggaaaggc aagcacaaaa acagcattga ccttgagtat
gtgccccgaa aaaacaatgg tgctgttgtg gaaggggagg
tggctggccc caggaggttc aacatgaaaa tgatctaagg
gcccaccaca cactactgtc tctctgttac tgttggtcgt
gagtaagacg tctgatagag tgactcgatc acaaggttat
cgggcagctt tgcgcagctg cccctgtgtc aaagcagggt
ccatggaagc aggaagactt ctcatggaga ctggctgatt
agaggcaggc aggcatgtgt cagagccctt cacacagtgg
gatactaatt gttgcattg caaatattgg cattctgggg
atctcagcaa tgaacctgaa cctttggctc atgctgatgg
acaataattc aacattttct accactgcaa aactaaaagg
aaaaaaaatt aaaaagaaca acctacagtg taggatttac
atattaaaaa gacacatttg tctaaaacat actctacagt
caaatttgta tttattatca tttgttaaaa ccttgcatca
tacaatactg ttggttcagc accaaaaaga gatcaatata
ttctttttt tgaaacatat atgctgtata tgttttaaag
caatatgaat gagaggttgt gcttttagtt actcaccagt
```

```
atagatccaa gtgtggtttc accttccttt tacctgcaga taaacctgag aatagatccc tggaatacta ggcagagatg tgttgagatg tgtatgtctg atgtaggatg ccaagaaaca agacccaagt caaaactgct caactctgtt aacttctgtt actataaata aaggcatgtg cctagttttg atacagaatg gaatattttt tatacataca ctaccaacct ggaccagttt actgtaacag aagcccttgg tttctccaga aggcggtaca tcgctagggg tacctataga atacaaggta ggtgtcactc ttaaaagtaa tccatgtagc tactgcttag ttttactttc gccagtcact gctaatgggt taatgaccaa tggaaaagag aatattgatt atatagaatt atttggcaat attcaccaat agctaatatc aataattctg ttgtccgaaa gccctctgaa taaggaggtt tcagaagtca ataggaagca gggagagaca agagcatcac agcagcgatt cagccaatga tctctttcaa atgtggcagc tgcctgccgg atggctacaa atcaaaggga atacgctgca catgccagcc caacttctat ccaagtacta tacacagagt aggaccacag ttaggcaact tcaggatatt cctctgcttc ctgatcaaga tctttagttt catattgaaa accatattac acagctacga ggaatatgtt ttgtgtgaaa gaagtaaaag tagtgaaaga aaaaccaata tagatctaaa aaacaatgtt ttgttccttc actggggaag agctaagctt atagttctac aaatatgtaa tgctgtgcca attcttttac cttcttgacc tgagcatatt tgcccaatta agttgatatt aatgttacta atgcaaacat aaccagaaa.
```

The polypeptide sequence of mouse LINGO-2 is reported as accession number NP_780725 in GenBank:

```
                                           (SEQ ID NO: 4)
mlhtaipcwq pflglavvll lmgstigcpa rcecsaqnks vschrrrlla ipegipietk ildlsknrlk sinpeefisy plleeidlsd niianvepga fnnlfnlrsl rlkgnrlklv plgvftglsn ltkldisenk ivilldymfq dlhnlkslev gdndlvyish rafsgllsle qltlekcnlt avptealshl rslialhlkh lninnmpvya fkrlfhlknl eidywplldl mpanslygln ltslsitntn lstvpflafk hlvylthlnl synpistiea gmfsdlirlq elhivgaqlr tiephsfqgl rflrvlnvsq nlletleenv fsspralevl sinnnplacd crllwllqrq pnlqfggqqp mcagpdtire rsfkdfhsta lsfyftckkp kirekklqhl lvdegqtvql ecnadgdpqp viswvtprrr fittksngra tvlgdgtlei rfaqdqdsgm yvciasnaag ndtftasltv kgftsdrfly anrtpmymtd
```

```
sndtvsngtn antfsidlkt ilvstamgcf tflgvvlfcf lllfvwsrgk gkhknsidle yvprknngav vegevagprr fnmkmi.
```

The polynucleotide encoding the rat LINGO-2 mRNA is reported as accession number NM_001107926.1 in GenBank:

```
                                           (SEQ ID NO: 5)
gtgccagggc actctagaaa cccagcctgc atgtagacag ccctgcctac tgcagaagat gattcctgcc ccgggttaaa cgtgtacaac tcgtggaaat gccagtacct tccacctgaa ggcacttagt ggctagaaaa ccagcaatct accccgaaac acactgtact aaacacagca agagaccaca atgattggac atagacctat aaggatacac tttgagaaag atgccagttg ttcctcagga tgcactttga aaatgcagtc attctagctg gtaccgcaaa atgagtgcat taaggcccat aaccaaggtg tagaataaac agtggagtca tgcttcacac ggctatacca tgctggcagc cattcctggg tctggctatg gtgttactct tcatgggatc caccattggc tgtcctgctc gctgtgagtg ctctgcccag aacaaatctg ttagctgcca cagaagacgc ttgatcgcga tccccgaagg cattcccatt gagaccaaaa tcttggacct gagcaaaaat cgactaaaga gcataaaccc cgaagaattc atctcatatc ctctgttgga ggagatagac ttgagcgaca acatcatcgc caatgtagaa cctggggcat ttaacaatct cttaaacctg cgttccctcc gcctaaaagg caatcgcctt aagttggtcc ctttgggagt attcacggga ctgtccaacc tcaccaagct tgacattagt gagaataaga ttgtcatttt gctggactac atgttccagg atctgcataa cctgaagtct ctagaagtgg gggacaatga tttggtttat atatcacaca gggccttcag tggactattt agcttggagc agctcaccct ggagaagtgc aacttgacag cggtaccaac agaagccctt tccatctcc gcagcctcat caccctgcat ctgaagcatc tcaatatcaa caatatgcct gtgtatgcct ttaaaagatt attccacctg aaacaactag agatcgacta ttggccattg ctggatatga tgccagccaa tagcctctat ggtctcaacc tcacatccct ctcgatcact aacaccaacc tgtccactgt ccctttcctc gcctttaaac accttgtata cctgacccac cttaacctct cctacaatcc catcagcact attgaagcag gcatgttctc tgacctgatc cgcctacagg agcttcatgt agtcggggcc cagtccgcca ccattgaacc tcactccttc caagggctcc gcttcctccg cgtgctcaat gtatctcaga acctgctgga aacattggaa gagaatgtct
```

-continued

```
tctcttcccc tagggctttg gaggtcctga gcattaacaa
taacccacta gcgtgcgact gccgacttct ctggctcctg
cagcgacagg ccaccctgca gtttggaggc cagcagccca
tgtgtgccgg gccagacacc atacgtgaga ggtcatttaa
ggatttccat agcactgctc tttcttttta ttttacctgc
aaaaaaccca aaatccgtga aaagaagtta cagcacctcc
tagtggacga aggacagacg gtccagctgg agtgcaacgc
ggatggagac ccccagcccg tgatttcctg ggtgacacct
cgaaggcgtt ttatcaccac caagtccaac ggaagggcca
ctgtgttggg tgatggcacc ttagaaatcc gtttcgccca
ggatcaagac agtgggatgt atgtttgcat agctagcaat
gctgctggga atgacacctt cacggcatct ctcactgtga
agggattcac ttcagaccgc ttcctttacg caaacaggac
ccctatgtac atgactgact ccaatgacac cgtttccaac
ggcactaatg ccaatacttt ttccctggac cttaaaacaa
tactggtatc tacagccatg ggctgtttca cattcctggg
agtggtttta ttttgttttc tccttctttt tgtgtggagc
cgaggaaagg gcaaacacaa aaacagcatt gaccttgagt
atgtgccccg aaaaaacaat ggtgctgttg cagaagggga
ggtggctgga cccaggaggt tcaacatgaa aatgatataa
gggcccacca cacacacact actactgtct ctgtgttact
gttggtaatg agtaagacgt ctgatatagc gagtccatca
caaggtgatc aggcagcttc acacagctgc ccctgtgtca
aagcagggtc catggaagct ggaagacttc tcatggacac
tggctgatta gaggcaggca ggcatgtgtc agagccottc
acacagtggg atactaattg tttgcattgc aaatattggc
attctgggga tctcagtaat gaccctgaac ctttggctca
tgctgacgga caaaaattca acattttcta ccactgcaaa
actaaaagaa aaaaaattta aaaggaacaa cctacagtgt
aggatttaca tattaaaaaa agacacattt gtctaaaaca
tactctacgg taaaatttgt atttattatc atttgttaaa
accttgcatc atacaatact gttggttcag caccaaaaaa
aaaaaaaaaa aaaaaagag agatcaatat attctttttt
gaaacatata tgctgtatat gttttaaagc aatatgaatg
agaggttgtg cttttagtta ctcaccagta tagatccaag
tgtggtctca ctttcctttt atccgcagag aaacctgaga
atagatccct ggaataatag gctgagatgt gttgagatgt
gtatgtctga tgtaggatgc caagatacaa gagcccagtc
aaaactgctc aactctgtta acttctgtta ctataaataa
aggcatgtgc ctagttttga t.
```

The polypeptide sequence of rat LINGO-2 is reported as accession number NP_001101396 in GenBank:

(SEQ ID NO: 6)

mlhtaipcwq pflglamvll fmgstigcpa rcecsaqnks vschrrrlia ipegipietk ildlsknrlk sinpeefisy plleeidlsd niianvepga fnnlfnlrsl rlkgnrlklv plgvftglsn ltkldisenk ivilldymfq dlhnlkslev gdndlvyish rafsglfsle qltlekcnit avptealshl rslitlhlkh lninnmpvya fkrlfhlkql eidywplldm mpanslygln ltslsitntn lstvpflafk hlvylthlnl synpistiea gmfsdlirlq elhvvgaqlr tiephsfqgl rflrvinvsq nlletleenv fsspralevl sinnnplacd crllwllqrq atlqfggqqp mcagpdtire rsfkdfhsta lsfyftckkp kirekklqhl lvdegqtvql ecnadgdpqp viswvtprrr fittksngra tvlgdgtlei rfaqdqdsgm yvciasnaag ndtftasltv kgftsdrfly anrtpmymtd sndtvsngtn antfsldlkt ilvstamgcf tflgvvlfcf lllfvwsrgk gkhknsidle yvprknngav aegevagprr fnmkmi.

Naturally occurring human LINGO-2 polypeptide (also known as FLJ31810, Leucine-rich repeat and immunoglobulin-like domain-containing nogo receptor-interacting protein 2, LERN3, Leucine-rich repeat neuronal protein 3, Leucine-rich repeat neuronal protein 6C, LRRN6C, PRO31993, or UNQ9234) is an approximately 68 Kda protein of 606 amino acids (SEQ ID NO:2) LINGO-2 is a member of the LINGO protein family, which contains at least three other human paralogs. LINGO-1, LINGO-3, and LINGO-4. See Mi et al., *Nature Neurosci.* 7: 221-28 (2004). The human LINGO-2 polypeptide contains a stretch of leucine-rich repeats (including the N-terminal cap (LRRNT) and C-terminal cap (LRRCT)). LINGO-2 also contains an Ig domain, a transmembrane region, and an intracellular domain. In addition, naturally occurring LINGO-2 protein contains a signal sequence at the N-terminus of the protein. As the person of ordinary skill in the art will appreciate, the lengths of the various domains of LINGO-2 reported here are approximate. Table 2 lists approximate boundaries of the LINGO-2 domains, based on the amino acid sequence of SEQ ID NO:2.

TABLE 2

| LINGO-2 Domains | |
|---|---|
| Domain or Region | Residues of SEQ ID NO: 2 |
| Signal Sequence | 1-27 |
| LRRNT | 28-57 |
| LRR | 58-79 |
| LRR | 82-103 |
| LRR | 106-127 |
| LRR | 130-151 |
| LRR | 154-175 |
| LRR | 178-199 |
| LRR | 202-223 |
| LRR | 226-247 |
| LRR | 250-271 |

TABLE 2-continued

LINGO-2 Domains

| Domain or Region | Residues of SEQ ID NO: 2 |
|---|---|
| LRR | 274-295 |
| LRR | 298-319 |
| LRR | 322-343 |
| LRRCT | 355-408 |
| Ig | 410-500 |
| Transmembrane | 546-566 |
| Intracellular | 568-606 |

Tissue distribution of LINGO-2 has been studied in rats and mice. Expression of adult rat LINGO-2 is localized to the central, nervous system as determined by quantitative PCR (Q-PCR). In P6 (postnatal day 6) mice, expression of LINGO-2 is localized to cortex neurons and dorsal root ganglion as determined by quantitative PCR (Q-PCR) (See FIGS. 1 and 2).

III. Methods of Using Antagonists of LINGO-2

Although the LINGO-1 and LINGO-2 polypeptides share approximately 60.7% amino acid sequence, identity, as is demonstrated herein, antagonism of these polypeptides produces different effects on cells. More specifically, LINGO-2 antagonists do not promote remyelination while LINGO-1 antagonists do. In addition, the expression patterns of LINGO-1 and LINGO-2 differ. In particular, LINGO-2 expression is higher in the spinal cord than in the brain, while LINGO-1 expression is higher in the brain than the spinal cord.

Methods for treating a disease, disorder or injury associated with motor neuron survival or motor neuron axon growth, e.g., amyotrophic lateral sclerosis, in an animal suffering from such disease are provided herein. In some embodiments, the method comprises, consists essentially of or consists of administering to the animal an effective amount of a LINGO-2 antagonist. In certain embodiments the LINGO-2 antagonist is selected from the group consisting of a soluble LINGO-2 polypeptide, a LINGO-2 antibody or antigen-binding fragment thereof, a LINGO-2 antagonist polynucleotide, a LINGO-2 aptamer, and combinations thereof.

Additionally provided herein is a method for promoting motor neuron survival or axonal growth of a motor neuron (in a mammal or in vitro) comprising, consisting essentially of, or consisting of contacting the motor neuron with an effective amount of a LINGO-2 antagonist. Where the motor neuron is in a mammal, the amount can be a therapeutically effective amount. In certain embodiments the LINGO-2 antagonist is selected from the group consisting of a soluble LINGO-2 polypeptide, a LINGO-2 antibody or antigen-binding fragment thereof, a LINGO-2 antagonist polynucleotide, a LINGO-2 aptamer, and combinations thereof.

A LINGO-2 antagonist, e.g., a soluble LINGO-2 polypeptide, a LINGO-2 antibody, a LINGO-2 antagonist polynucleotide, or a LINGO-2 aptamer, to be used in treatment methods disclosed herein, can be prepared and used as a therapeutic agent that stops, reduces, prevents, or inhibits the ability of LINGO-2 to negatively regulate axonal growth or neuronal survival.

In some embodiments, a LINGO-2 antagonist can promote axonal growth of a particular type of motor neuron. For example, a LINGO-2 antagonist can promote axonal growth of an upper motor neuron or a lower motor neuron. A LINGO-2 antagonist can promote axonal growth of an alpha motor neuron or gamma motor neuron. A LINGO-2 antagonist can promote axonal growth of a somatic motor neuron, a special visceral motor neuron (branchial motor neuron), or a general visceral motor neuron (visceral motor neuron).

In some embodiments, a LINGO-2 antagonist can promote survival of a particular type of motor neuron. For example, a LINGO-2 antagonist can promote survival of an upper motor neuron or a lower motor neuron. A LINGO-2 antagonist can promote survival of an alpha motor neuron or gamma motor neuron. A LINGO-2 antagonist can survival of a somatic motor neuron, a special visceral motor neuron (branchial motor neuron), or a general visceral motor neuron (visceral motor neuron).

In some embodiments, a LINGO-2 antagonist can promote oligodendrocyte differentiation.

In some embodiments, a LINGO-2 antagonist can promote AKT phosphorylation. In some embodiments, a LINGO-2 antagonist can promote AKT phosphorylation in DRG cells.

Further embodiments include a method of inducing motor neuron survival to treat a disease, disorder or injury involving the destruction of motor neurons comprising administering a LINGO-2 antagonist to a mammal, optionally at or near the site of the disease, disorder or injury, in an amount sufficient to reduce inhibition of motor neuron axonal extension.

A LINGO-2 antagonist can be administered via direct administration, e.g., of a soluble LINGO-2 polypeptide, LINGO-2 antibody or antigen-binding fragment thereof, LINGO-2 antagonist polynucleotide, or a LINGO-2 aptamer to the patient. Alternatively, the LINGO-2 antagonist can be administered via an expression vector that produces the specific LINGO-2 antagonist. In certain embodiments, a LINGO-2 antagonist is administered in a treatment method that includes: (1) transforming or transfecting an implantable host cell with a nucleic acid, e.g., a vector, that expresses a LINGO-2 antagonist; and (2) implanting the transformed host cell into a mammal. In some embodiments, the host cell can be implanted at the site of a disease, disorder or injury. In some embodiments, the implantable host cell is removed from a mammal, temporarily cultured, transformed or transfected with an isolated nucleic acid encoding a LINGO-2 antagonist, and implanted back into the same mammal from which it was removed. The cell can be, but is not required to be, removed from the same site at which it is implanted. Such embodiments, sometimes known as ex vivo gene therapy, can provide a continuous supply of the LINGO-2 antagonist for a period of time.

Diseases or disorders which can be treated or ameliorated by the methods provided herein include diseases, disorders or injuries which relate to motor neuron survival. Such disease include, but are not limited to amyotrophic lateral sclerosis (ALS), primary lateral sclerosis (PLS), progressive muscular atrophy (PMA), hereditary spastic paraparesis (HSP), X-linked spinobulbar muscular atrophy (SBMA; Kenney disease) progressive bulbar palsy, pseudo-bulbar palsy, spinal muscular atrophy (SMA), post-polio syndrome (PPS), Huntington's disease, Essential tremor (ET), motor neuron disease, paralysis, Parkinson's disease, and other motor function-related diseases.

In some embodiments, administration of a LINGO-2 antagonist is sufficient to decrease or prevent a particular symptom associated with decreased motor neuron function. For example, a LINGO-2 antagonist can improve, stabilize, or prevent muscle atrophy, muscle weakness, fasciculation, fibrilliation, hypotonia, hyporeflexia, weakness, hypertonia, hyperreflexia, clonus, paralysis (e.g., quadriplegia, paraplegia, or monoplegia), spasticity, Babinski test, resting, tremors, athetosis, chorea, ballismus, tardive dyskinesia, ridigity, dystonia, ataxia, dysmetria, dysdiadochokinesia, nystagmus, delay in initiating movements, bradykinesia, or other movement disorders.

IV. Soluble LINGO-2 Polypeptides

LINGO-2 polypeptides include fragments, variants, or derivative thereof of a soluble LINGO-2 polypeptide. Table 2 above describes the various domains of a human LINGO-2 polypeptide. Similar domain structures can be deduced for LINGO-2 polypeptides of other species, e.g., mouse LINGO-2 (SEQ ID NO:4). Soluble LINGO-2 polypeptides typically lack the transmembrane domain of the LINGO-2 polypeptide, and optionally lack the cytoplasmic domain of the LINGO-2 polypeptide. For example, certain soluble human LINGO-2 polypeptides lack amino acids 546-566 of SEQ ID NO:2, which comprise the transmembrane domains of human LINGO-2. Additionally, certain soluble LINGO-2 polypeptides comprise the LRR domains and the Ig domain of the LINGO-2 polypeptide.

A variant LINGO-2 polypeptide can also vary in sequence from the corresponding wild-type polypeptide. In particular, certain amino acid substitutions can be introduced into the LINGO-2 sequence without appreciable loss of a LINGO-2 biological activity. In exemplary embodiments, a variant LINGO-2 polypeptide contains one or more amino acid substitutions, and/or comprises an amino acid sequence which is at least 70%, 80%, 85%, 90%, 95%, 98% or 99% identical to a reference amino acid sequence selected from the group consisting of: amino acids 28 to 408 of SEQ ID NO:2, and amino acids 28 to 500 of SEQ ID NO:2 or equivalent fragments of LINGO-2 homologs (e.g., SEQ ID NO:4 or SEQ ID NO:6). A variant LINGO-2 polypeptide differing in sequence from any given fragment of LINGO-2 can include one or more amino acid substitutions (conservative or non-conservative), one or more deletions, and/or one or more insertions. In certain embodiments, the soluble LINGO-2 polypeptide promotes motor neuron survival or motor neuron axonal growth, e.g., in a mammal.

A soluble LINGO-2 polypeptide can comprise a fragment of at least six, e.g., ten, fifteen, twenty, twenty-five, thirty, forty, fifty, sixty, seventy, one hundred, or more amino acids of SEQ ID NO:2, SEQ ID NO:4, or SEQ ID NO:6. In addition, a soluble LINGO-2 polypeptide can comprise at least one, e.g., five, ten, fifteen or twenty conservative amino acid substitutions. Corresponding fragments of soluble LINGO-2 polypeptides at least 70%, 75%, 80%, 85%, 90%, or 95% identical to a reference LINGO-2 polypeptide of SEQ ID NO:2 or SEQ ID NO:4 are also contemplated. In certain embodiments, the soluble LINGO-2 polypeptide promotes survival of motor neurons or promotes motor neuron axon growth, e.g., in a mammal.

By "a LINGO-2 reference amino acid sequence," or "reference amino acid sequence" is meant the specified sequence without the introduction of any amino acid substitutions. As one of ordinary skill in the art would understand, if there are no substitutions, the "isolated polypeptide" comprises an amino acid sequence which is identical to the reference amino acid sequence.

Additional soluble LINGO-2 polypeptides include, but are not limited to, a human LINGO-2 polypeptide fragment comprising, consisting essentially of, or consisting of amino acids 1 to 57 of SEQ ID NO:2; amino acids 1 to 79 of SEQ ID NO:2; amino acids 1 to 103 of SEQ ID NO:2; amino acids 1 to 127 of SEQ ID NO:2; amino acids 1 to 151 of SEQ ID NO:2; amino acids 1 to 175 of SEQ ID NO:2; amino acids 1 to 199 of SEQ ID NO:2; amino acids 1 to 223 of SEQ ID NO:2; amino acids 1 to 247 of SEQ ID NO:2; amino acids 1 to 271 of SEQ ID NO:2; amino acids 1 to 295 of SEQ ID NO:2; amino acids 1 to 319 of SEQ ID NO:2; amino acids 1 to 343 of SEQ ID NO:2; amino acids 1 to 408 of SEQ ID NO:2; amino acids 1 to 500 of SEQ ID NO:2; amino acids 1 to 545 of SEQ ID NO:2; amino acids amino acids 28 to 57 of SEQ ID NO:2; amino acids 28 to 79 of SEQ ID NO:2; amino acids 28 to 103 of SEQ ID NO:2; amino acids 28 to 127 of SEQ ID NO:2; amino acids 28 to 151 of SEQ ID NO:2; amino acids 28 to 175 of SEQ ID NO:2; amino acids 28 to 199 of SEQ ID NO:2; amino acids 28 to 223 of SEQ NO:2; amino acids 28 to 247 of SEQ ID NO:2; amino acids 28 to 271 of SEQ ID NO:2; amino acids 28 to 295 of SEQ ID NO:2; amino acids 28 to 319 of SEQ ID NO:2; amino acids 28 to 343 of SEQ ID NO:2; amino acids 28 to 408 of SEQ ID NO:2; amino acids 28 to 500 of SEQ ID NO:2; amino acids 28 to 545 of SEQ ID NO:2; amino acids 58 to 79 of SEQ ID NO:2; amino acids 58 to 103 of SEQ ID NO:2; amino acids 58 to 127 of SEQ ID NO:2; amino acids 58 to 151 of SEQ ID NO:2; amino acids 58 to 175 of SEQ ID NO:2; amino acids 58 to 199 of SEQ ID NO:2; amino acids 58 to 223 of SEQ ID NO:2; amino acids 58 to 247 of SEQ ID NO:2; amino acids 58 to 271 of SEQ ID NO:2; amino acids 58 to 295 of SEQ ID NO:2; amino acids 58 to 319 of SEQ ID NO:2; amino acids 58 to 343 of SEQ ID NO:2; amino acids 58 to 408 of SEQ ID NO:2; amino acids 58 to 500 of SEQ ID NO:2; amino acids 58 to 545 of SEQ ID NO:2; amino acids 82 to 103 of SEQ ID NO:2; amino acids 82 to 127 of SEQ ID NO:2; amino acids 82 to 151 of SEQ ID NO:2; amino acids 82 to 175 of SEQ ID NO:2; amino acids 82 to 199 of SEQ ID NO:2; amino acids 82 to 223 of SEQ ID NO:2; amino acids 82 to 247 of SEQ ID NO:2; amino acids 82 to 271 of SEQ ID NO:2; amino acids 82 to 2 of SEQ ID NO:2; amino acids 82 to 319 of SEQ ID NO:2; amino acids 82 to 343 of SEQ ID NO:2; amino acids 82 to 408 of SEQ ID NO:2; amino acids 82 to 500 of SEQ ID NO:2; amino acids 82 to 545 of SEQ ID NO:2; amino acids 106 to 127 of SEQ ID NO:2; amino acids 106 to 151 of SEQ ID NO:2; amino acids 106 to 175 of SEQ ID NO:2; amino acids 106 to 199 of SEQ ID NO:2; amino acids 106 to 223 of SEQ ID NO:2; amino acids 106 to 247 of SEQ 11) NO:2; amino acids 106 to 271 of SEQ NO:2; amino acids 106 to 295 of SEQ ID NO:2; amino acids 106 to 319 of SEQ ID NO:2; amino acids 106 to 343 of SEQ ID NO:2; amino acids 106 to 408 of SEQ ID NO:2; amino acids 106 to 500 of SEQ ID NO:2; amino acids 106 to 545 of SEQ ID NO:2; amino acids 130 to 151 of SEQ ID NO:2; amino acids 130 to 175 of SEQ ID NO:2; amino acids 130 to 199 of SEQ ID NO:2; amino acids 130 to 223 of SEQ ID NO:2; amino acids 130 to 247 of SEQ ID NO:2; amino acids 130 to 271 of SEQ ID NO:2; amino acids 130 to 295 of SEQ ID NO:2; amino acids 130 to 319 of SEQ ID NO:2; amino acids 130 to 343 of SEQ ID NO:2; amino acids 130 to 408 of SEQ ID NO:2; amino acids 130 to 500 of SEQ ID NO:2; amino acids 130 to 545 of SEQ ID NO:2; amino acids 154 to 175 of SEQ ID NO:2; amino acids 154 to 199 of SEQ ID NO:2; amino acids 154 to 223 of SEQ ID NO:2; amino acids 154 to 247 of SEQ ID NO:2; amino acids 154 to 271 of SEQ ID NO:2; amino acids 154 to 295 of SEQ ID NO:2; amino acids 154 to 319 of SEQ ID NO:2; amino acids 154 to 343 of SEQ ID NO:2; amino acids 154 to 408 of SEQ ID NO:2; amino acids 154 to 500 of SEQ ID NO:2; amino acids 154 to 545 of SEQ ID NO:2; amino acids 178 to 199 of SEQ ID NO:2; amino acids 178 to 223 of SEQ ID NO:2; amino acids 178 to 247 of SEQ ID NO:2; amino acids 178 to 271 of SEQ ID NO:2; amino acids 178 to 295 of SEQ ID NO:2; amino acids 178 to 319 of SEQ ID NO:2; amino acids 178 to 343 of SEQ ID NO:2; amino acids 178 to 408 of SEQ ID NO:2; amino acids 178 to 500 of SEQ ID NO:2; amino acids 178 to 545 of SEQ ID NO:2; amino acids 202 to 223 of SEQ ID NO:2; amino acids 202 to 247 of SEQ ID NO:2; amino acids 202 to 271 of SEQ ID NO:2; amino acids 202 to 295 of SEQ ID NO:2; amino acids 202 to 319 of SEQ ID NO:2; amino acids 202 to 343 of SEQ ID NO:2; amino acids 202 to 408 of SEQ ID NO:2; amino acids 202 to 500 of SEQ ID NO:2; amino acids 202 to 545 of SEQ ID NO:2; amino acids 226 to 247 of SEQ ID NO:2; amino acids 226 to 271 of SEQ ID NO:2; amino acids 226 to 295 of SEQ ID NO:2; amino acids 226 to 319 of SEQ ID NO:2; amino acids 226 to 343 of SEQ ID NO:2: amino acids 226 to 408 of SEQ ID NO:2; amino acids 226 to 500 of SEQ ID NO:2; amino acids 226 to 545 of SEQ ID NO:2; amino acids 250 to 271 of SEQ ID NO:2; amino acids 250 to 295 of SEQ ID NO:2; amino acids 250 to 319 of SEQ ID NO:2; amino acids 250 to 343 of SEQ ID NO:2; amino acids 250 to 408 of SEQ ID NO:2; amino acids 250 to 500 of SEQ ID NO:2; amino acids 250 to 545 of SEQ ID NO:2; amino acids 274 to 295 of SEQ ID NO:2; amino acids 274 to 319 of SEQ ID NO:2; amino acids 274 to 343 of SEQ ID NO:2; amino acids 274 to 408 of SEQ ID NO:2; amino acids 274 to 500 of SEQ ID NO:2; amino acids 274 to 545 of SEQ ID NO:2; amino acids 298 to 319 of SEQ ID NO:2; amino acids 298 to 343 of SEQ ID NO:2; amino acids 298 to 408 of SEQ ID NO:2; amino acids 298 to 500 of SEQ ID NO:2; amino acids 298 to 545 of SEQ ID NO:2; amino acids 322 to 343 of SEQ ID NO:2; amino acids 322 to 408 of SEQ ID NO:2; amino acids 322 to 500 of SEQ ID NO:2; amino acids 322 to 545 of SEQ ID NO:2; amino acids 355 to 408 of SEQ ID NO:2; amino acids 355 to 500 of SEQ ID NO:2; amino acids 355 to 545 of SEQ ID NO:2; amino acids 410 to 500 of SEQ ID NO:2; amino acids 410 to 545 of SEQ ID NO:2; or fragments, variants, or derivatives of such polypeptides. In certain embodiments, the soluble LINGO-2 polypeptide promotes survival of motor neurons and/or promotes motor neuron axon growth, e.g., in a mammal.

As would be well understood by a person of ordinary skill in the art, the LINGO-2 fragments such as those listed above can vary in length, for example, by 1, 2, 3, 4, 5, 6, 7, 8, 9, or 10 amino acids at either end (either longer or shorter) based, for example, on alternate predictions of the LINGO-2 domain regions. Corresponding fragments of soluble LINGO-2 polypeptides at least 70%, 75%, 80%, 85%, 90%, or 95% identical to SEQ ID NO:2, SEQ ID NO:4, SEQ ID NO:6, or fragments thereof described herein are also contemplated.

Soluble LINGO-2 polypeptides can include any combination of two or more soluble LINGO-2 polypeptides. Accordingly, soluble LINGO-2 polypeptide dimers, either homodimers or heterodimers, are contemplated. Two or more soluble LINGO-2 polypeptides as described herein can be directly connected, or can be connected via a suitable peptide linker. Such peptide linkers are described elsewhere herein.

In addition, any of the fragments listed above can further include a secretory signal peptide at the N-terminus, e.g., amino acids 1 to 27 of SEQ ID NO:2. Other secretory signal peptides, such as those described elsewhere herein, can also be used.

Soluble LINGO-2 polypeptides can be cyclic. Cyclization of the soluble LINGO-2 polypeptides reduces the conformational freedom of linear peptides and results in a more structurally constrained molecule. Many methods of peptide cyclization are known in the art. For example, "backbone to backbone" cyclization by the formation of an amide bond between the N-terminal and the C-terminal amino acid residues of the peptide. The "backbone to backbone" cyclization method includes the formation of disulfide bridges between two w-thio amino acid residues (e.g., cysteine, homocysteine). Certain soluble LINGO-2 peptides include modifications on the N- and C-terminus of the peptide to form a cyclic LINGO-2 polypeptide. Such modifications include, but are not limited, to cysteine residues, acetylated cysteine residues cysteine residues with a $NH_2$ polypeptide and biotin. Other methods of peptide cyclization are described in Li & Roller. *Curr. Top. Med. Chem.* 3:325-341 (2002), which is incorporated by reference herein in its entirety.

V. Antibodies and Antigen-Binding Fragments Thereof

LINGO-2 antagonists also include LINGO-2-specific antibodies or antigen-binding fragments, variants, or derivatives that are antagonists of LINGO-2 activity, e.g., antibody C09. For example, binding of certain LINGO-2 antibodies to LINGO-2, as expressed in motor neurons, blocks inhibition of motor neuron survival, or blocks inhibition of motor neuron axon growth. In certain embodiments, the LINGO-2 antagonist antibody promotes survival of motor neurons, or promotes motor neuron axon growth, e.g., in a mammal.

In certain embodiments, the binding molecules, e.g., antibodies or antigen-binding fragments, variants, or derivatives thereof, e.g., antibody C09, bind to LINGO-2 and promote survival of motor neurons or promotes motor neuron axon growth.

In certain embodiments the anti-LINGO-2 antibodies bind human, rat, murine, or any combination of human, rat, and murine LINGO-2.

A. Anti-LINGO-2 Antibody Polypeptides

Isolated binding molecule, e.g., an antibody or antigen-binding fragment, variant, or derivative thereof that can specifically bind to the same LINGO-2 epitope as antibody C09 are also provided. In another embodiment, an isolated binding molecule, e.g., an antibody or antigen-binding fragment, variant, or derivative thereof, can specifically bind to the same LINGO-2 epitope as antibody comprising the VH and VL of C09. In another embodiment, an isolated binding molecule, e.g., an antibody or antigen-binding fragment, variant, or derivative thereof, can specifically bind to the same LINGO-2 epitope as antibody comprising the VH or VL of C09.

In another embodiment, an isolated binding molecule, e.g., an antibody or antigen-binding fragment, variant, or derivative thereof can specifically bind to LINGO-2 and competitively inhibit antibody C09 from specifically binding to LINGO-2, e.g., human, rat, murine, or any combination of human, rat, and murine LINGO-2. In another embodiment, an isolated binding molecule, e.g., an antibody or antigen-binding fragment, variant, or derivative thereof, can specifically bind to LINGO-2 and competitively inhibit an antibody comprising the VH and VL of C09 from specifically binding to LINGO-2, e.g., human, rat, murine, or any combination of human, rat, and murine LINGO-2. In another embodiment, an isolated binding molecule, e.g., an antibody or antigen-binding fragment, variant, or derivative thereof can specifically bind to LINGO-2 and competitively inhibit an antibody comprising the VH or VL of C09, e.g., human, rat, murine, or any combination of human, rat, and murine LINGO-2.

In certain embodiments, the binding molecule has an amino acid sequence that has at least 80%, 85%, 88%, 89%, 90%, 91%, 92%, 93%, 94%, or 95% sequence identity to the amino acid sequence for a reference anti-LINGO-2 antibody molecule. In a further embodiment, the binding molecule shares at least 96%, 97%, 98%, 99%, or 100% sequence identity to the reference antibody. In certain embodiments, the reference antibody is C09.

In another embodiment, an isolated antibody or antigen-binding fragment, variant, or derivative thereof comprises, consists essentially of, or consists of an immunoglobulin heavy chain variable domain (VH domain), where at least one of the CDRs of the VH domain has an amino acid sequence that is at least 80%, 85%, 90%, 95%, 96%, 97%, 98%, 99%, or identical to a CDR1, CDR2 or CDR3 region from VH amino acid sequences SEQ ID NO:7, 8, or 9 (see Table 3), wherein an antibody or antigen-binding fragment thereof comprising the encoded VH domain can specifically or preferentially bind to LINGO-2. In a further embodiment, and the antibody or antigen-binding fragment, variant, or derivative thereof promotes survival of motor neurons or promotes motor neuron axon growth.

TABLE 3

Reference $V_H$ CDR1, CDR2, and CDR3 Sequences*

| Antibody Name | $V_H$-CDR1 | $V_H$-CDR2 | $V_H$-CDR3 |
|---|---|---|---|
| C09 | P = LYWMN (SEQ ID NO: 7) | P = SISPSGGW TKYADSVKG (SEQ ID NO: 8) | P = DHWGSGSP DY (SEQ ID NO: 9) |
| | N = CTTTACTG GATGAAT (SEQ ID NO: 15) | N = TCTATCTC TCCTTCTGGTGG CTGGACTAAGTA TGCTGACTCCGT TAAAGGT (SEQ ID NO: 16) | N = GATCATTG GGGTTCAGGGAG CCCCGACTAC (SEQ ID NO: 17) |

*Determined by the Kabat system (see supra)
N = nucleotide sequence,
P = polypeptide sequence In another embodiment, an isolated antibody or antigen-binding fragment, variant, or derivative thereof comprises, consists essentially of, or consists of an immunoglobulin heavy chain variable domain ($V_H$ domain), where at least one of the CDRs of the $V_H$ domain has an amino acid sequence that is at least 80%, 85%, 90%, 95%, 96%, 97%, 98%, 99%, or identical to CDR 1, 2, or 3 having the amino acid sequence of SEQ ID NO:7, 8, or 9, respectively, wherein an antibody or antigen-binding fragment, variant, or derivative thereof comprising the encoded $V_H$ domain can specifically or preferentially bind to LINGO-2. In a further embodiment, and the antibody or antigen-binding fragment thereof promotes survival of motor neurons or promotes motor neuron axon growth.

In another embodiment, an isolated antibody or antigen-binding fragment, variant, or derivative thereof comprises, consists essentially of, or consists of an immunoglobulin heavy chain variable domain ($V_H$ domain), where at least one of the CDRs of the $V_H$ domain has an amino acid sequence identical, except for 1, 2, 3, 4, or 5 conservative amino acid substitutions, to CDR 1, 2, or 3 having the amino acid sequence of SEQ ID NO:7, 8, or 9, respectively, wherein an antibody or antigen-binding fragment, variant, or derivative thereof comprising the encoded $V_H$ domain can specifically or preferentially bind to LINGO-2. In a further embodiment, and the antibody or antigen-binding fragment thereof promotes survival of motor neurons or promotes motor neuron axon growth.

In another embodiment, an isolated antibody or antigen-binding fragment, variant, or derivative thereof comprises, consists essentially of, or consists of a VH domain that has an amino acid sequence that is at least 80%, 85%, 90%, 91%, 92%, 93%, 94%, 95%, 96%, 97%, 98%, 99%, or 100% identical to a VH amino acid sequence of SEQ ID NO: 10 (see Table 4), wherein an antibody or antigen-binding fragment, variant, or derivative thereof comprising the encoded VH domain can specifically or preferentially bind to LINGO-2. In a further embodiment, and the antibody or antigen-binding fragment variant or derivative thereof promotes survival of motor neurons or promotes motor neuron axon growth.

TABLE 4

Reference $V_H$ Sequences

| Antibody Name | $V_H$ |
|---|---|
| C09 | P = EVQLLESGGGLVQPGGSLRLSCAASGFTFSLYWMNWVRQ APGKGLEWVSSISFPSGGWTKYADSVKGRFTISRDNSKNTLYL QMNSLRAEDTAVYYCARDHWGSGSPDYWGQGTLVTVSS (SEQ ID NO: 10) |
| | N = GAAGTTCAATTGTTAGAGTCTGGTGGCGGTCTTGTTCAG CCTGGTGGTTCTTTACGTCTTTCTTGCGCTGCTTCCGGATTCA CTTTCTCTCTTTACTGGATGAATTGGGTTCGCCAAGCTCCTGG TAAAGGTTTGGAGTGGGTTTCTTCTATCTCTCCTTCTGGTGGC TGGACTAAGTATGCTGACTCCGTTAAAGGTCGCTTCACTATCT CTAGAGACAACTCTAAGAATACTCTCTACTTGCAGATGAACAG CTTAAGGGCTGAGGACACGGCCGTGTATTACTGTGCAAGAGAT CATTGGGGTTCAGGGAGCCCCGACTACTGGGGCCAGGGAACCC TGGTCACCGTCTCAAGC (SEQ ID NO: 18) |

N = nucleotide sequence,
P = polypeptide sequence

In another embodiment, an isolated antibody or antigen-binding fragment, variant, or derivative thereof comprises, consists essentially of, or consists of an immunoglobulin light chain variable domain ($V_L$ domain), where at least one of the CDRs of the $V_L$ domain has an amino acid sequence that is at least 80%, 85%, 90%, 95%, 96%, 97%, 98%, 99%, or identical to a CDR1, CDR2 or CDR3 region from $V_L$ amino acid sequences SEQ ID NO:11, 12, or 13 (see Table 5), wherein an antibody or antigen-binding fragment, variant, or derivative thereof comprising the encoded $V_L$ domain can specifically or preferentially bind to LINGO-2. In a further embodiment, and the antibody or antigen-binding fragment, variant, or derivative thereof promotes survival of motor neurons or promotes motor neuron axon growth.

TABLE 5

Reference $V_L$ CDR1, CDR2, and CDR3 Sequences*

| Antibody Name | $V_L$-CDR1 | $V_L$-CDR2 | $V_L$-CDR3 |
|---|---|---|---|
| C09 | P = TGSSRDVG GYDYVS (SEQ ID NO: 11) | P = EVTKRPS (SEQ ID NO: 12) | P = CSYAGANT YV (SEQ ID NO: 13) |
| | N = ACTGGATC CAGCCGTGACGT TGGTGGTTATGA TTATGTCTCC (SEQ ID NO: 19) | N = GAGGTCAC TAAGCGGCCCTC A (SEQ ID NO: 20) | N = TGCTCATA TGCAGGCGCCAA CACTTATGTC (SEQ ID NO: 21) |

*Determined by the Kabat system (see supra)
N = nucleotide sequence,
P = polypeptide sequence In another embodiment, an isolated antibody or antigen-binding fragment, variant, or derivative thereof comprises, consists essentially of, or consists of an immunoglobulin light chain variable domain (V_L domain), where at least one of the CDRs of the V_L domain has an amino acid sequence that is at least 80%, 85%, 90%, 95%, 96%, 97%, 98%, 99%, or identical to CDR 1, 2, or 3 having the amino acid sequence of SEQ ID NO:11, 12, or 13, respectively, wherein an antibody or antigen-binding fragment, variant, or aerivative thereof comprising the encoded VL domain can specifically or preferentially bind to LINGO-2. In a further embodiment, and the antibody or antigen-binding fragment, variant, or derivative thereof promotes survival of motor neurons or promotes motor neuron axon growth.

In another embodiment, an isolated antibody or antigen-binding fragment, variant, or derivative thereof comprises, consists essentially of, or consists of an immunoglobulin light chain variable domain (VL domain), where at least one of the CDRs of the VL domain has an amino acid sequence identical, except for 1, 2, 3, 4, or 5 conservative amino acid substitutions, to CDR 1, 2, or 3 having the amino acid sequence of SEQ ID NO:11, 12, or 13, respectively, wherein an antibody or antigen-binding fragment, variant, or derivative thereof comprising the encoded VL domain can specifically or preferentially bind to LINGO-2. In a further embodiment, and the antibody or antigen-binding fragment, variant, or derivative thereof promotes survival of motor neurons or promotes motor neuron axon growth.

In a further embodiment, an isolated antibody or antigen-binding fragment, variant, or derivative thereof comprises, consists essentially of, or consists of a VL domain that has an amino acid sequence that is at least 80%, 85%, 90%, 91%, 92%, 93%, 94%, 95%, 96%, 97%, 98%, 99%, or 100% identical to a VL amino acid sequence of SEQ ID NO:14 (see Table 6), wherein an antibody or antigen-binding fragment, variant, or derivative thereof comprising the encoded VL domain can specifically or preferentially bind to LINGO-2. In a further embodiment, and the antibody or antigen-binding fragment, variant, or derivative thereof inhibits promotes survival of motor neurons or promotes motor neuron axon growth.

TABLE 6

Reference $V_L$ sequences

| Antibody Name | $V_L$ |
|---|---|
| C09 | P = QSVLTQPPSASGSPGQSLTISCTGSSRDVGGYDYVSWFQ QHPGKAPKLVISEVTKRPSGVPDRFSGSKSGNTASLTVSGLQP EDEADYYCCSYAGANTYVFGSGTRVTVL (SEQ ID NO: 14) <br><br> N = CAGAGCGTCTTGACTCAGCCTCCCTCCGCGTCCGGGTCT CCTGGACAGTCACTCACCATCTCCTGCACTGGATCCAGCCGTG ACGTTGGTGGTTATGATTATGTCTCCTGGTTCCAACAACACCC AGGCAAAGCCCCCAAACTCGTGATTTCTGAGGTCACTAAGCGG CCCTCAGGGGTCCCTGATCGGTTCTCTGGCTCCAAGTCTGGCA ACACGGCCTCCCTGACCGTCTCTGGACTCCAACCTGAGGATGA GGCTGATTATTATTGCTGCTCATATGCAGGCGCCAACACTTAT GTCTTCGGAAGTGGGACCAGAGTCACCGTCCTG (SEQ ID NO:22) |

N = nucleotide sequence,
P = polypeptide sequence

Certain antagonist antibodies can specifically or preferentially bind to a particular LINGO-2 polypeptide fragment or domain, for example, a LINGO-2 polypeptide, fragment, variant, or derivative as described herein.

Suitable biologically active variants of the anti-LINGO-2 antibodies are also useful. Such variants will retain the desired binding properties of the parent anti-LINGO-2 antibody. Methods for making antibody variants are generally available in the art.

The precise chemical structure of a polypeptide capable of specifically binding LINGO-2 and retaining the desired activity depends on a number of factors. As ionizable amino and carboxyl groups are present in the molecule, a particular polypeptide can be obtained as an acidic or basic salt, or in neutral form. All such preparations that retain their biological activity when placed in suitable environmental conditions are included in the definition of anti-LINGO-2 antibodies as used herein. Further, the primary amino acid sequence of the polypeptide can be augmented by derivatization using sugar moieties (glycosylation) or by other supplementary molecules such as lipids, phosphate, acetyl groups and the like. It can also be augmented by conjugation with saccharides. Certain aspects of such augmentation are accomplished through post-translational processing systems of the producing host; other such modifications can be introduced in vitro. In any event, such modifications are included in the definition of an anti-LINGO-2 antibody used herein so long as the desired properties of the anti-LINGO-2 antibody are not destroyed. It is expected that such modifications can quantitatively or qualitatively affect the activity, either by enhancing or diminishing the activity of the polypeptide, in the various assays. Further, individual amino acid residues in the chain can be modified by oxidation, reduction, or other derivatization, and the polypeptide can be cleaved to obtain fragments that retain activity. Such alterations that do not destroy the desired properties (e.g., binding specificity for LINGO-2, binding affinity, and associated activity, e.g., ability to inhibit motor neuron death and promote motor neuron axon growth) do not remove the polypeptide sequence from the definition of anti-LINGO-2 antibodies of interest as used herein.

The art provides substantial guidance regarding the preparation and use of polypeptide variants. In preparing variants of an anti-LINGO-2 binding molecule, e.g., an antibody or antigen-binding fragment, variant, or derivative thereof, one of skill in the art can readily determine which modifications to the native protein's nucleotide or amino acid sequence will result in a variant that is suitable for use as a therapeutically active component of a pharmaceutical composition.

It is possible to introduce mutations only in framework regions or only in CDR regions of an antibody molecule. Introduced mutations can be silent or neutral missense mutations, i.e., have no, or little, effect on an antibody's ability to bind antigen. These types of mutations can be useful to optimize codon usage, or improve a hybridoma's antibody production. Alternatively, non-neutral missense mutations can alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen-binding activity or alteration in binding activity (e.g., improvements in antigen-binding activity or change in antibody specificity). Following mutagenesis, the encoded protein can routinely be expressed and the functional and/or biological activity of the encoded protein, (e.g., ability to immunospecifically bind at least one epitope of a LINGO-2 polypeptide) can be determined using techniques described herein or by routinely modifying techniques known in the art.

In certain embodiments, the anti-LINGO-2 antibodies comprise at least one optimized complementarity-determining region (CDR). By "optimized CDR" is intended that the CDR has been modified and optimized sequences selected based on the sustained or improved binding affinity and/or anti-LINGO-2 activity that is imparted to an anti-LINGO-2 antibody comprising the optimized CDR. "Anti-LINGO-2 activity" can include, e.g., activity which modulates one or more of the following activities associated with LINGO-2, e.g., LINGO-2 dependent motor neuron cell death, LINGO-2 dependent inhibition of motor neuron axon growth, or any other activity associated with LINGO-2. Anti-LINGO-2 activity can also be attributed to a decrease in incidence or severity of diseases associated with LINGO-2 expression, including, but not limited to, certain types of motor neuron related diseases, e.g., amyotrophic lateral sclerosis (ALS), Parkinson's disease, and Essential tremor (ET). The modifications can involve replacement of amino acid residues within the CDR such that an anti-LINGO-2 antibody retains specificity for the LINGO-2 antigen and has improved binding affinity and/or improved anti-LINGO-2 activity.

B. Polynucleotides Encoding Anti-LINGO-2 Antibodies

Nucleic acid molecules encoding anti-LINGO-2 antibodies of the invention, or antigen-binding fragments, variants, or derivatives thereof, are also provided herein.

In one embodiment, an isolated polynucleotide comprises, consists essentially of, or consists of a nucleic acid encoding an immunoglobulin heavy chain variable domain ($V_H$ domain), where at least one of the CDRs of the $V_H$ domain is encoded by a nucleic acid sequence that is at least 80%, 85%, 90%, 95%, 96%, 97%, 98%, 99%, or identical to a $V_H$CDR 1, 2, or 3 polynucleotide sequence of a $V_H$-encoding sequence selected from SEQ ID NO:18 (see Table 4). In certain embodiments, the polynucleotide encodes an antibody or antigen-binding fragment, variant, or derivative thereof that promotes survival of motor neurons and/or motor neuron axon growth.

In other embodiments, an isolated polynucleotide comprises, consists essentially of, or consists of a nucleic acid encoding an immunoglobulin $V_H$ domain, where the sequence of at least one of the CDRs of the $V_H$ domain is selected from the group consisting of: (a) a CDR1 sequence comprising the amino acid sequence set forth in SEQ ID NO 7; (b) a CDR2 sequence comprising the amino acid sequence set forth in SEQ ID NO:8; and (c) a CDR3 sequence comprising the amino acid sequence set forth in SEQ ID NO:9. In certain embodiments, the polynucleotide encodes an antibody or antigen-binding fragment, variant, or derivative thereof that promotes survival of motor neurons and/or motor neuron axon growth.

In a further embodiment, an isolated polynucleotide comprises, consists essentially of, or consists of a nucleic acid encoding a $V_H$ domain that has an amino acid sequence that is at least 80%, 85%, 90%, 91%, 92%, 93%, 94%, 95%, 96%, 97%, 98%, 99%, or 100% identical to a reference $V_H$ domain polypeptide sequence comprising SEQ ID NO:10, wherein an anti-LINGO-2 antibody comprising the encoded $V_H$ domain specifically or preferentially binds to LINGO-2. In certain embodiments, the polynucleotide encodes an antibody or antigen-binding fragment, variant, or derivative thereof promotes survival of motor neurons and/or motor neuron axon growth.

In one embodiment, an isolated polynucleotide comprises, consists essentially of, or consists of a nucleic acid encoding an immunoglobulin light chain variable domain ($V_L$ domain), where at least one of the CDRs of the $V_L$ domain is encoded by a nucleic acid sequence that is at least 80%, 85%, 90%, 95%, 96%, 97%, 98%, 99%, or identical to a $V_L$CDR 1, 2, or 3 polynucleotide sequence of a $V_L$-encoding sequence selected from SEQ ID NO:22 (see Table 6). In certain embodiments, the polynucleotide encodes an antibody or antigen-binding fragment, variant, or derivative thereof promotes survival of motor neurons and/or motor neuron axon growth.

In other embodiments, an isolated polynucleotide comprises, consists essentially of, or consists of a nucleic acid encoding an immunoglobulin $V_L$ domain, where the sequence of at least one of the CDRs of the $V_L$ domain is selected from the group consisting of (a) a CDR1 sequence comprising the amino acid sequence set forth in SEQ ID NO:11; (b) a CDR2 sequence comprising the amino acid sequence set forth in SEQ ID NO:12 and (c) a CDR3 sequence comprising the amino acid sequence set forth in SEQ ID NO:13. In certain embodiments, the polynucleotide encodes an antibody or antigen-binding fragment, variant, or derivative thereof promotes survival of motor neurons and/or or motor neuron axon growth.

In a further embodiment, an isolated polynucleotide comprises, consists essentially of, or consists of a nucleic acid encoding a $V_L$ domain that has an amino acid sequence that is at least 80%, 85%, 90%, 91%, 92%, 93%, 94%, 95%, 96%, 97%, 98%, 99%, or 100% identical to a reference $V_L$ domain polypeptide sequence comprising SEQ ID NO 14, wherein an anti-LINGO-2 antibody comprising the encoded $V_L$ domain specifically or preferentially binds to LINGO-2. In certain embodiments, the polynucleotide encodes an antibody or antigen-binding fragment, variant, or derivative promotes survival of motor neurons and/or motor neuron axon growth.

Any of the polynucleotides described above can further include additional nucleic acids, encoding, e.g., a signal peptide to direct secretion of the encoded polypeptide, antibody constant regions as described herein, or other heterologous polypeptides as described herein. Also, compositions comprising one or more of the polynucleotides described above are provided herein.

In one embodiment, a composition comprises a first polynucleotide and second polynucleotide wherein said first polynucleotide encodes a $V_H$ domain as described herein and wherein said second polynucleotide encodes a $V_L$ domain as described herein. Specifically a composition which comprises, consists essentially of, or consists of a $V_H$ domain-encoding polynucleotide, as set forth in SEQ ID NO:18 and a $V_L$ domain-encoding polynucleotide, for example, a polynucleotide encoding the $V_L$ domain as set forth in SEQ ID NO:22 is provided. A composition comprising, consisting essentially of, or consisting of a $V_H$ domain-encoding polynucleotide comprising nucleic acid sequences encoding SEQ ID NO:7, SEQ ID NO:8, and SEQ ID NO:9 and a $V_L$ domain-encoding polynucleotide comprising nucleic acid sequences encoding SEQ ID NO:11, SEQ ID NO:12, and SEQ ID NO:13 is also provided.

Fragments of the polynucleotides, as described elsewhere, are also provided. Additionally polynucleotides that encode fusion polypolypeptides, Fab fragments, and other derivatives, as described herein, are also contemplated.

The polynucleotides can be produced or manufactured by any method known in the art. For example, if the nucleotide sequence of the antibody is known, a polynucleotide encoding the antibody can be assembled from chemically synthesized oligonucleotides (e.g., as described in Kutmeier et al., *Bio Techniques* 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an anti-LINGO-2 antibody, or antigen-binding fragment, variant, or derivative thereof, can be generated from nucleic acid from a suitable source. If a clone containing a nucleic acid encoding a particular antibody is not available, but the sequence of the antibody molecule is known, a nucleic acid encoding the antibody can be chemically synthesized or obtained from a suitable source (e.g., an antibody cDNA library, or a cDNA library generated from, or nucleic acid, e.g., poly A+RNA, isolated from, any tissue or cells expressing the antibody or other anti-LINGO-2 antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody or other anti-LINGO-2 antibody. Amplified nucleic acids generated by PCR can then be cloned into replicable cloning vectors using any method well known in the art.

Once the nucleotide sequence and corresponding amino acid sequence of the anti-LINGO-2 antibody, or antigen-binding fragment, variant, or derivative thereof is determined, its nucleotide sequence can be manipulated using methods well known in the art for the manipulation of nucleotide sequences, e.g., recombinant DNA techniques, site directed mutagenesis, PCR, etc. (see, for example, the techniques described in Sambrook et al. (1990) *Molecular Cloning, A Laboratory Manual* (2nd ed.; Cold Spring Harbor Laboratory, Cold Spring Harbor, N.Y.) and Ausubel et al., eds. (1998) *Current Protocols in Molecular Biology* (John Wiley & Sons, NY), which are both incorporated by reference herein in their entireties), to generate antibodies having a different amino acid sequence, for example to create amino acid substitutions, deletions, and/or insertions.

A polynucleotide encoding an anti-LINGO-2 binding molecule, e.g., an antibody, or antigen-binding fragment, variant, or derivative thereof, can be composed of any polyribonucleotide or polydeoxyribonucleotide, which can be unmodified RNA or DNA or modified RNA or DNA. For example, a polynucleotide encoding anti-LINGO-2 antibody, or antigen-binding, fragment, variant, or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, a polynucleotide encoding an anti-LINGO-2 binding molecule, e.g., an antibody, or antigen-binding fragment, variant, or derivative thereof can be composed of triple-stranded regions comprising RNA or DNA or both RNA and DNA. A polynucleotide encoding an anti-LINGO-2 binding molecule, e.g., antibody, or antigen-binding fragment, variant, or derivative thereof, can also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations can be introduced by standard techniques, such as site-directed mutagenesis and PCR-mediated mutagenesis. Conservative amino acid substitutions can be made at one or more non-essential amino acid residues.

C. Characteristics of Anti-LINGO-2 Antibodies

In other embodiments, a binding molecule, e.g., an antibody, or antigen-binding fragment, variant, or derivative thereof specifically or preferentially binds to at least one epitope of LINGO-2 wherein the epitope comprises, consists essentially of, or consists of at least about four to five amino acids of SEQ ID NO:2 or SEQ ID NO:4, at least seven, at least nine, or between at least about 15 to about 30 amino acids of SEQ ID NO:2 or SEQ ID NO:4. The amino acids of a given epitope of SEQ ID NO:2 or SEQ ID NO:4 as described can be, but need not be contiguous or linear. In certain embodiments, the at least one epitope of LINGO-2 comprises, consists essentially of, or consists of a non-linear epitope formed by the extracellular domain of LINGO-2 as expressed on the surface of a cell or as a soluble fragment, e.g., fused to an IgG Fc region. Thus, in certain embodiments the at least one epitope of LINGO-2 comprises, consists essentially of, or consists of at least 4, at least 5, at least 6, at least 7, at least 8, at least 9, at least 10, at least 15, at least 20, at least 25, between about 15 to about 30, or at least 10, 15, 20, 25, 30, 35, 40, 45, 50, 55, 60, 65, 70, 75, 80, 85, 90, 95, or 100 contiguous or non-contiguous amino acids of SEQ ID NO:2, or SEQ ID NO:4. Where non-contiguous amino acids form an epitope through protein folding.

In other embodiments, an antibody, or antigen-binding fragment, variant, or derivative thereof specifically or preferentially binds to at least one epitope of LINGO-2, where the epitope comprises, consists essentially of, or consists of, in addition to one, two, three, four, five, six or more contiguous or non-contiguous amino acids of SEQ ID NO: 2 or SEQ ID NO: 4 as described above, and an additional polypeptide which modifies the protein, e.g., a carbohydrate polypeptide can be included such that the LINGO-2 antibody binds with higher affinity to modified target protein than it does to an unmodified version of the protein. Alternatively, the LINGO-2 antibody does not bind the unmodified version of the target protein at all.

In other embodiments, an antibody, or antigen-binding fragment, variant, or derivative thereof binds to the LRR domain of LINGO-2.

In additional embodiments, an antibody, or antigen-binding fragment, variant, or derivative thereof binds to an epitope in amino acids 28-408 of SEQ ID NO:2, in amino acids 58-343 of SEQ ID NO:2, in amino acids 82-343 of SEQ ID NO:2, in amino acids 106-343 of SEQ ID NO:2, in amino acids 130-343 of SEQ ID NO:2, in amino acids 154-343 of SEQ ID NO:2, in amino acids 178-343 of SEQ ID NO:2, in amino acids 202-343 of SEQ ID NO:2, in amino acids 226-343 of SEQ ID NO:2, or in amino acids 250-343 of SEQ ID NO:2.

In additional embodiments, an antibody, or antigen-binding fragment, variant, or derivative thereof binds to an epitope in amino acids 202-223 of SEQ ID NO:2, in amino acids 202-247 of SEQ ID NO:2, in amino acids 202-271 of SEQ ID NO:2, in amino acids 202-295 of SEQ ID NO:2, in amino acids 202-319 of SEQ ID NO:2, or in amino acids 202-343 of SEQ ID NO:2.

In additional embodiments, an antibody, or antigen-binding fragment, variant, or derivative thereof binds to an epitope in amino acids 226-247 of SEQ ID NO:2, in amino acids 226-271 of SEQ 10 NO:2, in amino acids 226-295 of SEQ ID NO:2, in amino acids 226-319 of SEQ ID NO:2, or in amino acids 226-343 of SEQ ID NO:2.

In additional embodiments, an antibody, or antigen-binding fragment, variant, or derivative thereof binds to an epitope in amino acids 250-271 of SEQ ID NO:2, in amino acids 250-295 of SEQ ID NO:2, in amino acids 250-319 of SEQ ID NO:2, or in amino acids 250-343 of SEQ ID NO:2.

In additional embodiments, an antibody, or antigen-binding fragment, variant, or derivative thereof binds to an epitope in amino acids 274-295 of SEQ ID NO:2, in amino acids 274-319 of SEQ ID NO:2, or in amino acids 274-343 of SEQ ID NO:2.

In additional embodiments, an antibody, or antigen-binding fragment, variant, or derivative thereof binds to an epitope in amino acids 298-319 of SEQ ID NO:2 or in amino acids 298-343 of SEQ ID NO:2.

In certain embodiments, an antibody, or antigen-binding fragment, variant, or derivative thereof binds specifically to at least one epitope of LINGO-2 or fragment or variant described above, i.e., binds to such an epitope more readily than it would bind to an unrelated, or random epitope; binds preferentially to at least one epitope of LINGO-2 or fragment or variant described above, i.e., binds to such an epitope more readily than it would bind to a related, similar, homologous, or analogous epitope; competitively inhibits binding of a reference antibody which itself binds specifically or preferentially to a certain epitope of LINGO-2 or fragment or variant described above; or binds to at least one epitope of LINGO-2 or fragment or variant described above with an affinity characterized by a dissociation constant KD of less than about $5 \times 10^{-2}$ M, about $10^{-2}$ M, about $5 \times 10^{-3}$ M, about $10^{-3}$ M, about $5 \times 10^{-4}$ M, about $10^{-4}$ M, about $5 \times 10^{-5}$ M, about $10^{-5}$ M, about $5 \times 10^{-6}$ M, about 10-6 M, about $5 \times 10^{-7}$ M, about $10^{-7}$ M, about $5 \times 10^{-8}$ M, about $10^{-8}$ M, about $5 \times 10^{-9}$ M, about $10^{-9}$ M, about $5 \times 10^{-10}$ M, about $10^{-10}$ M, about $5 \times 10^{-11}$ M, about $10^{-11}$ M, about $5 \times 10^{-12}$ M, about $10^{-12}$ M, about 5×10-13 M, about $10^{-13}$ M, about $5 \times 10^{-14}$ M, about $10^{-14}$ M, about $5 \times 10^{-15}$ M, or about $10^{-15}$ M. In a particular aspect, the antibody or fragment thereof preferentially binds to a human LINGO-2 polypeptide or fragment thereof, relative to a murine LINGO-2 polypeptide or fragment thereof.

As used in the context of antibody binding dissociation constants, the term "about" allows for the degree of variation inherent in the methods utilized for measuring antibody affinity. For example, depending on the level of precision of the instrumentation used, standard error based on the number of samples measured, and rounding error, the term "about $10^{-2}$M" might include, for example, from 0.05 M to 0.005 M.

In specific embodiments, an antibody, or antigen-binding fragment, variant, or derivative thereof binds LINGO-2 polypeptides or fragments or variants thereof with an off rate (k(off)) of less than or equal to $5 \times 10^{-2}$ sec–1, $10^{-2}$ sec$^{-1}$, $5 \times 10^{-3}$ sec$^{-1}$ or $10^{-3}$ sec–1. Alternatively, an antibody, or antigen-binding fragment, variant, or derivative thereof binds LINGO-2 polypeptides or fragments or variants thereof with an off rate (k(off)) of less than or equal to $5 \times 10^{-4}$ sec–1, $10^{-4}$ sec–1, $5 \times 10^{-5}$ sec$^{-1}$, or $10^{-5}$ sec$^{-5}$ $\times 10^{-6}$ sec$^{-1}$, $10^{-6}$ sec$^{-1}$, $5 \times 10^{-7}$ sec$^{-1}$ or $10^{-7}$ sec$^{-1.}$ In other embodiments, an antibody, or antigen-binding fragment, variant, or derivative thereof binds LINGO-2 polypeptides or fragments or variants thereof with an on rate (k(on)) of greater than or equal to $10^3$ M$^{-1}$ sec$^{-1}$, $5 \times 10^3$ M$^{-1}$ sec$^{-1}$, $10^4$ M$^{-1}$ sec$^{-1}$ or $5 \times 10^4$ M$^{-1}$ sec$^{-1}$. Alternatively, an antibody, or antigen-binding fragment, variant, or derivative thereof binds LINGO-2 polypeptides or fragments or variants thereof with an on rate (k(on)) greater than or equal to $10^5$ M$^{-1}$ sec$^{-1}$, $5 \times 10^5$M$^{-1}$ sec$^{-1}$, $10^6$ M$^{-1}$ sec$^{-1}$, or $5 \times 10^6$ M$^{-1}$ sec$^{-1}$ or $10^7$ M$^{-1}$ sec$^{-1}$.

In certain LINGO-2 antagonist antibodies, or antigen-binding fragments thereof, at least a fraction of one or more of the constant region domains has been deleted or otherwise altered so as to provide desired biochemical characteristics such as reduced effector functions, the ability to non-covalently dimerize, increased ability to localize at the site of a tumor, reduced serum half-life, or increased serum half-life when compared with a whole, unaltered antibody of approximately the same immunogenicity. For example, certain antibodies are domain deleted antibodies which comprise a polypeptide chain similar to an immunoglobulin heavy chain, but which lack at least a portion of one or more heavy chain domains. For instance, in certain antibodies, one entire domain of the constant region of the modified antibody will be deleted, for example, all or part of the CH2 domain will be deleted.

In certain LINGO-2 antagonist antibodies or antigen-binding fragments thereof, the Fc portion can be mutated to decrease effector function using techniques known in the art. For example, modifications of the constant region can be used to modify disulfide linkages or oligosaccharide moieties that allow for enhanced localization due to increased antigen specificity or antibody flexibility. The resulting physiological profile, bioavailability and other biochemical effects of the modifications can easily be measured and quantified using well know immunological techniques without undue experimentation.

In certain embodiments, a LINGO-2 antagonist antibody or antigen-binding fragment thereof will not elicit a deleterious immune response in the animal to be treated, e.g., in a human. In one embodiment, LINGO-2 antagonist antibodies or antigen-binding fragments thereof can be modified to reduce their immunogenicity using art-recognized techniques. For example, antibodies can be humanized, primatized, deimmunized, or chimeric antibodies can be made. These types of antibodies are derived from a non-human antibody, typically a murine or primate antibody, that retains or substantially retains the antigen-binding properties of the parent antibody, but which is less immunogenic in humans. This can be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., Proc. Natl. Acad. Sci. 81:6851-6855 (1984); Morrison et al, Adv. Immunol. 44:65-92 (1988); Verhoeyen et al., Science 239:1534-1536 (1988); Padlan, Molec. Immun. 28:489-498 (1991); Padlan, Molec. Immun. 31:169-217 (1994), and U.S. Pat. Nos. 5,585,089, 5,693,761, 5,693,762, and 6,190,370, all of which are hereby incorporated by reference in their entirety.

Modified forms of antibodies or antigen-binding fragments thereof can be made from whole precursor or parent antibodies using techniques known in the art. Exemplary techniques are discussed in more detail herein.

LINGO-2 antagonist antibodies or antigen-binding fragments thereof can be made or manufactured using techniques that are known in the art. In certain embodiments, antibody molecules or fragments thereof are "recombinantly produced," i.e., are produced using recombinant DNA technology. Exemplary techniques for making antibody molecules or fragments thereof are discussed in more detail herein.

LINGO-2 antagonist antibodies or fragments thereof can be generated by any suitable method known in the art including generation of polyclonal antibodies or preparation of monoclonal antibodies, e.g., through hybridoma or phage display.

A variety of host-expression vector systems can be utilized to express antibody molecules. The host cell can be co-transfected with two expression vectors, the first vector encoding a heavy chain derived polypeptide and the second vector encoding a light chain derived polypeptide. The two vectors can contain identical selectable markers which enable equal expression of heavy and light chain polypeptides. Alternatively, a single vector can be used which encodes both heavy and light chain polypeptides. In such situations, the light chain is advantageously placed before the heavy chain to avoid an excess of toxic free heavy chain (Proudfoot, Nature 322:52 (1986); Kohler, Proc. Natl. Acad. Sci. USA 77:2197 (1980)). The host cell can also be transfected with a single vector encoding a heavy chain derived polypeptide and a light chain derived polypeptide. The coding sequences for the heavy and light chains can comprise cDNA or genomic DNA.

The expression vector or vectors is transferred to a host cell by conventional techniques and the transfected cells are then cultured by conventional techniques to produce an antibody. Thus, host cells containing a polynucleotide encoding an antibody, or a heavy or light chain thereof, operably linked to a heterologous promoter are provided. In certain embodiments for the expression of double-chained antibodies, vectors encoding both the heavy and light chains can be co-expressed in the host cell for expression of the entire immunoglobulin molecule.

Once an antibody has been recombinantly expressed, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Alternatively, a method for increasing the affinity of antibodies is disclosed in US 2002 0123057 A1.

In one embodiment, a binding molecule or antigen-binding molecule comprises a synthetic constant region wherein one or more domains are partially or entirely deleted ("domain-deleted antibodies"). In certain embodiments compatible modified antibodies will comprise domain deleted constructs or variants wherein the entire CH2 domain has been removed (ΔCH2 constructs). For other embodiments a short connecting peptide can be substituted for the deleted domain to provide flexibility and freedom of movement for the variable region. Those skilled in the art will appreciate that such constructs can be desirable under certain circumstances due to the regulatory properties of the CH2 domain on the catabolic rate of the antibody. Domain deleted constructs can be derived using a vector (e.g., from Biogen IDEC Incorporated) encoding an IgG1 human constant domain (see, e.g., WO 02/060955A2 and WO02/096948A2). This exemplary vector was engineered to delete the CH2 domain and provide a synthetic vector expressing a domain deleted IgG1 constant region.

Also provided herein are uses of antibodies that comprise, consist essentially of, or consist of, variants (including derivatives) of antibody molecules (e.g., the VH regions and/or VL regions) described herein, which antibodies or fragments thereof immunospecifically bind to a LINGO-2 polypeptide.

VI. Polypeptide and Antibody Conjugates and Fusions

A LINGO-2 polypeptide, e.g., a LINGO-2 antagonist polypeptide, fused to a heterologous polypeptide to form a LINGO-2 fusion protein is also provided herein. Anti-LINGO-2 antibodies fused to heterologous polypeptides are also provided. LINGO-2 fusion proteins and antibody fusions can be used to accomplish various objectives, e.g., increased serum half-life, improved bioavailability, in vivo targeting to a specific organ or tissue type, improved recombinant expression efficiency, improved host cell secretion, ease of purification, and higher avidity. Depending on the objective(s) to be achieved, the heterologous polypeptide can be inert or biologically active. Also, it can be chosen to be stably fused to the LINGO-2 polypeptide or antibody or to be cleavable, in vitro or in vivo. Heterologous moieties to accomplish different objectives are known in the art.

As an alternative to expression of a LINGO-2 antagonist fusion polypeptide or antibody, a chosen heterologous polypeptide can be preformed and chemically conjugated to the LINGO-2 antagonist polypeptide or antibody. In most cases, a chosen heterologous polypeptide will function similarly, whether fused or conjugated to the LINGO-2 antagonist polypeptide or antibody. Therefore, in the following discussion of heterologous amino acid sequences, unless otherwise noted, it is to be understood that the heterologous sequence can be joined to the LINGO-2 antagonist polypeptide or antibody in the form of a fusion protein or as a chemical conjugate.

Some methods employ a LINGO-2 polypeptide wherein a LINGO-2 polypeptide is fused to an Fc region, i.e., the C-terminal portion of an Ig heavy chain constant region. In one embodiment, a soluble LINGO-2 polypeptide is fused to a hinge and Fc region. Potential advantages of a LINGO-2-Fc fusion include solubility, in vivo stability, and multivalency, e.g., dimerization. The Fc region used can be an IgA, IgD, or IgG Fc region (hinge-CH2-CH3). Alternatively, it can be an IgE or IgM Fc region (hinge-CH2-CH3-CH4). An IgG Fc region is can also be used, e.g., an IgG1 Fc region or IgG4 Fc region. Materials and methods for constructing and expressing DNA encoding Fc fusions are known in the art and can be applied to obtain LINGO-2 fusions without undue experimentation. Some methods employ a LINGO-2 fusion protein such as those described in Capon et al. U.S. Pat. Nos. 5,428,130 and 5,565,335.

Fully intact, wild-type Fc regions display effector functions that can be unnecessary or undesired in an Fc fusion protein. Therefore, certain binding sites can be deleted from the Fc region in a fusion protein. For example, since coexpression with the light chain is unnecessary, the binding site for the heavy chain binding protein, Bip (Hendershot et al., 1987, Immunol. Today 8:111-114), is deleted from the CH2 domain of the Fc region of IgE, such that this site does not interfere with the efficient secretion. Likewise, the cysteine residues present in the Fc regions which are responsible for binding to the light chain of the immunoglobulin can be deleted or substituted with another amino acid, such that these cysteine residues do not interfere with the proper folding of the Fc region. Transmembrane domain sequences, such as those present in IgM, can also be deleted.

In certain embodiments, the $IgG_1$ Fc region is used. Alternatively, the Fc region of the other subclasses of immunoglobulin gamma (gamma-2, gamma-3 and gamma-4) can be used in the secretion cassette. The $IgG_1$ Fc region of immunoglobulin gamma-1 includes at least part of the hinge region, the $C_H2$ region, and the $C_H3$ region. In some embodiments, the Fc region of immunoglobulin gamma-1 is a $C_H2$-deleted-Fc, which includes part of the hinge region and the $C_H3$ region, but not the $C_H2$ region. A $C_H2$-deleted-Fc has been described by Gillies et al., *Hum. Antibod. Hybridomas* 1:47 (1990). In some embodiments, the Fc region of one of IgA, IgD, IgE, or IgM, is used.

LINGO-2-Fc fusion proteins can be constructed in several different configurations. In one configuration the C-terminus of the soluble LINGO-2 polypeptide is fused directly to the N-terminus of the Fc hinge polypeptide. In a slightly different configuration, a short polypeptide, e.g., 2-10 amino acids, is incorporated into the fusion between the N-terminus of the soluble LINGO-2 polypeptide and the C-terminus of the Fc polypeptide. Such a linker provides conformational flexibility, which may improve biological activity in some circumstances. If a sufficient, portion of the hinge region is retained in the Fc polypeptide, the LINGO-2-Fc fusion will dimerize, thus forming a divalent molecule. A homogeneous population of monomeric Fc fusions will yield monospecific, bivalent dimers. A mixture of two monomeric Fc fusions each having a different specificity will yield bispecific, bivalent dimers.

LINGO-2 polypeptides and anti-LINGO-2 antibody polypeptides antibodies can further be recombinantly fused to a heterologous polypeptide at the N- or C-terminus. For example, LINGO-2 antagonist polypeptides or antibodies can be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

Fusion proteins comprising, consisting essentially of, or consisting of a LINGO-2 antagonist polypeptide or antibody fusion that inhibits LINGO-2 function are also provided. In certain embodiments, the heterologous polypeptide to which the LINGO-2 antagonist polypeptide or antibody is fused is useful for function or is useful to target the LINGO-2 antagonist polypeptide or antibody. In certain embodiments, a soluble LINGO-2 antagonist polypeptide, e.g., a LINGO-2 polypeptide comprising the LRR domains, Ig domain, or the entire extracellular domain (corresponding to amino acids 28 to 545 of SEQ ID NO 2), or any other LINGO-2 polypeptide fragment, variant or derivative described herein, is fused to a heterologous polypeptide polypeptide to form a LINGO-2 antagonist fusion polypeptide. A signal sequence is a polynucleotide that encodes an amino acid sequence that initiates transport of a protein across the membrane of the endoplasmic reticulum. Signal sequences useful for constructing an immunofusin include antibody light chain signal sequences, e.g., antibody 14.18 (Gillies et al., *J. Immunol. Meth.* 125:191-202 (1989)), antibody heavy chain signal sequences, e.g., the MOPC141 antibody heavy chain signal sequence (Sakano et al., *Nature* 286:5774 (1980)). Alternatively, other signal sequences can be used See, e.g., Watson, *Nucl. Acids Res.* 12:5145 (1984). The signal peptide is usually cleaved in the lumen of the endoplasmic reticulum by signal peptidases. This results in the secretion of an immunofusin protein containing the Fc region and the soluble LINGO-2 polypeptide.

In some embodiments the DNA sequence encodes a proteolytic cleavage site between the fusion protein and the LINGO-2 polypeptide. A cleavage site provides for the proteolytic cleavage of the encoded fusion protein, thus separating the fused domain (e.g., an Fc domain) from the target protein.

LINGO-2 antagonist polypeptides and antibodies include derivatives that are modified, i.e., by the covalent attachment of any type of molecule such that covalent attachment does not prevent the LINGO-2 antagonist polypeptide or antibody from inhibiting the biological function of LINGO-2. For example, but not by way of limitation, the LINGO-2 antagonist polypeptides and antibodies can be modified e.g., by glycosylation, acetylation, PEGylation, phosphylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of tunicamycin, etc. Additionally, the derivative can contain one or more non-classical amino acids.

Some embodiments involve a soluble LINGO-2 polypeptide or LINGO-2 antibody wherein one or more polymers are conjugated (covalently linked) to the LINGO-2 polypeptide or antibody. Examples of polymers suitable for such conjugation include polypeptides (discussed above), sugar polymers and polyalkylene glycol chains. Typically, but not necessarily, a polymer is conjugated to the soluble LINGO-2 polypeptide or LINGO-2 antibody for the purpose of improving one or more of the following: solubility, stability, or bioavailability.

The class of polymer generally used for conjugation to a LINGO-2 antagonist polypeptide or antibody is a polyalkylene glycol. Polyethylene glycol (PEG) is most frequently used. PEG moieties, e.g., 1, 2, 3, 4 or 5 PEG polymers, can be conjugated to each LINGO-2 antagonist polypeptide or antibody to increase serum half-life, as compared to the LINGO-2 antagonist polypeptide or antibody alone. PEG moieties are non-antigenic and essentially biologically inert. PEG moieties can be branched or unbranched.

The number of PEG moieties attached to the LINGO-2 antagonist polypeptide or antibody and the molecular weight of the individual PEG chains can vary. In general, the higher the molecular weight of the polymer, the fewer polymer chains attached to the polypeptide. Usually, the total polymer mass attached to the LINGO-2 antagonist polypeptide or antibody is from 20 kDa to 40 kDa. Thus, if one polymer chain is attached, the molecular weight of the chain is generally 20-40 kDa. If two chains are attached, the molecular weight of each chain is generally 10-20 kDa. If three chains are attached, the molecular weight is generally 7-14 kDa.

The polymer, e.g., PEG, can be linked to the LINGO-2 antagonist polypeptide or antibody through any suitable, exposed reactive group on the polypeptide. The exposed reactive group(s) can be, e.g., an N-terminal amino group or the epsilon amino group of an internal lysine residue, or both. An activated polymer can react and covalently link at any free amino group on the LINGO-2 antagonist polypeptide or antibody. Free carboxylic groups, suitably activated carbonyl groups, hydroxyl, guanidyl, imidazole, oxidized carbohydrate moieties and mercapto groups of the LINGO-2 antagonist polypeptide or antibody (if available) also can be used as reactive groups for polymer attachment.

In a conjugation reaction, from about 1.0 to about 10 moles of activated polymer per mole of polypeptide, depending on polypeptide concentration is typically employed. Usually, the ratio chosen represents a balance between maximizing the reaction while minimizing side reactions (often non-specific) that can impair the desired pharmacological activity of the LINGO-2 antagonist polypeptide or antibody. In certain embodiments, at least 50% of the biological activity (as demonstrated, e.g., in any of the assays described herein or known in the art) of the LINGO-2 antagonist polypeptide or antibody is retained. In further embodiments, nearly 100% is retained.

VII. LINGO-2 Polynucleotide Antagonists

Polynucleotides can also be used to antagonize LINGO-2 function. Therefore, LINGO-2 polynucleotide antagonists can promote motor neuron survival and/or promote axonal growth of a motor neuron. Specific embodiments comprise a method of treating a motor neuron related disorder, comprising administering an effective amount of a LINGO-2 polynucleotide antagonist, wherein the polynucleotide antagonist comprises a nucleic acid molecule that can specifically bind to a polynucleotide that encodes LINGO-2. The LINGO-2 polynucleotide antagonist can prevent expression of LINGO-2 (knockdown). In certain embodiments, the LINGO-2 polynucleotide antagonist promotes survival of motor neurons and/or motor neuron axon growth, e.g., in a mammal. LINGO-2 polynucleotide antagonists include, but are not limited to, antisense molecules, ribozymes, siRNA, shRNA and RNAi. Typically, such binding molecules are separately administered to the animal (see, for example, O'Connor, J. Neurochem. 56:560 (1991)), but such binding molecules can also be expressed in vivo from polynucleotides taken up by a host cell and expressed in vivo. See also Oligodeoxynucleotides as Antisense Inhibitors of Gene Expression, CRC Press, Boca Raton, Fla. (1988).

Molecules that mediate RNAi, including without limitation siRNA, can be produced in vitro by chemical synthesis (Hohjoh, FEBS Lett 521:195-199, 2002), by hydrolysis of dsRNA (Yang et al., Proc Natl Acad Sci USA 99:9942-9947, 2002), by in vitro transcription with T7 RNA polymerase (Donzeet et al., Nucleic Acids Res 30:e46, 2002; Yu et al., Proc Natl Acad Sci USA 99:6047-6052, 2002), and by hydrolysis of double-stranded RNA using a nuclease such as E. coli RNase III (Yang et al., Proc Nall Acad Sci USA 99:9942-9947, 2002).

siRNA molecules can also be formed by annealing two oligonucleotides to each other, typically have the following general structure, which includes both double-stranded and single-stranded portions:

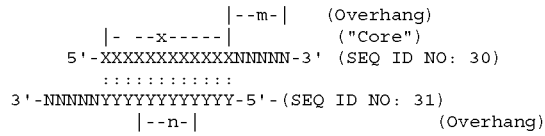

Wherein N, X and Y are nucleotides; X hydrogen bonds to Y; ":" signifies a hydrogen bond between two bases; x is a natural integer having a value between 1 and about 100; and m and n are whole integers having, independently, values between 0 and about 100. In some embodiments, N, X and Y are independently A, G, C and T or U. Non-naturally occurring bases and nucleotides can be present, particularly in the case of synthetic siRNA (e.g., the product of annealing two oligonucleotides). The double-stranded central section is called the "core" and has base pairs (bp) as units of measurement; the single-stranded portions are overhangs, having nucleotides (nt) as units of measurement. The overhangs shown are 3'-overhangs, but molecules with 5'-overhangs are also contemplated. Also contemplated are siRNA molecules with no overhangs (i.e., m=0 and n=0), and those having an overhang on one side of the core but not the other (e.g., m=0 and n≥1, or vice-versa).

Paddison et al. (Genes & Dev. 16:948-958, 2002) have, used small RNA molecules folded into hairpins as a means to effect RNAi. Accordingly, such short hairpin RNA (shRNA) molecules are also advantageously used in the methods provided herein. The length of the stem and loop of functional shRNAs varies; stem lengths can range anywhere >from about 25 to about 30 nt, and loop size can range from about 4 to about 25 nt without affecting silencing activity. While not wishing to be bound by any particular theory, it is believed that these shRNAs resemble the dsRNA products of the DICER RNase and, in any event, have the same capacity for inhibiting expression of a specific gene.

In some embodiments, the shRNA is expressed from a lentiviral vector (e.g., pLL3.7).

Antisense technology can be used to control gene expression through antisense DNA or RNA, or through triple-helix formation. Antisense techniques are discussed for example, in Okano, J. Neurochem. 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research 6:3073 (1979); Cooney et al., Science 241:456 (1988); and Dervan et al., Science 251:1300 (1991). The methods are based on binding of a polynucleotide to a complementary DNA or RNA.

For example, the 5"-coding portion of a polynucleotide that encodes LINGO-2 can be used to design an antisense RNA oligonucleotide of from about 10 to 40 base pairs in length. A DNA oligonucleotide is designed to be complementary to a region of the gene involved in transcription thereby preventing transcription and the production of the target protein. The antisense RNA oligonucleotide hybridizes to the mRNA in vivo and blocks translation of the mRNA molecule into the target polypeptide.

Absolute complementarity of an antisense molecule is not required. A sequence complementary to at least a portion of an RNA encoding LINGO-2, means a sequence having sufficient complementarity to be able to hybridize with the RNA, forming a stable duplex; or triplex. The ability to hybridize will depend on both the degree of complementarity and the length of the antisense nucleic acid. Generally, the larger the hybridizing nucleic acid, the more base mismatches it can contain and still form a stable duplex (or triplex as the case may be). One skilled in the art can ascertain a tolerable degree of mismatch by use of standard procedures to determine the melting point of the hybridized complex.

Oligonucleotides that are complementary to the 5'-end of a messenger RNA, e.g., the 5'-untranslated sequence up to and including the AUG initiation codon, should work most efficiently at inhibiting translation. However, sequences complementary to the 3'-untranslated sequences of mRNAs have been shown to be effective at inhibiting translation of mRNAs as well See generally, Wagner, R., Nature 372:333-335 (1994). Thus, oligonucleotides complementary to either the 5'- or -3'-non-translated, non-coding regions could be used in an antisense approach to inhibit translation of LINGO-2. Oligonucleotides complementary to the 5'-untranslated region of the mRNA should include the complement of the AUG start codon. Antisense oligonucleotides complementary to mRNA coding regions are less efficient inhibitors of translation but could be used Antisense nucleic acids are typically at least six nucleotides in length, for example, about 6 to about 50 nucleotides in length. In specific aspects the oligonucleotide is at least 10 nucleotides, at least 17 nucleotides, at least 25 nucleotides or at least 50 nucleotides.

Polynucleotides for use the therapeutic methods disclosed herein can be DNA or RNA or chimeric mixtures or derivatives or modified versions thereof, single-stranded or double-stranded. The oligonucleotide can be modified at the base polypeptide, sugar polypeptide, or phosphate backbone, for example, to improve stability of the molecule, hybridization, etc. The oligonucleotide can include other appended groups such as peptides (e.g., for targeting host cell receptors in vivo), or agents facilitating transport across the cell membrane (see, e.g., Letsinger et al., *Proc. Natl. Acad. Sci. U.S.A.* 86:6553-6556 (1989); Lemaitre et al., *Proc. Natl. Acad. Sci.* 84:648-652 (1987)); PCT Publication No. WO88/09810, published Dec. 15, 1988) or the blood-brain barrier (see, e.g., PCT Publication No. WO89/10134, published Apr. 25, 1988), hybridization-triggered cleavage agents. (see, e.g., Krol et al., *BioTechniques* 6:958-976 (1988)) or intercalating agents (see, e.g., Zon, *Pharm. Res.* 5:539-549(1988)). To this end, the oligonucleotide can be conjugated to another molecule, e.g., a peptide, hybridization triggered cross-linking agent, transport agent, hybridization-triggered cleavage agent, etc.

Polynucleotide compositions further include catalytic RNA, or a ribozyme (See, e.g., PCT International Publication WO 90/11364, published Oct. 4, 1990; Sarver et al., *Science* 247:1222-1225 (1990)). Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, *Nature* 334:585-591 (1988). In certain embodiments, the ribozyme is engineered so that the cleavage recognition site is located near the 5'-end of the target mRNA; i.e., to increase efficiency and minimize the intracellular accumulation of non-functional mRNA transcripts.

As in the antisense approach, ribozymes can be composed of modified oligonucleotides (e.g., for improved stability, targeting, etc.) and can be delivered to cells which express LINGO-2 in vivo. DNA constructs encoding the ribozyme can be introduced into the cell in the same manner as described above for the introduction of antisense encoding DNA. One method of delivery involves using a DNA construct "encoding" the ribozyme under the control of a strong constitutive or inducible promoter, such as, for example, pol III or pol II promoter, so that transfected cells will produce sufficient quantities of the ribozyme to destroy endogenous LINGO-2 messages and inhibit translation. Since ribozymes unlike antisense molecules, are catalytic, a lower intracellular concentration is required for efficiency.

VIII. LINGO-2 Aptamer Antagonists

In another embodiment, the LINGO-2 antagonist is an aptamer. An aptamer can be a nucleotide or a polypeptide which has a unique sequence, has the property of binding specifically to a desired target (e.g., a polypeptide), and is a specific ligand of a given target. Nucleotide aptamers include double stranded DNA and single stranded RNA molecules that bind to LINGO-2. In certain embodiments, the LINGO-2 aptamer antagonist promotes survival of motor neurons and/or motor neuron axon growth, e.g., in a mammal.

Nucleic acid aptamers are selected using methods known in the art, for example via the Systematic Evolution of Ligands by Exponential Enrichment (SELEX) process. SELEX is a method for the in vitro evolution of nucleic, acid molecules with highly specific binding to target molecules as described in e.g., U.S. Pat. Nos. 5,475,096, 5,580,737, 5,567,588, 5,707,796, 5,763,177, 6,011,577, and 6,699,843, incorporated herein by reference in their entirety. Another screening method to identify aptamers is described in U.S. Pat. No. 5,270,163 (also incorporated herein by reference). The SELEX process is based on the capacity of nucleic acids for forming a variety of two- and three-dimensional structures, as well as the chemical versatility available within the nucleotide monomers to act as ligands (form specific binding pairs) with virtually any chemical compound, whether monomeric or polymeric, including other nucleic acid molecules and polypeptides. Molecules of any size or composition can serve as targets.

Using the protein structure of LINGO-2, screening for aptamers that act on LINGO-2 using the SELEX process would allow for the identification of aptamers that inhibit LINGO-2-mediated processes.

Polypeptide aptamers are random peptides selected for their ability to bind to and thereby block the action of LINGO-2. Polypeptide aptamers can include a short variable peptide domain attached at both ends to a protein scaffold. This double structural constraint greatly increases the binding affinity of the peptide aptamer to levels comparable to an antibody's (nanomolar range). See, e.g., Hoppe-Seyler F et al. (2000) *J Mol Med* 78(8):426-430. The length of the short variable peptide is typically about 10 to 20 amino acids, and the scaffold can be any protein that has good solubility and compacity properties. One non-limiting example of a scaffold protein is the bacterial protein Thioredoxin-A. See, e.g., Cohen BA et al. (1998) *PNAS* 95(24): 14272-14277.

Polypeptide aptamers are peptides or small polypeptides that act as dominant inhibitors of protein function. Peptide aptamers specifically bind to target proteins, blocking their functional ability (Kolonin et al. (1998) *Proc. Natl. Acad. Sci.* 95: 14,266-14,271). Peptide aptamers that bind with high affinity and specificity to a target protein can be isolated by a variety of techniques known in the art. Peptide aptamers can be isolated from random peptide libraries by yeast two-hybrid screens (Xu, C. W., et al. (1997) *Proc. Natl. Acad. Sci.* 94:12,473-12,478) or by ribosome display (Hanes et al. (1997) *Proc. Natl. Acad. Sci.* 94:4937-4942). They can also be isolated from phage libraries (Hoogenboom, H. R., et al. (1998) *Immunotechnology* 4:1-20) or chemically generated peptide libraries. Additionally, polypeptide aptamers can be selected using the selection of Ligand Regulated Peptide Aptamers (LiRPAs). See, e.g., Binkowski B F et al., (2005) *Chem & Biol* 12(7): 847-855, incorporated herein by reference. Although the difficult means by which peptide aptamers are synthesized makes their use more complex than polynucleotide aptamers, they have unlimited chemical diversity. Polynucleotide aptamers are limited because they utilize only the four nucleotide bases, while peptide aptamers would have a much-expanded repertoire (i.e., 20 amino acids).

Peptide aptamers can be modified (e.g., conjugated to polymers or fused to proteins) as described for other polypeptides elsewhere herein.

IX. Vectors and Host Cells

Host-expression systems represent vehicles by which the coding sequences of interest can be produced and subsequently purified, but also represent cells which can, when transformed or transfected with the appropriate nucleotide coding sequences, express a LINGO-2 antagonist polypeptide or antibody in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing, antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Bacterial cells such as *Escherichia coli*, or eukaryotic cells, e.g., for the expression of whole recombinant antibody molecules, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)).

Vectors comprising nucleic acids encoding LINGO-2 antagonists, e.g., soluble LINGO-2 polypeptides, LINGO-2 antibodies, LINGO-2 antagonist polynucleotides, or LINGO-2 aptamers, can be used to produce antagonists. The choice of vector and expression control sequences to which such nucleic acids are operably linked depends on the functional properties desired, e.g., protein expression, and the host cell to be transformed.

Expression control elements useful for regulating the expression of an operably linked coding sequence are known in the art. Examples include, but are not limited to, inducible promoters, constitutive promoters, secretion signals, and other regulatory elements. When an inducible promoter is used, it can be controlled, e.g., by a change in nutrient status, or a change in temperature, in the host cell medium.

In one embodiment, a proprietary expression vector of Biogen IDEC, Inc., referred to as NEOSPLA (U.S. Pat. No. 6,159,730) can be used. This vector contains the cytomegalovirus promoter/enhancer, the mouse beta globin major promoter, the SV40 origin of replication, the bovine growth hormone polyadenylation sequence, neomycin phosphotransferase exon 1 and exon 2, the dihydrofolate reductase gene and leader sequence. This vector has been found to result in very high level expression upon transfection in CHO cells, followed by selection in G418 containing medium and methotrexate amplification. Of course, any expression vector which is capable of eliciting expression in cells can be used. Examples of suitable vectors include, but are not limited to plasmids pcDNA3, pHCMV/Zeo, pCR3.1, pEF1/His, pIND/GS, pRc/HCMV2, pSV40/Zeo2, pTRACER-HCMV, pUB6N5-His, pVAX1, and pZeoSV2 (available from Invitrogen, San Diego, Calif.), and plasmid pCI (available from Promega, Madison, Wis.). Additional cell expression vectors are known in the art and are commercially available. Typically, such vectors contain convenient restriction sites for insertion of the desired DNA segment. Exemplary vectors include pSVL and pKSV-10 (Pharmacia), pBPV-1, pm12d (International Biotechnologies), pTDT1 (ATCC 31255), retroviral expression vector pMIG and pLL3.7, adenovirus shuttle vector pDC315, AAV vectors, are pUC8, pUC9, pBR322 and pBR329 (BioRad), pPL and pKK223 (Pharmacia). Other exemplary vector systems are disclosed e.g., in U.S. Pat. No. 6,413,777.

X. Gene Therapy

A LINGO-2 antagonist can be produced in vivo in a mammal, e.g., a human patient, using a gene-therapy approach to treatment of a nervous-system disease, disorder or injury in which promoting survival of motor neurons and/or motor neuron axon growth would be therapeutically beneficial. This involves administration of a suitable LINGO-2 antagonist-encoding nucleic acid operably linked to suitable expression control sequences. Generally, these sequences are incorporated into a viral vector. Suitable viral vectors for such gene therapy include an adenoviral vector, an alphavirus vector, an enterovirus vector, a pestivirus vector, a lentiviral vector, a baculoviral vector, a herpesvirus vector, an Epstein Barr viral vector, a papovaviral vector, a poxvirus vector, a vaccinia viral vector, adeno-associated viral vector and a herpes simplex viral vector. The viral vector can be a replication-defective viral vector. Adenoviral vectors that have a deletion in its E1 gene or E3 gene are typically used. When an adenoviral vector is used, the vector usually does not have a selectable marker gene.

XI. Pharmaceutical Compositions

The LINGO-2 antagonists can be formulated into pharmaceutical compositions for administration to mammals, including humans. The pharmaceutical compositions comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions can be administered by any suitable method, e.g., parenterally, intraventricularly, orally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. As described previously, LINGO-2 antagonists used in the methods provided herein act in the nervous system to promotes survival of motor neurons and/or motor neuron axon growth. Accordingly, in certain methods, the LINGO-2 antagonists are administered in such a way that they cross the blood-brain barrier. This crossing can result from the physico-chemical properties inherent in the LINGO-2 antagonist molecule itself, from other components in a pharmaceutical formulation, or from the use of a mechanical device such as a needle, cannula or surgical instruments to breach the blood-brain barrier. Where the LINGO-2 antagonist is a molecule that does not inherently cross the blood-brain barrier, e.g., a fusion to a polypeptide that facilitates the crossing, suitable routes of administration are, e.g., intrathecal or intracranial. Where the LINGO-2 antagonist is a molecule that inherently crosses the blood-brain barrier, the route of administration can be by one or more of the various routes described below.

Sterile injectable forms of the compositions used in the methods provided herein can be aqueous or oleaginous suspension. These suspensions can be formulated according to techniques known in the art using suitable dispersing or wetting agents and suspending agents. The sterile, injectable preparation can also be a sterile, injectable solution or suspension in a non-toxic parenterally acceptable diluent or solvent, or example as a suspension in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or di-glycerides. Fatty acids, such as oleic acid and its glyceride derivatives are useful in the preparation injectables, as are natural pharmaceutically acceptable oils, such as olive oil or castor oil, especially in their polyoxyethylated versions. These oil solutions or suspensions can also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms can also be used for the purposes of formulation.

Parenteral formulations can be a single bolus dose, an infusion or a loading bolus dose followed with a maintenance dose. These compositions can be administered at specific fixed or variable intervals, e.g., once a day, or on an "as needed" basis.

Certain pharmaceutical compositions can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of a LINGO-2 antagonist that can be combined with the carrier materials to produce a single dosage form will vary depending upon the host treated, the type of antagonist used and the particular mode of administration. The composition can be administered as a single dose, multiple doses or over an established period of time in an infusion. Dosage regimens also can be adjusted to provide the optimum desired response (e.g., a therapeutic or prophylactic response).

The methods provided herein use a "therapeutically effective amount" or a "prophylactically effective amount" of a LINGO-2 antagonist. Such a therapeutically or prophylactically effective amount can vary according to factors such as the disease state, age, sex, and weight of the individual. A therapeutically or prophylactically effective amount is also one in which any toxic or detrimental effects are outweighed by the therapeutically beneficial effects.

A specific dosage and treatment regimen for any particular patient will depend upon a variety of factors, including the particular LINGO-2 antagonist used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

LINGO-2 antagonists can be administered directly to the nervous system, intracerebroventricularly, or intrathecally or can be administered systemically. Compositions for administration can be formulated so that a dosage of 0.001-10 mg/kg body weight per day of the LINGO-2 antagonist is administered. In some embodiments, the dosage is 0.01-1.0 mg/kg body weight per day. In some embodiments, the dosage is 0.001-0.5 mg/kg body weight per day.

For treatment with a LINGO-2 antagonist antibody, the dosage can range, e.g., from about 0.0001 to 100 mg/kg, and more usually 0.01 to 5 mg/kg (e.g., 0.02 mg/kg, 0.25 mg/kg, 0.5 mg/kg, 0.75 mg/kg, 1 mg/kg, 2 mg/kg, etc.), of the host body weight. For example dosages can be 1 mg/kg body weight or 10 mg/kg body weight or within the range of 1-10 mg/kg, for example, at least 1 mg/kg. Doses intermediate in the above ranges are also useful. Subjects can be administered such doses daily, on alternative days, weekly or according to any other schedule determined by empirical analysis. An exemplary treatment entails administration in multiple dosages over a prolonged period, for example, of at least six months. Additional exemplary treatment regimens entail administration once per every two weeks or once a month or once every 3 to 6 months. Exemplary dosage schedules include 1-10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated.

In certain embodiments, a subject can be treated with a nucleic acid molecule encoding a LINGO-2 antagonist polynucleotide. Doses for nucleic acids range from about 10 ng to 1 g, 100 ng to 100 mg, 1 µg to 10 mg, or 30-300 µg DNA per patient. Doses for infectious viral vectors vary from 10-100, or more, virions per dose.

Supplementary active compounds also can be incorporated into the compositions. For example, a soluble LINGO-2 polypeptide or a fusion protein can be coformulated with and/or coadministered with one or more additional therapeutic agents.

Any suitable method for delivering a LINGO-2 antagonist to a selected target tissue, including bolus injection of an aqueous solution or implantation of a controlled-release system can be used. Use of a controlled-release implant reduces the need for repeat injections.

The LINGO-2 antagonists used in the methods herein can be directly infused into the brain. Various implants for direct brain infusion of compounds are known and are effective in the delivery of therapeutic compounds to human patients suffering from neurological disorders. These include chronic infusion into the brain using a pump, stereotactically implanted, temporary interstitial catheters, permanent intracranial catheter implants, and surgically implanted biodegradable implants. See, e.g., Gill et al., supra; Scharfen et al., "High Activity Iodine-125 Interstitial Implant For Gliomas," *Int. J. Radiation Oncology Biol. Phys.* 24(4):583-591 (1992); Gaspar et al., "Permanent 125I Implants for Recurrent Malignant Gliomas," *Int. J. Radiation Oncology Biol. Phys.* 43(5):977-982 (1999); chapter 66, pages 577-580, Bellezza et al., "Stereotactic Interstitial Brachytherapy," in Gildenberg et al., Textbook of Stereotactic and Functional Neurosurgery, McGraw-Hill (1998); and Brem et al., "The Safety of Interstitial Chemotherapy with BCNU-Loaded Polymer Followed by Radiation Therapy in the Treatment of Newly Diagnosed Malignant Gliomas: Phase I Trial," *J. Neuro-Oncology* 26:111-23 (1995).

The compositions can also comprise a LINGO-2 antagonist dispersed in a biocompatible carrier material that functions as a suitable delivery or support system for the compounds. Suitable examples of sustained release carriers include semipermeable polymer matrices in the form of shaped articles such as suppositories or capsules. Implantable or microcapsular sustained release matrices include polylactides (U.S. Pat. No. 3,773,319; EP 58,481), copolymers of L-glutamic acid and gamma-ethyl-L-glutamate (Sidman et al., *Biopolymers* 22:547-56 (1985)); poly(2-hydroxyethyl-methacrylate), ethylene vinyl acetate (Langer et al., *J. Biomed. Mater. Res.* 15:167-277 (1981); Langer, *Chem. Tech.* 12:98-105 (1982)) or poly-D-(−)-3hydroxybutyric acid (EP 133,988).

In some embodiments, a LINGO-2 antagonist is administered to a patient by direct infusion into an appropriate region of the brain. See, e.g., Gill et al., "Direct brain infusion of glial cell line-derived neurotrophic factor in Parkinson disease," *Nature Med.* 9: 589-95 (2003). Alternative techniques are available and can be applied to administer a LINGO-2 antagonist. For example, stereotactic placement of a catheter or implant can be accomplished using the Riechert-Mundinger unit and the ZD (Zamorano-Dujovny) multipurpose localizing unit. A contrast-enhanced computerized tomography (CT) scan, injecting 120 ml of omnipaque, 350 mg iodine/ml, with 2 mm slice thickness can allow three-dimensional multiplanar treatment planning (STP, Fischer, Freiburg, Germany). This equipment permits planning on the, basis of magnetic resonance imaging studies, merging the CT and MRI target information for clear target confirmation.

The Leksell stereotactic system (Downs Surgical, Inc., Decatur, Ga.) modified for use with a GE CT scanner (General Electric Company, Milwaukee, Wis.) as well as the Brown-Roberts-Wells (BRW) stereotactic system (Radionics, Burlington, Mass.) can be used for this purpose. Thus, on the morning of the implant, the annular base ring of the BRW stereotactic frame can be attached to the patient's skull. Serial CT sections can be obtained at 3 mm intervals though the (target tissue) region with a graphite rod localizer frame clamped to the base plate. A computerized treatment planning program can be run on a VAX 11/780 computer (Digital Equipment Corporation, Maynard, Mass.) using CT coordinates of the graphite rod images to map between CT space and BRW space.

The methods of treatment of motor neuron related disorders as described herein are typically tested in vitro, and then in vivo in an acceptable animal model, for the desired therapeutic or prophylactic activity, prior to use in humans. Suitable animal models, including transgenic animals, are will known to those of ordinary skill in the art. For example, in vitro assays to demonstrate survival effect of the LINGO-2 antagonists are described herein. The effect of the LINGO-2 antagonists on motor neuron survival and motor neuron axon growth can be tested in vitro as described in the Examples. Finally, in vivo tests can be performed by creating transgenic mice which express the LINGO-2 antagonist or by administering the LINGO-2 antagonist to mice or rats in models as described herein.

EXAMPLES

Example 1

LINGO-2 is Specifically Expressed in the Central Nervous System

Expression of LINGO-2 in rat and mouse tissues was evaluated by quantitative PCR (Q-PCR) assay by the following method. Rat RNA was purchased from Clontech and mouse RNA was prepared from P6 mouse tissues. The mRNAs were extracted using Absolutely RNA Miniprep Kit (Stratagene) using the manufacturers instructions. Tissue specific first-strand cDNA was synthesized from the mRNA and was subjected to Taqman RT-PCR (performed essentially as described in Mi et al., *Nature Neuroscience* 7:221-228 (2004)) to quantify LINGO-2 mRNA levels, using (i) forward primer 5'-ACCTTGTATACCTGACCCACCTTAA-3' (SEQ ID NO:23), (ii) reverse primer 5'-AGAGAACAT-GCCTGCTTCAATAGTG-3' (rat) (SEQ ID NO:24) or 5'-AGAGAACATGCCAGCTTCAATAGTG-3' (mouse) (SEQ ID NO:25) and (iii) an MGB probe (Applied Biosystems) 5'-CCTCTCCTACAATCCC-3' (SEQ ID NO:26). TaqMan Gene Expression system (Mx3000P) was used to quantify mRNA levels.

Figure 2:
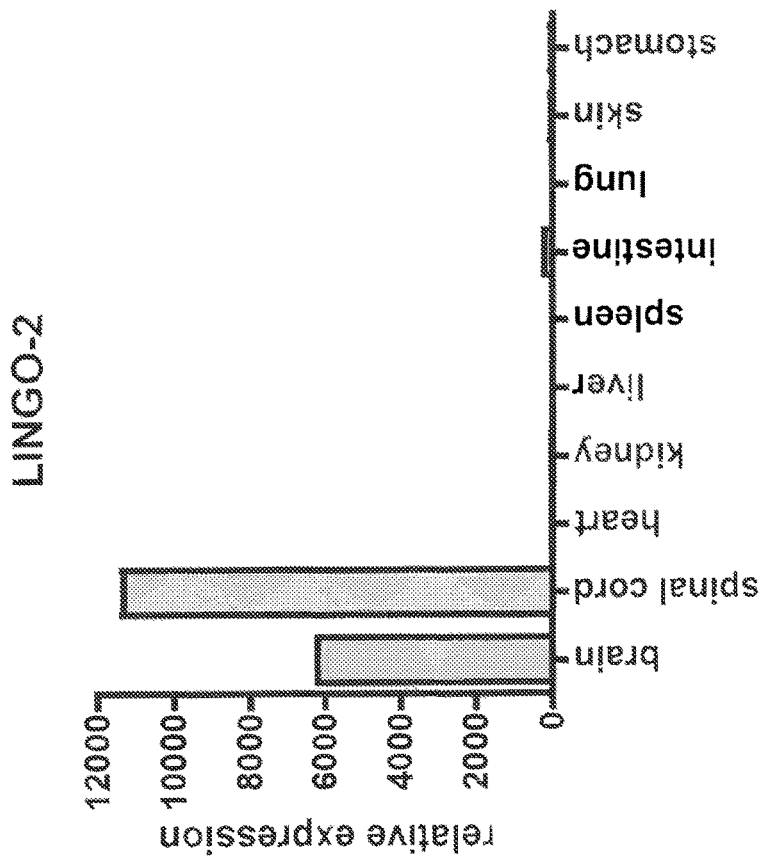
FIG. 2—Q-PCR of P6 mouse tissues. LINGO-2 is highly expressed in postnatal 6 days (P6) mouse brain and spinal cord tissues. Quantitation of mRNA expression of LINGO-2 was carried out by Q-PCR.

Relative LINGO-2 expression levels were determined by first normalizing LINGO-2 mRNA levels in the tissues to β-actin mRNA levels in the same tissues. β-actin mRNA level was quantified in parallel using primer set Rn0067869_m1 (rat) or Mn00607939 (mouse) (Applied Biosystems). Then, relative LINGO-2 mRNA levels were determined by comparing normalized LINGO-2 mRNA levels in each tissue to the normalized expression level in the Universal set for rat and lung tissue for mouse, which were both assigned a value of 1. The relative LINGO-2 expression levels for rat are shown in FIG. 1 and for P6 mouse tissue in FIG. 2. In rat, LINGO-2 was expressed to the greatest extent in brain. Expression levels in thymus, stomach, liver, colon, heart, placenta, kidney, spleen, breast, and lung were low or undetectable over background. In P6 mouse tissue, LINGO-2 was expressed to the greatest extent in brain and spinal cord. Notably, spinal cord expression levels were higher than brain expression levels. This is the opposite of what has been observed for LINGO-1, where expression in the brain is higher than expression in the spinal cord. Expression of LINGO-2 in heart, kidney, liver, spleen, intestine, lung, skin, and stomach were low or undetectable over background.

Example 2

LINGO-2 is Highly Expressed in Cortex and DRG Neurons

Expression of LINGO-2 in rat neuronal cells was evaluated by quantitative PCR (Q-PCR) assay by the following method. RNA was obtained from rat neuronal cell populations, and mRNA was extracted using Absolutely RNA Miniprep kit (Stratagene) using the manufacturer's instructions. First-strand cDNA was synthezised from the RNA and subjected to TaqMan RT-PCR (performed essentially as described in Mi et al., *Nature Neuroscience* 7:221-228

(2004)) to quantify LINGO-2 mRNA levels, using primers of SEQ ID NO:23-26 as described in Example 1. TaqMan Gene Expression system (Mx3000P) was used to quantify mRNA levels.

Figure 3:
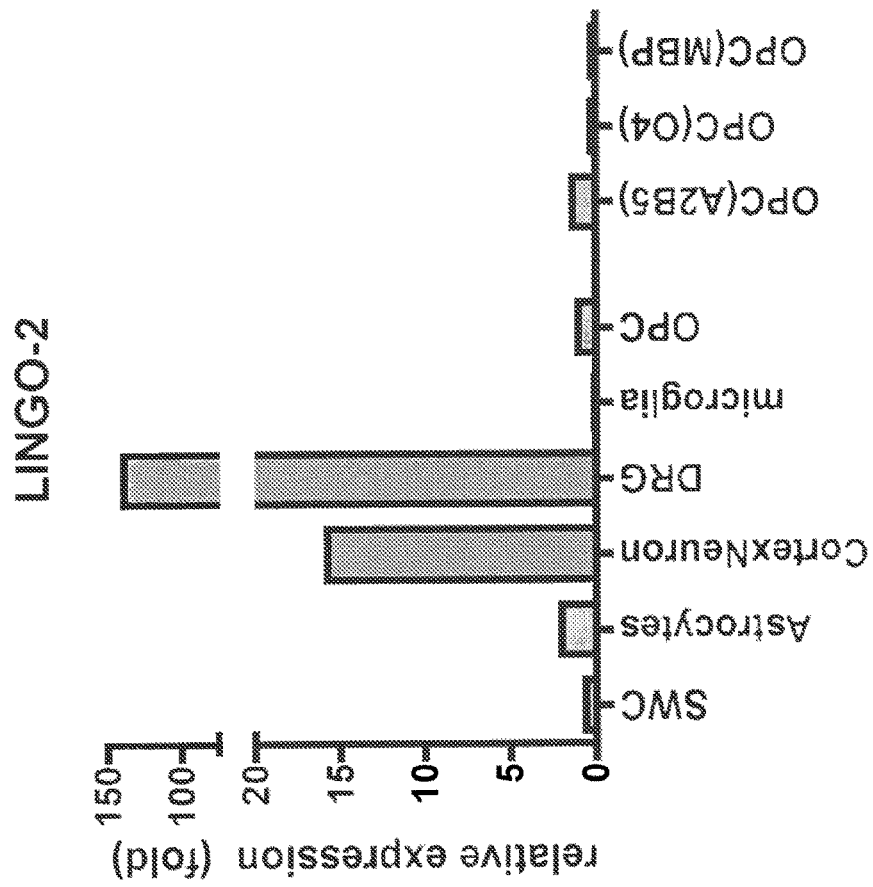
FIG. 3—Q-PCR of rat neuronal cell populations. LINGO-2 is highly expressed in cortex neurons and dorsal root ganglion (DRG). Quantitation of mRNA expression of LINGO-2 was carried out by Q-PCR.

Relative LINGO-2 expression levels were determined by first normalizing LINGO-2 mRNA levels in the neuronal cell populations to actin mRNA levels in the same neuronal cell populations. Then, relative LINGO-2 mRNA levels were determined by comparing normalized LINGO-2 mRNA levels in each tissue to the normalized expression level in oligodendrocyte precursor cells (OPC), which was assigned a value of 1. The relative LINGO-2 expression levels are shown in FIG. 3. LINGO-2 was expressed to the greatest extent in cortex and dorsal root ganglion (DRG) neurons. Expression in astrocytes was detectable, but less relative to cortex and DRG neurons. Levels were lowest in microglial cells.

Example 3

Construction and Purification of LINGO-2-Fc Fusion Protein

A construct was made fusing the extra-cellular portion of human LINGO-2 (residues 1-500) to the hinge and Fc region of human IgG1. The sequence of the soluble LINGO-2:Fc protein is shown below:

```
                                             (SEQ ID NO: 27)
MLHTAISCWQ  PFLGLAVVLI  FMGSTIGCPA  RCECSAQNKS

VSCHRRRLIA  IPEGIPIETK  ILDLSKNRLK  SVNPEEFISY

PLLEEIDLSD  NIIANVEPGA  FNNLFNLRSL  RLKGNRLKLV

PLGVFTGLSN  LTKLDISENK  IVILLDYMFQ  DLHNLKSLEV

GDNDLVYISH  RAFSGLLSLE  QLTLEKCNLT  AVPTEALSHL

RSLISLHLKH  LNINNMPVYA  FKRLFHLKHL  EIDYWPLLDM

MPANSLYGLN  LTSLSVTNTN  LSTVPFLAFK  HLVYLTHLNL

SYNPISTIEA  GMFSDLIRLQ  ELHIVGAQLR  TIEPHSFQGL

RFLRVLNVSQ  NLLETLEENV  FSSPRALEVL  SINNNPLACD

CRLLWILQRQ  PTLQFGGQQP  MCAGPDTIRE  RSFKDFHSTA

LSFYFTCKKP  KIREKKLQHL  LVDEGQTVQL  ECSADGDPQP

VISWVTPRRR  FITTKSNGRA  TVLGDGTLEI  RFAQDQDSGM

YVCIASNAAG  NDTFTASLTV  VDKTHTCPPC  PAPELLGGPS

VFLFPPKPKD  TLMISRTPEV  TCVVVDVSHE  DPEVKFNWYV

DGVEVHNAKT  KPREEQYNST  YRVVSVLTVL  HQDWLNGKEY

KCKVSNKALP  APIEKTISKA  KGQPREPQVY  TLPPSRDELT

KNQVSLTCLV  KGFYPSDIAV  EWESNGQPEN  NYKTTPPVLD

SDGSFFLYSK  LTVDKSRWQQ  GNVFSCSVMH  EALHNHYTQK

SLSLSPGK
```

Example 4

Production of LINGO-2-Specific Monoclonal Antibodies

Anti-LINGO-2 antibodies that specifically bind to LINGO-2 were made by screening a human naïve phagemid Fab library containing $3.5 \times 10^{10}$ unique clones (Nat Biotechnol. 2005 March; 23(3):344-8.) Selections were performed as described previously, and antibody C09 was identified/ The sequences of C09 are provided in Tables 3-6. Binding experiments demonstrate that the C09 antibody binds to LINGO-2, but does not bind to LINGO-1. In addition, the C09 antibody binds to a LINGO construct containing LRR7-LRR12 of LINGO-2 but lacking LRR1-LRR6 of LINGO-2.

Example 5

Blocking LINGO-2 by Soluble LINGO-2 or Anti-LINGO-2 Antibody Promotes Human Motor Neuron Survival Human motor neurons derived from human embryonic stem cells (hESCs) (Lonza) in 96-well plates were trypsinized in 0.025% trypsin/EDTA and replated onto a 4-chamber slide at a density of $5 \times 10^4$/well in MotorBlast Media (Lonza). The cells were incubated overnight at 37° C. in humidified air with 5% $CO_2$.

Cells were treated with 0.5 mM sodium arsenite for 30 min. Sodium arsenite provides an oxidative insult that induces cell death. Cells were washed three times, and then fresh MotorBlast Media containing either 50 µg/mL soluble LINGO-2-Fc, 10 µg/mL anti-LINGO-2 C09 Fab, or control hIgG was added to the cells. The cultures were incubated at 37° C. in humidified air with 5% $CO_2$ for 24 hours, then fixed with 4% paraformaldehyde.

Figure 4:
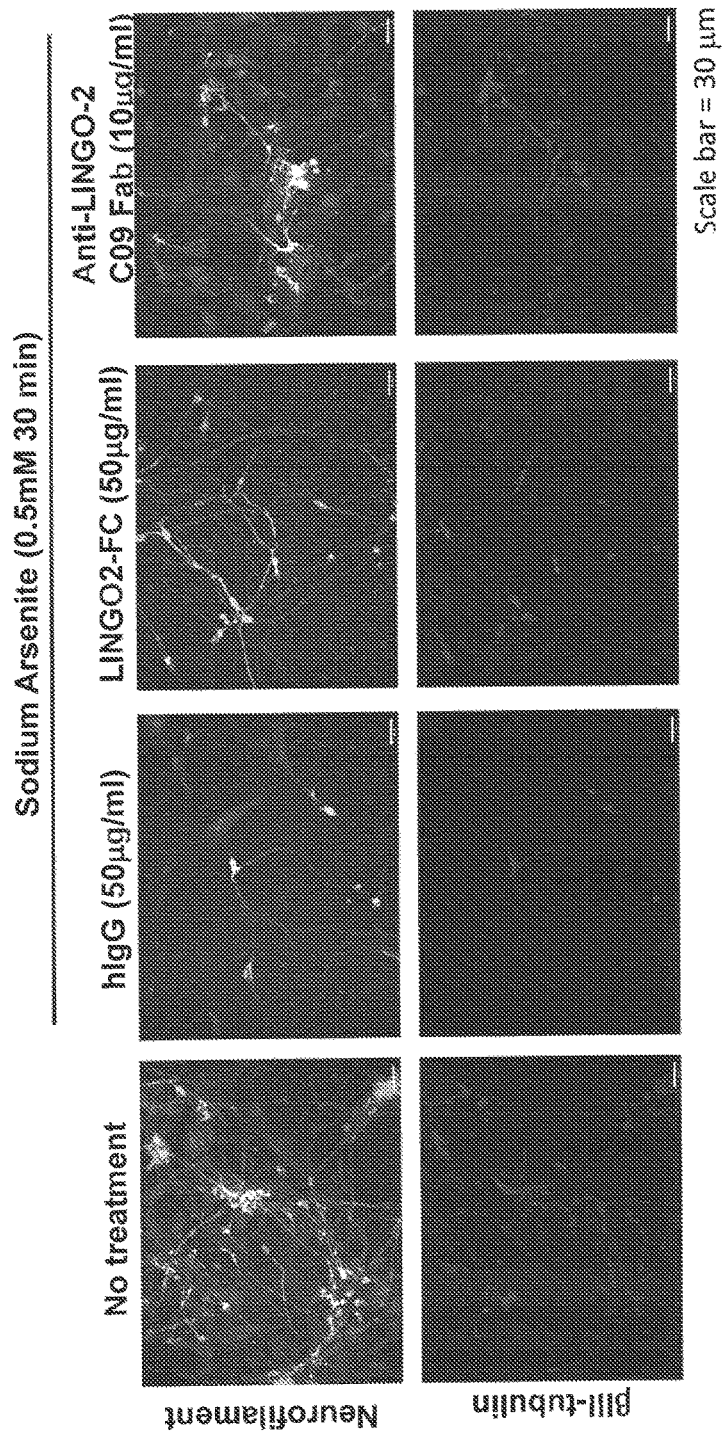
FIG. 4—LINGO-2-Fc and anti-LINGO-2 antibody promote motor neuron survival. Human motor neurons were treated with sodium arsenite for 30 min and allowed to recover in the presence of either human IgG (control), soluble LINGO-2-Fc, or anti-LINGO-2 antibody C09 Fab. After incubation, motor neurons were stained by immunocytochemistry with anti-βIII tubulin and anti-neurofilament.

Immunocytochemistry was performed on the cells to stain the motor neurons using anti-βIII tubulin (Covance) and the anti-neurofilament (Millipore) (FIG. 4).

As shown in FIG. 4, treatment with sodium arsenite reduced the number of motor neurons. However, both soluble LINGO-2-Fc and anti-LINGO-2 C09 Fab attenuated sodium arsenite-induced motor neuron death.

Example 6

Blocking LINGO-2 by Soluble LINGO-2 Promotes Motor Neuron Axon Growth

Motor neurons were isolated from embryonic day 16 (E16) rat spinal cords using Nycodenz gradient centrifugation. Spinal cords from E16 rat embryos were dissected out and incubated in 0.025% trypsin at 37° C. for 40 min. The trypsin solution was replaced with medium containing three volumes of Dulbecco's modified Eagle's medium to one volume of Nutrient Mixture F-12 Ham (DMEM/F12) and 0.004% DNase. The spinal cord cells were incubated for 5 min at and then dissociated by gentle trituration until the cell suspension was homogenous. The resultant spinal cord suspension was layered over a 4% bovine serum albumin (BSA) cushion, and cell pellets were collected by centrifugation of the solution at 100×g for at 4° C. The cell pellets were resuspended in DMEM/F12 medium containing 0.004% DNase and layered over Nycodenz gradients of 8.01%, 7.66%, and 7.05%. The gradients were centrifuged at 500×g. Motor neurons were identified as a white, turbid mass at the interface of the medium and the 7.05% solution and were collected.

Collected motor neurons were plated on a 4-chamber slide coated with 10 µg/mL poly-D lysine and 10 µg/mL lamini at a density of $5 \times 10^4$ cells/well in motor neuron growth media (1:1 ratio of Neurobasal medium, supplemented with 2% B27 and 0.5 mM glutamine, and DMEM/F12 medium (3:1), supplemented with 0.4 µg/mL hydrocortisone, 5 µg/mL insulin, and 10% fetal bovine serum (FBS). The resultant media was supplemented with 10 ng/mL neurotrophin-3, 10 ng/mL brain-derived neurotrophic factor, 10 ng/mL glial cell line-derived neurotrophic factor, 10 ng/mL ciliary neurotrophic factor, and antibiotics. The cells were incubated overnight at 37° C. in humidified air with 5% $CO_2$, and then treated with 0.5 mM sodium arsenite for 30 min. Cells were washed three times, and then fresh motor neuron growth media containing either 50 μg/mL soluble LINGO-2-Fc or control hIgG was added. The cultures were incubated at 37° C. in humidified air with 5% $CO_2$ for 24 hours, then fixed with 4% paraformaldehyde.

Figure 5:
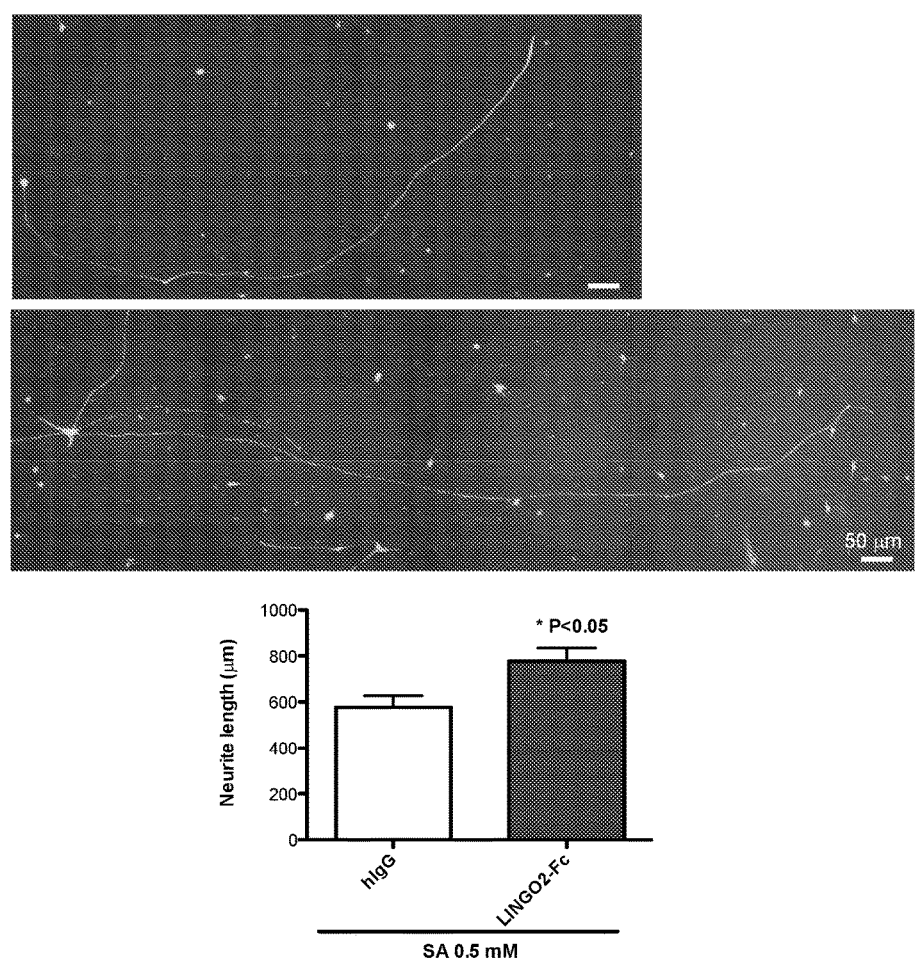
FIG. 5—LINGO-2-Fc promotes motor neuron axon growth. Motor neurons from embryonic day 16 (E16) rat spinal cords were isolated by Nycodenz gradient centrifugation. Isolated motor neurons were treated with sodium arsenite for 30 min and allowed to recover in the presence of either human IgG or soluble LINGO-2-Fc. After incubation, motor neurons were stained by immunocytochemistry with anti-neurofilament.

Immunocytochemistry was performed on the cells to stain the motor neurons using anti-neurofilament (Millipore) (FIG. 5). The longest neurite for each neuron was considered as the axon, and the axon length was measured using Openlab software. As seen in FIG. 5, after treatment of the cells with sodium arsenite, soluble LINGO-2 promoted neuron axon growth by approximately 20% compared to the hIgG control treated cells.

Example 7

LINGO-2 Expression Level is Up-regulated in SODG93A Mice

Transgenic animals with mutant copper/zinc superoxide dismutase (SOD1) DNA (e.g., SODG39A) develop paralytic motor neuron disease resembling human amylotrophic lateral sclerosis (ALS) patients and are commonly used as models for ALS. Narai et al., *Neurol. Int.* 1:e16 (2009).

65 day SODG93A or aged matched control wild-type mice were perfused with phosphate buffered saline (PBS), and the spinal cords were dissected out. Spinal cords were fixed in 4% paraformaldehyde, and the thoracic region of the spinal cords was embedded in Optimal Cutting Temperature (O.C.T.) compound for cryostat sectioning. The frozen sections were probed with a digoxigenin-labeled LINGO-2 anti-sense RNA probe 5'-TAATACGACTCAC-TATAGGGACAGAAGCCCTTTCCCATCT-3 (SEQ ID NO:28) and a digoxigenin-labeled sense RNA probe 5'-TAATACGACTCACTATAGGGACAGAAGCCCTTTC-CCATCT-3' (SEQ ID NO:29).

The sections were then stained using the tyramide signal amplification (TSA) plus fluorescence anti-digoxigenin conjugated antibody kit (Perkin Elmer) following the manufacturer's instructions.

Figure 6:
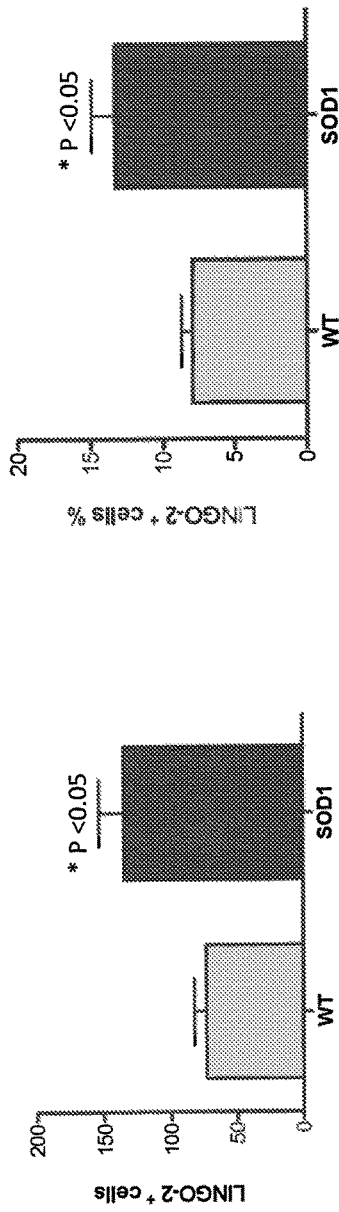
FIG. 6—LINGO-2 expression level is up-regulated in SODG93A mice. LINGO-2 RNA levels in 65-day old wild-type and SODG93A mice were measured using in situ hybridization. The number of LINGO-2 positive cells in ventral horn areas from each type of mice was counted. Graphs show the number of LINGO-2 positive cells (left) and percentage of LINGO-2 positive cells (right).

Quantitative analysis was performed in which the number of LINGO-2 positive cells in the ventral horn areas in each slide was counted at 20× by Openlab software. Three animals were analyzed for both SODG39A and wild-type mice. As seen in FIG. 6, LINGO-2 expression levels were up-regulated in the ventral horn of spinal cords from 65-day SODG39A mice when measured by in situ hybridization. There was a 2-fold increase in the number of LINGO-2 positive cells and a higher staining intensity in SODG39A mice compared to wild-type control mice.

Example 8

LINGO-2 Antagonists Promote Motor Neuron Growth and Survival in ALS

Transgenic mice expressing human SODG93A and aged-match controls are treated with a PBS (vehicle control) a control antibody or an anti-LINGO-2 antibody, e.g., C09. Treatments are provided via intraperitoneal injection on a weekly basis. Mice are sacrificed between 84 and 90 days of age and assessed for muscle mass and histology (e.g., to assess, motor neuronal survival). Other mice are monitored for additional time, e.g., about 134 days, for disease progression (e.g., ability to right from left and right lateral recumbancy and grip strength).

Example 9

LINGO-2 Antagonists Up-Regulate AKT Phosphorylation

Figure 7:
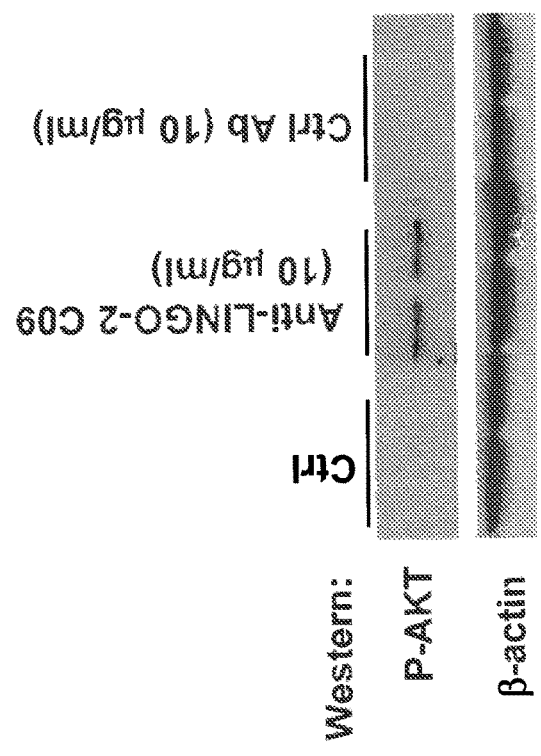
FIG. 7—Anti-LINGO-2 antibody up-regulates AKT phosphorylation. Levels of AKT phosphorylation were measured by Western blot in control samples and samples treated with the anti-LINGO-2 antibody C09 or a control antibody.

Motor neurons were incubated in the presence of equal concentrations of an anti-LINGO-2 antibody, C09) or a control antibody. Cell lysates were collected and assayed for levels of phosphorylated-AKT protein by Western analysis. Levels of β-actin were also measured as a control. As shown in FIG. 7, the anti-LINGO-2 antibody increased AKT phosphorylation.

Example 10

LINGO-2 Antagonists Promote Oligodendrocyte Differentiation

Figure 8:
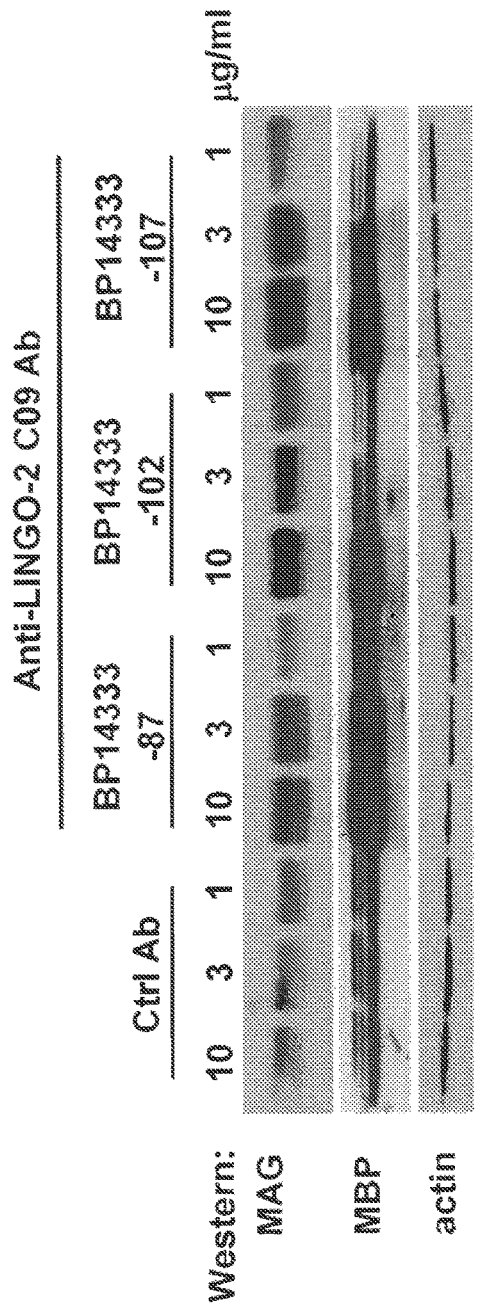
FIG. 8—Anti-LINGO-2 antibody promotes oligodendrocyte differentiation. Levels of myelin associated glycoprotein (MAG) and myelin basic protein (MBP) were measured in control samples and samples treated with the anti-LINGO-2 antibody C09 at concentrations of 1, 3, or 10 µg/ml.

The role of anti-LINGO-2 antibodies was investigated in vitro by treating oligodendrocyte progenitor cells with increasing quantities of C09 antibody and testing for myelin associated glycoprotein (MAG) and myeling basic protein (MBP) proteins by Western blotting. As shown in FIG. 8, treatment with the C09 antibody increased MAG and MBP levels in a dose-dependent manner. MPB is a marker of mature oligodendrocytes. Thus these data indicate that LINGO-2 antagonists promote oligodendrocyte differentiation.

What is claimed is:

1. A method for promoting survival of a motor neuron, comprising contacting said motor neuron with an effective amount of a LINGO-2 antagonist, wherein the LINGO-2 antagonist is an antibody or antigen-binding fragment thereof that binds LINGO-2 but does not bind LINGO-1.

2. A method for promoting axonal growth of a motor neuron, comprising contacting said motor neuron with a LINGO-2 antagonist, wherein the LINGO-2 antagonist is an antibody or antigen-binding fragment thereof that binds LINGO-2 but does not bind LINGO-1.

3. A method for promoting survival of a motor neuron in a human subject in need thereof, comprising administering to the human subject an effective amount of a LINGO-2 antagonist, wherein the LINGO-2 antagonist is an antibody or antigen-binding fragment thereof that binds LINGO-2 but does not bind LINGO-1.

4. The method of claim 3 wherein said human subject has been diagnosed with a disease, disorder, or injury involving motor neurons.

5. A method for promoting axonal growth of a motor neuron in a human subject in need thereof, comprising administering to the human subject an effective amount of a LINGO-2 antagonist, wherein the LINGO-2 antagonist is an antibody or antigen-binding fragment thereof that binds LINGO-2 but does not bind LINGO-1.

6. A method for treating a disease, disorder, or injury associated with survival of a motor neuron in a human subject in need thereof comprising administering to the human subject a therapeutically effective amount of a composition comprising a LINGO-2 antagonist, wherein the LINGO-2 antagonist is an antibody or antigen-binding fragment thereof that binds LINGO-2 but does not bind LINGO-1.

7. The method of claim 6, wherein said disease, disorder, or injury is selected from the group consisting of amyotrophic lateral sclerosis (ALS), primary lateral sclerosis (PLS), progressive muscular atrophy (PMA), hereditary spastic paraparesis (HSP), X-linked spinobulbar muscular atrophy (SBMA; Kenney disease), progressive bulbar palsy, pseudo-bulbar palsy, spinal muscular atrophy (SMA), post-polio syndrome (PPS), Huntington's disease, Essential tremor (ET), motor neuron disease, paralysis, and Parkinson's disease.

8. The method of claim 7, wherein said disease, disorder, or injury is amyotrophic lateral sclerosis (ALS).

9. A method for treating a disease, disorder, or injury associated with axonal growth of motor neurons in a human subject in need thereof comprising administering to the human subject a therapeutically effective amount of a composition comprising a LINGO-2 antagonist, wherein the LINGO-2 antagonist is an antibody or antigen-binding fragment thereof that binds LINGO-2 but does not bind LINGO-1.

* * * * *

SEQUENCE LISTING

```
<160> NUMBER OF SEQ ID NOS: 31

<210> SEQ ID NO 1
<211> LENGTH: 2792
<212> TYPE: DNA
<213> ORGANISM: Homo sapiens

<400> SEQUENCE: 1
aatttagaga agatgtaggg agtgttcaac atgttcgttg tggaagagaa agagctaaga        60
gagaggagct taaagacaca aacgggtaga atcaaggagt gtgctctcaa atgagaggaa       120
```

```
caggagtgac attaaccttg aaatgctcgg agactctact ccttcatgac agtaggagga    180
taattaacaa tagatacaaa tgcaggaatt gatgagtgcc atcagaaagc tgtatcatga    240
gctgcctgca cttctaaagt gtccagtgga tttttaatca catgagcctg gaaatagggt    300
tatgaaaaga agctcagagc agagcaccga aagtggccac taccagcatg aagagcccaa    360
caattcaaac tggtgaagtg agaaaaacag aatgcagctt tcaaggttcg tttcaagcag    420
ttggcttgtg ggactctgag agatgctgct gcccatgaca tgcgggaatt atcatgatca    480 actaccagc ttggatttca tccagtggcc aagagctttg tgtgggagac ggcaagggtt    540 ggattttca aaagagtaaa ccaggataaa tcatgaggaa cctataaccc ttttggccac    600
atgcaaaaaa gcaagacccg tgaccaaggt gtagactaag aagtggagtc atgcttcaca    660
cggccatatc atgctggcag ccattcctgg gtctggctgt ggtgttaatc ttcatgggat    720
ccaccattgg ctgccccgct cgctgtgagt gctctgccca gaacaaatct gttagctgtc    780
acagaaggcg attgatcgcc atcccagagg gcattcccat cgaaaccaaa atcttggacc    840
tcagtaaaaa caggctaaaa agcgtcaacc ctgaagaatt catatcatat cctctgctgg    900
aagagataga cttgagtgac aacatcattg ccaatgtgga accaggagca ttcaacaatc    960
tctttaacct gcgttccctc cgcctaaaag gcaatcgtct aaagctggtc cctttgggag   1020
tattcacggg gctgtccaat ctcactaagc ttgacattag tgagaataag attgtcattt   1080
tactagacta catgttccaa gatctacata acctgaagtc tctagaagtg ggggacaatg   1140
atttggttta tatatcacac agggcattca gtgggcttct tagcttggag cagctcaccc   1200
tggagaaatg caacttaaca gcagtaccaa cagaagccct ctcccacctc cgcagcctca   1260
tcagcctgca tctgaagcat ctcaatatca acaatatgcc tgtgtatgcc tttaaaagat   1320
tgttccacct gaaacaccta gagattgact attggccttt actggatatg atgcctgcca   1380
atagcctcta cggtctcaac ctcacatccc tttcagtcac caacaccaat ctgtctactg   1440 taccctcct tgcctttaaa cacctggtat acctgactca ccttaacctc tcctacaatc   1500
ccatcagcac tattgaagca ggcatgttct ctgacctgat ccgccttcag gagcttcata   1560
tagtgggggc ccagcttcgc accattgagc ctcactcctt ccaagggctc cgcttcctac   1620
gcgtgctcaa tgtgtctcag aacctgctgg aaactttgga agagaatgtc ttctcctccc   1680
ctagggctct ggaggtcttg agcattaaca acaaccctct ggcctgtgac tgccgccttc   1740
tctggatctt gcagcgacag cccaccctgc agtttggtgg ccagcaacct atgtgtgctg   1800
gcccagacac catccgtgag aggtctttca aggattccca tagcactgcc cttttctttt   1860
actttacctg caaaaaaccc aaaatccgtg aaaagaagtt gcagcatctg ctagtagatg   1920
aagggcagac agtccagcta gaatgcagtg cagatggaga cccgcagcct gtgatttcct   1980
gggtgacacc ccgaaggcgt ttcatcacca ccaagtccaa tggaagagcc accgtgttgg   2040
gtgatggcac cttggaaatc cgctttgccc aggatcaaga cagcgggatg tatgtttgca   2100
tcgctagcaa tgctgctggg aatgatacct tcacagcctc cttaactgtg aaaggattcg   2160
cttcagatcg tttttctttat gcgaacagga cccctatgta catgaccgac tccaatgaca   2220
ccatttccaa tggcaccaat gccaatactt tttccctgga ccttaaaaca atactggtgt   2280
ctacagctat gggctgcttc acattcctgg gagtggtttt atttgttttt cttctccttt   2340
ttgtgtggag ccgagggaaa ggcaagcaca aaaacagcat tgaccttgag tatgtgccca   2400
gaaaaaacaa tggtgctgtt gtggaaggag aggtagctgg acccaggagg ttcaacatga   2460
aaatgatttg aaggcccacc cctcacatta ctgtctcttt gtcaatgtgg gtaatcagta   2520
```

```
agacagtatg gcacagtaaa ttactagatt aagaggcagc catgtgcagc tgcccctgta   2580
tcaaaagcag ggtctatgga agcaggagga cttccaatgg agactctcca tcgaaaggca   2640
ggcaggcagg catgtgtcag agcccttcac acagtgggat actaagtgtt tgcgttgcaa   2700
atattggcgt tctggggatc tcagtaatga acctgaatat ttggctcaca ctcacggaca   2760
attattcagc attttctacc actgcaaaaa ac                                 2792
```

<210> SEQ ID NO 2
<211> LENGTH: 606
<212> TYPE: PRT
<213> ORGANISM: Homo sapiens

<400> SEQUENCE: 2

```
Met Leu His Thr Ala Ile Ser Cys Trp Gln Pro Phe Leu Gly Leu Ala
1               5                   10                  15

Val Val Leu Ile Phe Met Gly Ser Thr Ile Gly Cys Pro Ala Arg Cys
                20                  25                  30

Glu Cys Ser Ala Gln Asn Lys Ser Val Ser Cys His Arg Arg Arg Leu
            35                  40                  45

Ile Ala Ile Pro Glu Gly Ile Pro Ile Glu Thr Lys Ile Leu Asp Leu
        50                  55                  60

Ser Lys Asn Arg Leu Lys Ser Val Asn Pro Glu Glu Phe Ile Ser Tyr
65                  70                  75                  80

Pro Leu Leu Glu Glu Ile Asp Leu Ser Asp Asn Ile Ile Ala Asn Val
                85                  90                  95

Glu Pro Gly Ala Phe Asn Asn Leu Phe Asn Leu Arg Ser Leu Arg Leu
            100                 105                 110

Lys Gly Asn Arg Leu Lys Leu Val Pro Leu Gly Val Phe Thr Gly Leu
        115                 120                 125

Ser Asn Leu Thr Lys Leu Asp Ile Ser Glu Asn Lys Ile Val Ile Leu
    130                 135                 140

Leu Asp Tyr Met Phe Gln Asp Leu His Asn Leu Lys Ser Leu Glu Val
145                 150                 155                 160

Gly Asp Asn Asp Leu Val Tyr Ile Ser His Arg Ala Phe Ser Gly Leu
                165                 170                 175

Leu Ser Leu Glu Gln Leu Thr Leu Glu Lys Cys Asn Leu Thr Ala Val
            180                 185                 190

Pro Thr Glu Ala Leu Ser His Leu Arg Ser Leu Ile Ser Leu His Leu
        195                 200                 205

Lys His Leu Asn Ile Asn Asn Met Pro Val Tyr Ala Phe Lys Arg Leu
    210                 215                 220

Phe His Leu Lys His Leu Glu Ile Asp Tyr Trp Pro Leu Leu Asp Met
225                 230                 235                 240

Met Pro Ala Asn Ser Leu Tyr Gly Leu Asn Leu Thr Ser Leu Ser Val
                245                 250                 255

Thr Asn Thr Asn Leu Ser Thr Val Pro Phe Leu Ala Phe Lys His Leu
            260                 265                 270

Val Tyr Leu Thr His Leu Asn Leu Ser Tyr Asn Pro Ile Ser Thr Ile
        275                 280                 285

Glu Ala Gly Met Phe Ser Asp Leu Ile Arg Leu Gln Glu Leu His Ile
    290                 295                 300

Val Gly Ala Gln Leu Arg Thr Ile Glu Pro His Ser Phe Gln Gly Leu
305                 310                 315                 320
```

```
Arg Phe Leu Arg Val Leu Asn Val Ser Gln Asn Leu Leu Glu Thr Leu
            325                 330                 335

Glu Glu Asn Val Phe Ser Ser Pro Arg Ala Leu Glu Val Leu Ser Ile
            340                 345                 350

Asn Asn Asn Pro Leu Ala Cys Asp Cys Arg Leu Leu Trp Ile Leu Gln
            355                 360                 365

Arg Gln Pro Thr Leu Gln Phe Gly Gly Gln Pro Met Cys Ala Gly
            370                 375                 380

Pro Asp Thr Ile Arg Glu Arg Ser Phe Lys Asp Phe His Ser Thr Ala
385                 390                 395                 400

Leu Ser Phe Tyr Phe Thr Cys Lys Lys Pro Lys Ile Arg Glu Lys Lys
            405                 410                 415

Leu Gln His Leu Leu Val Asp Glu Gly Gln Thr Val Gln Leu Glu Cys
            420                 425                 430

Ser Ala Asp Gly Asp Pro Gln Pro Val Ile Ser Trp Val Thr Pro Arg
            435                 440                 445

Arg Arg Phe Ile Thr Thr Lys Ser Asn Gly Arg Ala Thr Val Leu Gly
            450                 455                 460

Asp Gly Thr Leu Glu Ile Arg Phe Ala Gln Asp Gln Asp Ser Gly Met
465                 470                 475                 480

Tyr Val Cys Ile Ala Ser Asn Ala Ala Gly Asn Asp Thr Phe Thr Ala
            485                 490                 495

Ser Leu Thr Val Lys Gly Phe Ala Ser Asp Arg Phe Leu Tyr Ala Asn
            500                 505                 510

Arg Thr Pro Met Tyr Met Thr Asp Ser Asn Asp Thr Ile Ser Asn Gly
            515                 520                 525

Thr Asn Ala Asn Thr Phe Ser Leu Asp Leu Lys Thr Ile Leu Val Ser
            530                 535                 540

Thr Ala Met Gly Cys Phe Thr Phe Leu Gly Val Val Leu Phe Cys Phe
545                 550                 555                 560

Leu Leu Leu Phe Val Trp Ser Arg Gly Lys Gly Lys His Lys Asn Ser
                    565                 570                 575

Ile Asp Leu Glu Tyr Val Pro Arg Lys Asn Asn Gly Ala Val Val Glu
            580                 585                 590

Gly Glu Val Ala Gly Pro Arg Arg Phe Asn Met Lys Met Ile
            595                 600                 605

<210> SEQ ID NO 3
<211> LENGTH: 3669
<212> TYPE: DNA
<213> ORGANISM: Mus musculus

<400> SEQUENCE: 3
gccagtgcac tctagaaacc cagcctgcat gtagaaagcc ctgtctactg cagaagatga      60
ttcctgcccc gggttaaatg tgcacaactc gcggaaatgc cagtaccttc cacctgaagg     120
cacttagtgg ctagaaaacc agcaatctac cccgaaacac actgtactaa acacagcaag     180
agaccacaat gattggacat atacctatga agatccactt tgagaaagat gccagttgtt     240
ccacaggatg cactttgaga atgaattcat tctagctggt acagcaaaag gagtgcatta     300
aggcccgtaa ccaaggtgta gacaaagaag tggagtcatg cttcacacgg ctataccatg     360
ctggcagcca ttcctgggtc tggctgtggt gttactctta atgggatcca ccattggctg     420
tcctgctcgc tgtgagtgct ccgcccagaa caaatctgtt agctgccaca gaagacgatt     480
gctcgcgatc ccagaaggca ttcccattga gaccaaaatc ttggacctga gcaaaaatcg     540
```

```
actaaagagc ataaaccctg aagagttcat ctcatatcct ctgttggagg agatagactt    600
gagcgacaac attattgcca atgtggagcc tggggcattt aacaatctct ttaacctgcg    660
ttccctccgc ctaaaaggca atcgccttaa gttggtccct ttaggagtat tcacaggact    720
gtccaacctc accaagcttg acattagtga gaataagatt gtcattttgc tggactacat    780
gttccaggat ctgcataacc tgaagtctct agaagtgggg gacaatgatt tagtgtatat    840
ctcacacagg gccttcagcg gactacttag cttggagcag ctcaccctgg agaagtgcaa    900
cttgacagca gtaccaacag aagccctttc ccatctccgc agcctcatcg ccctgcatct    960
gaagcatctc aatatcaaca atatgcctgt gtatgccttt aaaagattgt tccacctgaa   1020
aaacctagag atcgactatt ggcctttgtt ggatttgatg ccagccaaca gcctctatgg   1080
tctcaacctc acgtcccttt caatcaccaa accaacctg tccactgtcc ccttcctcgc   1140
ctttaaacac cttgtatacc tgacccacct taacctctcc tacaatccca tcagcactat   1200
tgaagctggc atgttctctg acctgatccg cctacaggag cttcatatag tggggggccca   1260 gctccgcact attgagcctc actccttcca agggctccgc ttcctccgtg tgctcaatgt   1320
atctcagaac ctgctggaaa cattggaaga gaacgtcttc tcctcccta gggctttgga   1380 ggtcctgagc attaacaaca acccactagc ctgtgactgc cgactcctct ggctcctgca   1440
gcgacaaccc aacctgcagt ttggggggcca gcagcccatg tgtgctgggc cagacaccat   1500
ccgtgagaga tcatttaagg atttccatag cactgctctt tcttttttatt ttacctgcaa   1560 aaaacccaaa atccgtgaaa agaagttaca gcatctcctc gtggatgaag ggcaaacggt   1620
ccagctggag tgcaacgctg atggagaccc gcagcccgtg atttcctggg tgacacctcg   1680
aaggcgtttt atcaccacca agtccaacgg aagggccact gtgttgggtg atggcaccttt   1740 ggaaatccgt tttgcccagg atcaagacag tgggatgtat gtttgcatcg cgagcaacgc   1800
tgctgggaac gataccttca cagcatctct cactgtgaag ggattcacgt cagaccgctt   1860
cctttacgca aacaggaccc ctatgtacat gactgactcc aacgacaccg tttccaacgg   1920
cactaatgcc aatactttct ccctggacct taaaacaata ctggtatcta cagccatggg   1980
ctgtttcaca ttcctgggag tggttttatt ttgttttctc cttcttttg tgtggagccg   2040 agggaaaggc aagcacaaaa acagcattga ccttgagtat gtgccccgaa aaaacaatgg   2100
tgctgttgtg gaaggggagg tggctggccc caggaggttc aacatgaaaa tgatctaagg   2160
gcccaccaca cactactgtc tctctgttac tgttggtcgt gagtaagacg tctgatagag   2220
tgactcgatc acaaggttat cgggcagctt tgcgcagctg cccctgtgtc aaagcagggt   2280
ccatggaagc aggaagactt ctcatggaga ctggctgatt agaggcaggc aggcatgtgt   2340
cagagccctt cacacagtgg gatactaatt gtttgcattg caaatattgg cattctgggg   2400
atctcagcaa tgaacctgaa cctttggctc atgctgatgg acaataattc aacatttttct   2460 accactgcaa aactaaaagg aaaaaaaaatt aaaagaaca acctacagtg taggatttac   2520
atattaaaaa gacacatttg tctaaaacat actctacagt caaatttgta tttattatca   2580
tttgttaaaa ccttgcatca tacaatactg ttggttcagc accaaaaaga gatcaatata   2640
ttcttttttt tgaaacatat atgctgtata tgttttaaag caatatgaat gagaggttgt   2700
gcttttagtt actccaccagt atagatccaa gtgtggtttc accttccttt tacctgcaga   2760
taaacctgag aatagatccc tggaatacta ggcagagatg tgttgagatg tgtatgtctg   2820
atgtaggatg ccaagaaaca agacccaagt caaaactgct caactctgtt aacttctgtt   2880
```

```
actataaata aaggcatgtg cctagttttg atacagaatg gaatattttt tatacataca    2940
ctaccaacct ggaccagttt actgtaacag aagcccttgg tttctccaga aggcggtaca    3000
tcgctagggg tacctataga atacaaggta ggtgtcactc ttaaaagtaa tccatgtagc    3060
tactgcttag ttttactttc gccagtcact gctaatgggt taatgaccaa tggaaaagag    3120
aatattgatt atatagaatt atttggcaat attcaccaat agctaatatc aataattctg    3180
ttgtccgaaa gccctctgaa taaggaggtt tcagaagtca ataggaagca gggagagaca    3240
agagcatcac agcagcgatt cagccaatga tctctttcaa atgtggcagc tgcctgccgg    3300
atggctacaa atcaaaggga atacgctgca catgccagcc caacttctat ccaagtacta    3360
tacacagagt aggaccacag ttaggcaact tcaggatatt cctctgcttc ctgatcaaga    3420
tctttagttt catattgaaa accatattac acagctacga ggaatatgtt ttgtgtgaaa    3480
gaagtaaaag tagtgaaaga aaaccaata tagatctaaa aaacaatgtt ttgttccttc     3540
actggggaag agctaagctt atagttctac aaatatgtaa tgctgtgcca attcttttac    3600
cttcttgacc tgagcatatt tgcccaatta agttgatatt aatgttacta atgcaaacat    3660
aaccagaaa                                                            3669
```

<210> SEQ ID NO 4
<211> LENGTH: 606
<212> TYPE: PRT
<213> ORGANISM: Mus musculus

<400> SEQUENCE: 4

```
Met Leu His Thr Ala Ile Pro Cys Trp Gln Pro Phe Leu Gly Leu Ala
1               5                   10                  15

Val Val Leu Leu Leu Met Gly Ser Thr Ile Gly Cys Pro Ala Arg Cys
            20                  25                  30

Glu Cys Ser Ala Gln Asn Lys Ser Val Ser Cys His Arg Arg Arg Leu
        35                  40                  45

Leu Ala Ile Pro Glu Gly Ile Pro Ile Glu Thr Lys Ile Leu Asp Leu
    50                  55                  60

Ser Lys Asn Arg Leu Lys Ser Ile Asn Pro Glu Glu Phe Ile Ser Tyr
65                  70                  75                  80

Pro Leu Leu Glu Glu Ile Asp Leu Ser Asp Asn Ile Ile Ala Asn Val
                85                  90                  95

Glu Pro Gly Ala Phe Asn Asn Leu Phe Asn Leu Arg Ser Leu Arg Leu
            100                 105                 110

Lys Gly Asn Arg Leu Lys Leu Val Pro Leu Gly Val Phe Thr Gly Leu
        115                 120                 125

Ser Asn Leu Thr Lys Leu Asp Ile Ser Glu Asn Lys Ile Val Ile Leu
    130                 135                 140

Leu Asp Tyr Met Phe Gln Asp Leu His Asn Leu Lys Ser Leu Glu Val
145                 150                 155                 160

Gly Asp Asn Asp Leu Val Tyr Ile Ser His Arg Ala Phe Ser Gly Leu
                165                 170                 175

Leu Ser Leu Glu Gln Leu Thr Leu Glu Lys Cys Asn Leu Thr Ala Val
            180                 185                 190

Pro Thr Glu Ala Leu Ser His Leu Arg Ser Leu Ile Ala Leu His Leu
        195                 200                 205

Lys His Leu Asn Ile Asn Asn Met Pro Val Tyr Ala Phe Lys Arg Leu
    210                 215                 220

Phe His Leu Lys Asn Leu Glu Ile Asp Tyr Trp Pro Leu Leu Asp Leu
```

```
225                 230                 235                 240
Met Pro Ala Asn Ser Leu Tyr Gly Leu Asn Leu Thr Ser Leu Ser Ile
                245                 250                 255
Thr Asn Thr Asn Leu Ser Thr Val Pro Phe Leu Ala Phe Lys His Leu
                260                 265                 270
Val Tyr Leu Thr His Leu Asn Leu Ser Tyr Asn Pro Ile Ser Thr Ile
                275                 280                 285
Glu Ala Gly Met Phe Ser Asp Leu Ile Arg Leu Gln Glu Leu His Ile
            290                 295                 300
Val Gly Ala Gln Leu Arg Thr Ile Glu Pro His Ser Phe Gln Gly Leu
305                 310                 315                 320
Arg Phe Leu Arg Val Leu Asn Val Ser Gln Asn Leu Leu Glu Thr Leu
                325                 330                 335
Glu Glu Asn Val Phe Ser Ser Pro Arg Ala Leu Glu Val Leu Ser Ile
                340                 345                 350
Asn Asn Asn Pro Leu Ala Cys Asp Cys Arg Leu Leu Trp Leu Leu Gln
                355                 360                 365
Arg Gln Pro Asn Leu Gln Phe Gly Gly Gln Pro Met Cys Ala Gly
            370                 375                 380
Pro Asp Thr Ile Arg Glu Arg Ser Phe Lys Asp Phe His Ser Thr Ala
385                 390                 395                 400
Leu Ser Phe Tyr Phe Thr Cys Lys Lys Pro Lys Ile Arg Glu Lys Lys
                405                 410                 415
Leu Gln His Leu Leu Val Asp Glu Gly Gln Thr Val Gln Leu Glu Cys
                420                 425                 430
Asn Ala Asp Gly Asp Pro Gln Pro Val Ile Ser Trp Val Thr Pro Arg
            435                 440                 445
Arg Arg Phe Ile Thr Thr Lys Ser Asn Gly Arg Ala Thr Val Leu Gly
            450                 455                 460
Asp Gly Thr Leu Glu Ile Arg Phe Ala Gln Asp Gln Asp Ser Gly Met
465                 470                 475                 480
Tyr Val Cys Ile Ala Ser Asn Ala Ala Gly Asn Asp Thr Phe Thr Ala
                485                 490                 495
Ser Leu Thr Val Lys Gly Phe Thr Ser Asp Arg Phe Leu Tyr Ala Asn
                500                 505                 510
Arg Thr Pro Met Tyr Met Thr Asp Ser Asn Asp Thr Val Ser Asn Gly
            515                 520                 525
Thr Asn Ala Asn Thr Phe Ser Leu Asp Leu Lys Thr Ile Leu Val Ser
            530                 535                 540
Thr Ala Met Gly Cys Phe Thr Phe Leu Gly Val Val Leu Phe Cys Phe
545                 550                 555                 560
Leu Leu Leu Phe Val Trp Ser Arg Gly Lys Gly His Lys Asn Ser
                565                 570                 575
Ile Asp Leu Glu Tyr Val Pro Arg Lys Asn Asn Gly Ala Val Val Glu
            580                 585                 590
Gly Glu Val Ala Gly Pro Arg Arg Phe Asn Met Lys Met Ile
            595                 600                 605

<210> SEQ ID NO 5
<211> LENGTH: 2941
<212> TYPE: DNA
<213> ORGANISM: Rattus norvegicus

<400> SEQUENCE: 5
```

-continued

```
gtgccagggc actctagaaa cccagcctgc atgtagacag ccctgcctac tgcagaagat        60
gattcctgcc ccgggttaaa cgtgtacaac tcgtggaaat gccagtacct tccacctgaa       120
ggcacttagt ggctagaaaa ccagcaatct accccgaaac acactgtact aaacacagca       180
agagaccaca atgattggac atagacctat aaggatacac tttgagaaag atgccagttg       240
ttcctcagga tgcactttga aaatgcagtc attctagctg gtaccgcaaa atgagtgcat       300
taaggcccat aaccaaggtg tagaataaac agtggagtca tgcttcacac ggctatacca       360
tgctggcagc cattcctggg tctggctatg tgttactct tcatgggatc caccattggc        420
tgtcctgctc gctgtgagtg ctctgcccag aacaaatctg ttagctgcca cagaagacgc       480
ttgatcgcga tccccgaagg cattcccatt gagaccaaaa tcttggacct gagcaaaaat       540
cgactaaaga gcataaaccc cgaagaattc atctcatatc ctctgttgga ggagatagac       600
ttgagcgaca acatcatcgc caatgtagaa cctggggcat ttaacaatct ctttaacctg       660
cgttccctcc gcctaaaagg caatcgcctt aagttggtcc ctttgggagt attcacggga       720
ctgtccaacc tcaccaagct tgacattagt gagaataaga ttgtcatttt gctggactac       780
atgttccagg atctgcataa cctgaagtct ctagaagtgg gggacaatga tttggtttat       840
atatcacaca gggccttcag tggactattt agcttggagc agctcaccct ggagaagtgc       900
aacttgacag cggtaccaac agaagcccct tcccatctcc gcagcctcat caccctgcat       960
ctgaagcatc tcaatatcaa caatatgcct gtgtatgcct ttaaaagatt attccacctg      1020
aaacaactag agatcgacta ttggccattg ctggatatga tgccagccaa tagcctctat      1080
ggtctcaacc tcacatccct ctcgatcact aacaccaacc tgtccactgt ccctttcctc      1140
gcctttaaac accttgtata cctgacccac cttaacctct cctacaatcc catcagcact      1200
attgaagcag gcatgttctc tgacctgatc cgcctacagg agcttcatgt agtcggggcc      1260
cagctccgca ccattgaacc tcactccttc caagggctcc gcttcctccg cgtgctcaat      1320
gtatctcaga acctgctgga aacattggaa gagaatgtct tctcttcccc tagggctttg      1380
gaggtcctga gcattaacaa taacccacta gcgtgcgact gccgacttct ctggctcctg      1440
cagcgacagg ccaccctgca gtttggaggc cagcagccca tgtgtgccgg gccagacacc      1500
atacgtgaga ggtcatttaa ggatttccat agcactgctc tttcttttta ttttacctgc      1560
aaaaaaccca aaatccgtga aaagaagtta cagcacctcc tagtggacga aggacagacg      1620
gtccagctgg agtgcaacgc ggatggagac ccccagcccg tgatttcctg ggtgacacct      1680
cgaaggcgtt ttatcaccac caagtccaac ggaagggcca ctgtgttggg tgatggcacc      1740
ttagaaatcc gtttcgccca ggatcaagac agtgggatgt atgtttgcat agctagcaat      1800
gctgctggga atgacacctt cacggcatct ctcactgtga agggattcac ttcagaccgc      1860
ttcctttacg caaacaggac ccctatgtac atgactgact ccaatgacac cgtttccaac      1920
ggcactaatg ccaatacttt ttccctggac cttaaaacaa tactggtatc tacagccatg      1980
ggctgtttca cattcctggg agtggtttta ttttgttttc ccttcttttt tgtgtggagc      2040
cgaggaaagg gcaaacacaa aaacagcatt gaccttgagt atgtgccccg aaaaaacaat      2100
ggtgctgttg cagaagggga ggtggctgga cccaggaggt caacatgaa aatgatataa       2160 gggcccacca cacacacact actactgtct ctgtgttact gttggtaatg agtaagacgt      2220
ctgatatagc gagtccatca caaggtgatc aggcagcttc acacagctgc ccctgtgtca      2280
aagcagggtc catggaagct ggaagacttc tcatggacac tggctgatta gaggcaggca      2340
ggcatgtgtc agagcccttc acacagtggg atactaattg tttgcattgc aaatattggc      2400
```

```
attctgggga tctcagtaat gaccctgaac ctttggctca tgctgacgga caaaaattca   2460
acattttcta ccactgcaaa actaaaagaa aaaaaattta aaaggaacaa cctacagtgt   2520
aggatttaca tattaaaaaa agacacattt gtctaaaaca tactctacgg taaaatttgt   2580
atttattatc atttgttaaa accttgcatc atacaatact gttggttcag caccaaaaaa   2640
aaaaaaaaaa aaaaaaagag agatcaatat attctttttt gaaacatata tgctgtatat   2700
gttttaaagc aatatgaatg agaggttgtg cttttagtta ctcaccagta tagatccaag   2760
tgtggtctca ctttcctttt atccgcagag aaacctgaga atagatccct ggaataatag   2820
gctgagatgt gttgagatgt gtatgtctga tgtaggatgc caagatacaa gagcccagtc   2880
aaaactgctc aactctgtta acttctgtta ctataaataa aggcatgtgc ctagttttga   2940
t                                                                   2941
```

<210> SEQ ID NO 6
<211> LENGTH: 606
<212> TYPE: PRT
<213> ORGANISM: Rattus norvegicus

<400> SEQUENCE: 6

```
Met Leu His Thr Ala Ile Pro Cys Trp Gln Pro Phe Leu Gly Leu Ala
1               5                   10                  15

Met Val Leu Leu Phe Met Gly Ser Thr Ile Gly Cys Pro Ala Arg Cys
            20                  25                  30

Glu Cys Ser Ala Gln Asn Lys Ser Val Ser Cys His Arg Arg Arg Leu
        35                  40                  45

Ile Ala Ile Pro Glu Gly Ile Pro Ile Glu Thr Lys Ile Leu Asp Leu
    50                  55                  60

Ser Lys Asn Arg Leu Lys Ser Ile Asn Pro Glu Glu Phe Ile Ser Tyr
65                  70                  75                  80

Pro Leu Leu Glu Glu Ile Asp Leu Ser Asp Asn Ile Ile Ala Asn Val
                85                  90                  95

Glu Pro Gly Ala Phe Asn Asn Leu Phe Asn Leu Arg Ser Leu Arg Leu
            100                 105                 110

Lys Gly Asn Arg Leu Lys Leu Val Pro Leu Gly Val Phe Thr Gly Leu
        115                 120                 125

Ser Asn Leu Thr Lys Leu Asp Ile Ser Glu Asn Lys Ile Val Ile Leu
    130                 135                 140

Leu Asp Tyr Met Phe Gln Asp Leu His Asn Leu Lys Ser Leu Glu Val
145                 150                 155                 160

Gly Asp Asn Asp Leu Val Tyr Ile Ser His Arg Ala Phe Ser Gly Leu
                165                 170                 175

Phe Ser Leu Glu Gln Leu Thr Leu Glu Lys Cys Asn Leu Thr Ala Val
            180                 185                 190

Pro Thr Glu Ala Leu Ser His Leu Arg Ser Leu Ile Thr Leu His Leu
        195                 200                 205

Lys His Leu Asn Ile Asn Asn Met Pro Val Tyr Ala Phe Lys Arg Leu
    210                 215                 220

Phe His Leu Lys Gln Leu Glu Ile Asp Tyr Trp Pro Leu Leu Asp Met
225                 230                 235                 240

Met Pro Ala Asn Ser Leu Tyr Gly Leu Asn Leu Thr Ser Leu Ser Ile
                245                 250                 255

Thr Asn Thr Asn Leu Ser Thr Val Pro Phe Leu Ala Phe Lys His Leu
            260                 265                 270
```

-continued

```
Val Tyr Leu Thr His Leu Asn Leu Ser Tyr Asn Pro Ile Ser Thr Ile
            275                 280                 285

Glu Ala Gly Met Phe Ser Asp Leu Ile Arg Leu Gln Glu Leu His Val
290                 295                 300

Val Gly Ala Gln Leu Arg Thr Ile Glu Pro His Ser Phe Gln Gly Leu
305                 310                 315                 320

Arg Phe Leu Arg Val Leu Asn Val Ser Gln Asn Leu Leu Glu Thr Leu
            325                 330                 335

Glu Glu Asn Val Phe Ser Ser Pro Arg Ala Leu Glu Val Leu Ser Ile
            340                 345                 350

Asn Asn Asn Pro Leu Ala Cys Asp Cys Arg Leu Leu Trp Leu Leu Gln
            355                 360                 365

Arg Gln Ala Thr Leu Gln Phe Gly Gly Gln Gln Pro Met Cys Ala Gly
            370                 375                 380

Pro Asp Thr Ile Arg Glu Arg Ser Phe Lys Asp Phe His Ser Thr Ala
385                 390                 395                 400

Leu Ser Phe Tyr Phe Thr Cys Lys Lys Pro Lys Ile Arg Glu Lys Lys
            405                 410                 415

Leu Gln His Leu Leu Val Asp Glu Gly Gln Thr Val Gln Leu Glu Cys
            420                 425                 430

Asn Ala Asp Gly Asp Pro Gln Pro Val Ile Ser Trp Val Thr Pro Arg
            435                 440                 445

Arg Arg Phe Ile Thr Thr Lys Ser Asn Gly Arg Ala Thr Val Leu Gly
            450                 455                 460

Asp Gly Thr Leu Glu Ile Arg Phe Ala Gln Asp Gln Asp Ser Gly Met
465                 470                 475                 480

Tyr Val Cys Ile Ala Ser Asn Ala Ala Gly Asn Asp Thr Phe Thr Ala
            485                 490                 495

Ser Leu Thr Val Lys Gly Phe Thr Ser Asp Arg Phe Leu Tyr Ala Asn
            500                 505                 510

Arg Thr Pro Met Tyr Met Thr Asp Ser Asn Asp Thr Val Ser Asn Gly
            515                 520                 525

Thr Asn Ala Asn Thr Phe Ser Leu Asp Leu Lys Thr Ile Leu Val Ser
            530                 535                 540

Thr Ala Met Gly Cys Phe Thr Phe Leu Gly Val Val Leu Phe Cys Phe
545                 550                 555                 560

Leu Leu Leu Phe Val Trp Ser Arg Gly Lys Gly His Lys Asn Ser
            565                 570                 575

Ile Asp Leu Glu Tyr Val Pro Arg Lys Asn Asn Gly Ala Val Ala Glu
            580                 585                 590

Gly Glu Val Ala Gly Pro Arg Arg Phe Asn Met Lys Met Ile
            595                 600                 605
```

<210> SEQ ID NO 7
<211> LENGTH: 5
<212> TYPE: PRT
<213> ORGANISM: Artificial Sequence
<220> FEATURE:
<223> OTHER INFORMATION: Antibody C09 VH-CDR1

<400> SEQUENCE: 7

```
Leu Tyr Trp Met Asn
1               5
```

<210> SEQ ID NO 8

```
<211> LENGTH: 17
<212> TYPE: PRT
<213> ORGANISM: Artificial Sequence
<220> FEATURE:
<223> OTHER INFORMATION: Antibody C09 VH-CDR2

<400> SEQUENCE: 8

Ser Ile Ser Pro Ser Gly Gly Trp Thr Lys Tyr Ala Asp Ser Val Lys
1               5                   10                  15

Gly

<210> SEQ ID NO 9
<211> LENGTH: 10
<212> TYPE: PRT
<213> ORGANISM: Artificial Sequence
<220> FEATURE:
<223> OTHER INFORMATION: Antibody C09 VH-CDR3

<400> SEQUENCE: 9

Asp His Trp Gly Ser Gly Ser Pro Asp Tyr
1               5                   10

<210> SEQ ID NO 10
<211> LENGTH: 119
<212> TYPE: PRT
<213> ORGANISM: Artificial Sequence
<220> FEATURE:
<223> OTHER INFORMATION: Antibody C09 VH

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Leu Tyr
            20                  25                  30

Trp Met Asn Trp Val Arg Gln Ala Pro Gly Lys Gly Leu Glu Trp Val
        35                  40                  45

Ser Ser Ile Ser Pro Ser Gly Gly Trp Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp His Trp Gly Ser Gly Ser Pro Asp Tyr Trp Gly Gln Gly
            100                 105                 110

Thr Leu Val Thr Val Ser Ser
        115

<210> SEQ ID NO 11
<211> LENGTH: 14
<212> TYPE: PRT
<213> ORGANISM: Artificial Sequence
<220> FEATURE:
<223> OTHER INFORMATION: Antibody C09 VL-CDR1

<400> SEQUENCE: 11

Thr Gly Ser Ser Arg Asp Val Gly Gly Tyr Asp Tyr Val Ser
1               5                   10

<210> SEQ ID NO 12
<211> LENGTH: 7
<212> TYPE: PRT
<213> ORGANISM: Artificial Sequence
<220> FEATURE:
```

<223> OTHER INFORMATION: Antibody C09 VL-CDR2

<400> SEQUENCE: 12

Glu Val Thr Lys Arg Pro Ser
1               5

<210> SEQ ID NO 13
<211> LENGTH: 10
<212> TYPE: PRT
<213> ORGANISM: Artificial Sequence
<220> FEATURE:
<223> OTHER INFORMATION: Antibody C09 VL-CDR3

<400> SEQUENCE: 13

Cys Ser Tyr Ala Gly Ala Asn Thr Tyr Val
1               5                   10

<210> SEQ ID NO 14
<211> LENGTH: 110
<212> TYPE: PRT
<213> ORGANISM: Artificial Sequence
<220> FEATURE:
<223> OTHER INFORMATION: Antibody C09 VL

<400> SEQUENCE: 14

Gln Ser Val Leu Thr Gln Pro Pro Ser Ala Ser Gly Ser Pro Gly Gln
1               5                   10                  15

Ser Leu Thr Ile Ser Cys Thr Gly Ser Ser Arg Asp Val Gly Gly Tyr
            20                  25                  30

Asp Tyr Val Ser Trp Phe Gln Gln His Pro Gly Lys Ala Pro Lys Leu
        35                  40                  45

Val Ile Ser Glu Val Thr Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Pro Glu Asp Glu Ala Asp Tyr Tyr Cys Cys Ser Tyr Ala Gly Ala
                85                  90                  95

Asn Thr Tyr Val Phe Gly Ser Gly Thr Arg Val Thr Val Leu
            100                 105                 110

<210> SEQ ID NO 15
<211> LENGTH: 15
<212> TYPE: DNA
<213> ORGANISM: Artificial Sequence
<220> FEATURE:
<223> OTHER INFORMATION: Antibody C09 VH-CDR1

<400> SEQUENCE: 15
ctttactgga tgaat                                                15

<210> SEQ ID NO 16
<211> LENGTH: 51
<212> TYPE: DNA
<213> ORGANISM: Artificial Sequence
<220> FEATURE:
<223> OTHER INFORMATION: Antibody C09 VH-CDR2

<400> SEQUENCE: 16
tctatctctc cttctggtgg ctggactaag tatgctgact ccgttaaagg t          51

<210> SEQ ID NO 17
<211> LENGTH: 30
<212> TYPE: DNA

<213> ORGANISM: Artificial Sequence
<220> FEATURE:
<223> OTHER INFORMATION: Antibody C09 VH-CDR3

<400> SEQUENCE: 17
gatcattggg gttcagggag ccccgactac                                    30

<210> SEQ ID NO 18
<211> LENGTH: 357
<212> TYPE: DNA
<213> ORGANISM: Artificial Sequence
<220> FEATURE:
<223> OTHER INFORMATION: Antibody C09 VH

<400> SEQUENCE: 18
gaagttcaat tgttagagtc tggtggcggt cttgttcagc ctggtggttc tttacgtctt    60
tcttgcgctg cttccggatt cactttctct ctttactgga tgaattgggt tcgccaagct   120
cctggtaaag gtttggagtg gtttcttct atctctcctt ctggtggctg gactaagtat    180
gctgactccg ttaaaggtcg cttcactatc tctagagaca actctaagaa tactctctac   240
ttgcagatga acagcttaag ggctgaggac acggccgtgt attactgtgc aagagatcat   300
tggggttcag ggaccccga ctactggggc agggaaccc tggtcaccgt ctcaagc       357

<210> SEQ ID NO 19
<211> LENGTH: 42
<212> TYPE: DNA
<213> ORGANISM: Artificial Sequence
<220> FEATURE:
<223> OTHER INFORMATION: Antibody C09-VL CDR1

<400> SEQUENCE: 19
actggatcca gccgtgacgt tggtggttat gattatgtct cc                     42

<210> SEQ ID NO 20
<211> LENGTH: 21
<212> TYPE: DNA
<213> ORGANISM: Artificial Sequence
<220> FEATURE:
<223> OTHER INFORMATION: Antibody C09 VL-CDR2

<400> SEQUENCE: 20
gaggtcacta agcggccctc a                                             21

<210> SEQ ID NO 21
<211> LENGTH: 30
<212> TYPE: DNA
<213> ORGANISM: Artificial Sequence
<220> FEATURE:
<223> OTHER INFORMATION: Antibody C09 VL-CDR3

<400> SEQUENCE: 21
tgctcatatg caggcgccaa cacttatgtc                                    30

<210> SEQ ID NO 22
<211> LENGTH: 330
<212> TYPE: DNA
<213> ORGANISM: Artificial Sequence
<220> FEATURE:
<223> OTHER INFORMATION: Antibody C09 VL

<400> SEQUENCE: 22
cagagcgtct tgactcagcc tccctccgcg tccgggtctc tggacagtc actcaccatc    60 tcctgcactg gatccagccg tgacgttggt ggttatgatt atgtctcctg gttccaacaa   120

```
cacccaggca aagcccccaa actcgtgatt tctgaggtca ctaagcggcc ctcaggggtc    180
cctgatcggt tctctggctc caagtctggc aacacggcct ccctgaccgt ctctggactc    240
caacctgagg atgaggctga ttattattgc tgctcatatg caggcgccaa cacttatgtc    300
ttcggaagtg ggaccagagt caccgtcctg                                     330

<210> SEQ ID NO 23
<211> LENGTH: 25
<212> TYPE: DNA
<213> ORGANISM: Homo sapiens

<400> SEQUENCE: 23
accttgtata cctgacccac cttaa                                           25

<210> SEQ ID NO 24
<211> LENGTH: 25
<212> TYPE: DNA
<213> ORGANISM: Rattus norvegicus

<400> SEQUENCE: 24
agagaacatg cctgcttcaa tagtg                                           25

<210> SEQ ID NO 25
<211> LENGTH: 25
<212> TYPE: DNA
<213> ORGANISM: Mus musculus

<400> SEQUENCE: 25
agagaacatg ccagcttcaa tagtg                                           25

<210> SEQ ID NO 26
<211> LENGTH: 16
<212> TYPE: DNA
<213> ORGANISM: Artificial Sequence
<220> FEATURE:
<223> OTHER INFORMATION: MGB probe

<400> SEQUENCE: 26
cctctcctac aatccc                                                     16

<210> SEQ ID NO 27
<211> LENGTH: 728
<212> TYPE: PRT
<213> ORGANISM: Homo sapiens

<400> SEQUENCE: 27

Met Leu His Thr Ala Ile Ser Cys Trp Gln Pro Phe Leu Gly Leu Ala
1               5                   10                  15

Val Val Leu Ile Phe Met Gly Ser Thr Ile Gly Cys Pro Ala Arg Cys
            20                  25                  30

Glu Cys Ser Ala Gln Asn Lys Ser Val Ser Cys His Arg Arg Arg Leu
        35                  40                  45

Ile Ala Ile Pro Glu Gly Ile Pro Ile Glu Thr Lys Ile Leu Asp Leu
    50                  55                  60

Ser Lys Asn Arg Leu Lys Ser Val Asn Pro Glu Glu Phe Ile Ser Tyr
65                  70                  75                  80

Pro Leu Leu Glu Glu Ile Asp Leu Ser Asp Asn Ile Ile Ala Asn Val
                85                  90                  95

Glu Pro Gly Ala Phe Asn Asn Leu Phe Asn Leu Arg Ser Leu Arg Leu
            100                 105                 110
```

Lys Gly Asn Arg Leu Lys Leu Val Pro Leu Gly Val Phe Thr Gly Leu
            115                 120                 125

Ser Asn Leu Thr Lys Leu Asp Ile Ser Glu Asn Lys Ile Val Ile Leu
130                 135                 140

Leu Asp Tyr Met Phe Gln Asp Leu His Asn Leu Lys Ser Leu Glu Val
145                 150                 155                 160

Gly Asp Asn Asp Leu Val Tyr Ile Ser His Arg Ala Phe Ser Gly Leu
            165                 170                 175

Leu Ser Leu Glu Gln Leu Thr Leu Glu Lys Cys Asn Leu Thr Ala Val
            180                 185                 190

Pro Thr Glu Ala Leu Ser His Leu Arg Ser Leu Ile Ser Leu His Leu
            195                 200                 205

Lys His Leu Asn Ile Asn Asn Met Pro Val Tyr Ala Phe Lys Arg Leu
            210                 215                 220

Phe His Leu Lys His Leu Glu Ile Asp Tyr Trp Pro Leu Leu Asp Met
225                 230                 235                 240

Met Pro Ala Asn Ser Leu Tyr Gly Leu Asn Leu Thr Ser Leu Ser Val
            245                 250                 255

Thr Asn Thr Asn Leu Ser Thr Val Pro Phe Leu Ala Phe Lys His Leu
            260                 265                 270

Val Tyr Leu Thr His Leu Asn Leu Ser Tyr Asn Pro Ile Ser Thr Ile
            275                 280                 285

Glu Ala Gly Met Phe Ser Asp Leu Ile Arg Leu Gln Glu Leu His Ile
            290                 295                 300

Val Gly Ala Gln Leu Arg Thr Ile Glu Pro His Ser Phe Gln Gly Leu
305                 310                 315                 320

Arg Phe Leu Arg Val Leu Asn Val Ser Gln Asn Leu Leu Glu Thr Leu
            325                 330                 335

Glu Glu Asn Val Phe Ser Ser Pro Arg Ala Leu Glu Val Leu Ser Ile
            340                 345                 350

Asn Asn Asn Pro Leu Ala Cys Asp Cys Arg Leu Leu Trp Ile Leu Gln
            355                 360                 365

Arg Gln Pro Thr Leu Gln Phe Gly Gly Gln Gln Pro Met Cys Ala Gly
            370                 375                 380

Pro Asp Thr Ile Arg Glu Arg Ser Phe Lys Asp Phe His Ser Thr Ala
385                 390                 395                 400

Leu Ser Phe Tyr Phe Thr Cys Lys Lys Pro Lys Ile Arg Glu Lys Lys
            405                 410                 415

Leu Gln His Leu Leu Val Asp Glu Gly Gln Thr Val Gln Leu Glu Cys
            420                 425                 430

Ser Ala Asp Gly Asp Pro Gln Pro Val Ile Ser Trp Val Thr Pro Arg
            435                 440                 445

Arg Arg Phe Ile Thr Thr Lys Ser Asn Gly Arg Ala Thr Val Leu Gly
            450                 455                 460

Asp Gly Thr Leu Glu Ile Arg Phe Ala Gln Asp Gln Asp Ser Gly Met
465                 470                 475                 480

Tyr Val Cys Ile Ala Ser Asn Ala Ala Gly Asn Asp Thr Phe Thr Ala
            485                 490                 495

Ser Leu Thr Val Val Asp Lys Thr His Thr Cys Pro Pro Cys Pro Ala
            500                 505                 510

Pro Glu Leu Leu Gly Gly Pro Ser Val Phe Leu Phe Pro Pro Lys Pro
            515                 520                 525

Lys Asp Thr Leu Met Ile Ser Arg Thr Pro Glu Val Thr Cys Val Val
    530                 535                 540

Val Asp Val Ser His Glu Asp Pro Glu Val Lys Phe Asn Trp Tyr Val
545                 550                 555                 560

Asp Gly Val Glu Val His Asn Ala Lys Thr Lys Pro Arg Glu Glu Gln
                565                 570                 575

Tyr Asn Ser Thr Tyr Arg Val Val Ser Val Leu Thr Val Leu His Gln
            580                 585                 590

Asp Trp Leu Asn Gly Lys Glu Tyr Lys Cys Lys Val Ser Asn Lys Ala
        595                 600                 605

Leu Pro Ala Pro Ile Glu Lys Thr Ile Ser Lys Ala Lys Gly Gln Pro
    610                 615                 620

Arg Glu Pro Gln Val Tyr Thr Leu Pro Pro Ser Arg Asp Glu Leu Thr
625                 630                 635                 640

Lys Asn Gln Val Ser Leu Thr Cys Leu Val Lys Gly Phe Tyr Pro Ser
                645                 650                 655

Asp Ile Ala Val Glu Trp Glu Ser Asn Gly Gln Pro Glu Asn Asn Tyr
            660                 665                 670

Lys Thr Thr Pro Pro Val Leu Asp Ser Asp Gly Ser Phe Phe Leu Tyr
        675                 680                 685

Ser Lys Leu Thr Val Asp Lys Ser Arg Trp Gln Gln Gly Asn Val Phe
    690                 695                 700

Ser Cys Ser Val Met His Glu Ala Leu His Asn His Tyr Thr Gln Lys
705                 710                 715                 720

Ser Leu Ser Leu Ser Pro Gly Lys
                725

<210> SEQ ID NO 28
<211> LENGTH: 40
<212> TYPE: DNA
<213> ORGANISM: Artificial Sequence
<220> FEATURE:
<223> OTHER INFORMATION: digoxigenin-labeled LINGO-2 anti-sense RNA
      probe

<400> SEQUENCE: 28
taatacgact cactataggg acagaagccc tttcccatct                         40

<210> SEQ ID NO 29
<211> LENGTH: 40
<212> TYPE: DNA
<213> ORGANISM: Artificial Sequence
<220> FEATURE:
<223> OTHER INFORMATION: digoxigenin-labeled sense RNA probe

<400> SEQUENCE: 29
taatacgact cactataggg acagaagccc tttcccatct                         40

<210> SEQ ID NO 30
<211> LENGTH: 200
<212> TYPE: DNA
<213> ORGANISM: Artificial Sequence
<220> FEATURE:
<223> OTHER INFORMATION: General Structure for an Oligonucleotide used
      in Preparation of an siRNA Molecule
<220> FEATURE:
<221> NAME/KEY: misc_feature
<222> LOCATION: (1)..(200)
<223> OTHER INFORMATION: n is a, c, g, t or u
<220> FEATURE:
<221> NAME/KEY: misc_feature
<222> LOCATION: (2)..(200)

```
<223> OTHER INFORMATION: nucleotide may be missing

<400> SEQUENCE: 30
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn                                                 200

<210> SEQ ID NO 31
<211> LENGTH: 200
<212> TYPE: DNA
<213> ORGANISM: Artificial Sequence
<220> FEATURE:
<223> OTHER INFORMATION: General Structure for an Oligonucleotide used
      in Preparation of an siRNA Molecule
<220> FEATURE:
<221> NAME/KEY: misc_feature
<222> LOCATION: (1)..(200)
<223> OTHER INFORMATION: n is a, c, g, t or u
<220> FEATURE:
<221> NAME/KEY: misc_feature
<222> LOCATION: (2)..(200)
<223> OTHER INFORMATION: nucleotide may be missing

<400> SEQUENCE: 31
nnnnnnnnnn nnnnnnnnnn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn                                                 200
```